(12) United States Patent
Mansbach et al.

(10) Patent No.: US 12,036,284 B2
(45) Date of Patent: Jul. 16, 2024

(54) COMPOSITIONS AND METHODS OF TREATMENT FOR SEVERE HYPERTRIGLYCERIDEMIA

(71) Applicant: 89bio, Inc., San Francisco, CA (US)

(72) Inventors: Hank Mansbach, San Francisco, CA (US); Leo Tseng, San Francisco, CA (US)

(73) Assignee: 89bio, Inc., San Francisco, CA (US)

( * ) Notice: Subject to any disclaimer, the term of this patent is extended or adjusted under 35 U.S.C. 154(b) by 0 days.

(21) Appl. No.: 18/340,421

(22) Filed: Jun. 23, 2023

(65) Prior Publication Data

US 2023/0414768 A1 Dec. 28, 2023

Related U.S. Application Data

(60) Provisional application No. 63/485,641, filed on Feb. 17, 2023, provisional application No. 63/386,202, filed on Dec. 6, 2022, provisional application No. 63/373,594, filed on Aug. 26, 2022, provisional application No. 63/399,165, filed on Aug. 18, 2022, provisional application No. 63/355,397, filed on Jun. 24, 2022.

(51) Int. Cl.
| | |
|---|---|
| *A61K 38/18* | (2006.01) |
| *A61K 38/01* | (2006.01) |
| *A61K 47/54* | (2017.01) |
| *A61K 47/60* | (2017.01) |
| *A61P 3/06* | (2006.01) |

(52) U.S. Cl.
CPC ............ *A61K 47/60* (2017.08); *A61K 38/018* (2013.01); *A61K 47/549* (2017.08); *A61P 3/06* (2018.01)

(58) Field of Classification Search
CPC .................................. A61K 47/60; A61P 3/06
USPC .......................................................... 514/7.4
See application file for complete search history.

(56) References Cited

U.S. PATENT DOCUMENTS

| | | | |
|---|---|---|---|
| 9,187,532 B2 | 11/2015 | DeFrees | |
| 9,631,004 B2 | 4/2017 | Morin | |
| 9,975,936 B2 | 5/2018 | Cujec | |
| 10,189,883 B2 | 1/2019 | Morin | |
| 10,407,179 B2 | 9/2019 | B | |
| 10,407,479 B2 * | 9/2019 | Kopec | A61P 3/10 |
| 10,874,714 B2 | 12/2020 | DeFrees | |
| 11,427,623 B1 * | 8/2022 | Mansbach | A61K 47/60 |
| 11,596,669 B2 | 3/2023 | Schwartsburd | |
| 2019/0389921 A1 | 12/2019 | Kopec | |
| 2021/0100876 A1 | 4/2021 | DeFrees | |
| 2021/0355183 A1 | 11/2021 | Kopec | |
| 2022/0306712 A1 | 9/2022 | Mansbach | |
| 2023/0090114 A1 | 3/2023 | Rosenstock | |

FOREIGN PATENT DOCUMENTS

| | | |
|---|---|---|
| WO | 2019043457 A2 | 3/2019 |

OTHER PUBLICATIONS

Wang, G.J., "Acute pancreatitis: etiology and common pathogenesis". World J Gastroenterol 15, 1427-1430 (2009).
Anderson, F., "Dyslipidaemic pancreatitis clinical assessment and analysis of disease severity and outcomes". Pancreatology 9, 252-257 (2009).
Yuan, G., "Hypertriglyceridemia: its etiology, effects and treatment". CMAJ 176, 1113-1120 (2007).
Ganda, O.P., "Unmet need for adjunctive dyslipidemia therapy in hypertriglyceridemia management". J Am Coll Cardiol 72, 330-343 (2018).
Toth, P.P., et al. "High triglycerides are associated with increased cardiovascular events, medical costs, and resource use: a real-world administrative claims analysis of statin-treated patients with high residual cardiovascular risk". J Am Heart Assoc 7, e008740 (2018).
Klempfner, R., et al. "Elevated triglyceride level is independently associated with increased all-cause mortality in patients with established coronary heart disease: twenty-two-year follow-up of the Bezafibrate Infarction Prevention Study and Registry". Circ Cardiovasc Qual Outcomes 9, 100-108 (2016).
Nichols, G.A., "Increased cardiovascular risk in hypertriglyceridemic patients with statin-controlled LDL cholesterol". J Clin Endocrinol Metab 103, 3019-3027 (2018).
Libby, P., "Triglycerides on the rise: should we swap seats on the seesaw?" Eur Heart J 36, 774-776 (2015).
Bhatt, D.L., et al. "Cardiovascular risk reduction with icosapent ethyl for hypertriglyceridemia". N Engl J Med 380, 11-22 (2019).
Nichols, G.A., "Increased residual cardiovascular risk in patients with diabetes and high versus normal triglycerides despite statin-controlled LDL cholesterol". Diabetes Obes Metab 21, 366-371 (2019).
Mrani, S.S., et al. "2021 ACC expert consensus decision pathway on the management of ASCVD risk reduction in patients with persistent hypertriglyceridemia: a report of the American College of Cardiology Solution Set Oversight Committee". J Am Coll Cardiol 78, 960-993 (2021).
Alan Jacobsen, "American College of Cardiology. Hypertriglyceridemia management according to the 2018 AHA/ACC guideline"; https://www.acc.org/latest-in-cardiology/articles/2019/01/11/07/39/hypertriglyceridemia-management-according-to-the-2018-aha-acc-guideline. Mar. 2023.
Rosenson, R.S., "Hypertriglyceridemia in adults: management"; https://www.uptodate.com/contents/hypertriglyceridemia-in-adults-management. Mar. 2023.

(Continued)

*Primary Examiner* — Gyan Chandra
(74) *Attorney, Agent, or Firm* — Greenberg Traurig, LLP; Barry Schindler; Natalie Salem

(57) ABSTRACT

Compositions, methods and therapeutic regimens of mutant Fibroblast Growth Factor-21 (FGF-21) peptide conjugates for the treatment of severe hypertriglyceridemia are provided.

27 Claims, 46 Drawing Sheets
(46 of 46 Drawing Sheet(s) Filed in Color)
Specification includes a Sequence Listing.

(56) References Cited

OTHER PUBLICATIONS

Xing, J., et al. "Triglycerides mediate body mass index and nonalcoholic fatty liver disease: a population-based study"; Obes Facts 14, 190-196 (2021).
Rashid, N., "Severe hypertriglyceridemia and factors associated with acute pancreatitis in an integrated health care system"; J Clin Lipidol 10, 880-890 (2016).
Pejic, R.N., "Hypertriglyceridemia"; J Am Board Fam Med 19, 310-316 (2006).
Lin, X., "Metabolic Role of Fibroblast Growth Factor 21 in Liver, Adipose and Nervous System Tissues". Biomed Rep 6, 495-502 (2017).
Tillman, E.J., "FGF21: An Emerging Therapeutic Target for Non-Alcoholic Steatohepatitis and Related Metabolic Diseases"; Front Endocrinol (Lausanne) 11, 601290 (2020).
Kliewer, S.A., "A dozen years of discovery: insights into the physiology and pharmacology of FGF21"; Cell Metab 29, 246-253 (2019).
Stojsavljevic-Shapeski, S., "New Drugs on the Block-Emerging Treatments for Nonalcoholic Steatohepatitis"; J Clin Transl Hepatol 9, 51-59 (2021).
Kong, Y., et al. "FGF21 Reduces Lipid Accumulation in Bovine Hepatocytes by Enhancing Lipid Oxidation and Reducing Lipogenesis via AMPK Signaling"; Animals (Basel) 12, 939-958 (2022).
Liu, C., et al. "Pharmacological Treatment With FGF21 Strongly Improves Plasma Cholesterol Metabolism to Reduce Atherosclerosis"; Cardiovasc Res 118, 489-502 (2022).
Frias, J.P., et al. "BIO89-100 Demonstrated Robust Reductions in Liver Fat and Liver Fat Volume (LFV) by MRI-PDFF, Favorable Tolerability and Potential for Weekly (QW) or Every 2 Weeks (Q2W) Dosing in a Phase 1b/2a Placebo-Controlled, Double-Blind, Multiple Ascending Dose Study in NASH"; J Endocr Soc 5, A5-A6 (2021).
Alkhouri, N., et al. "Pegozafermin Led to Significant Metabolic Benefits, in Addition to Robust Beneficial Effects on the Liver, in an Open-Label Cohort of a Phase 1b/2a Study In Subjects With Non-Alcoholic Steatohepatitis (NASH)". J Hepatol 77, S732 (2022).
Gaich, G., et al. "The Effects of LY2405319, an FGF21 Analog, in Obese Human Subjects With Type 2 Diabetes". Cell Metab 18, 333-340 (2013).
Talukdar, S., et al. "A Long-Acting FGF21 Molecule, PF-05231023, Decreases Body Weight and Improves Lipid Profile in Non-Human Primates and Type 2 Diabetic Subjects". Cell Metab 23, 427-440 (2016).
Charles, E.D., et al. "Pegbelfermin (BMS-986036), pEGylated FGF21, in Patients With Obesity and Type 2 Diabetes: Results From a Randomized Phase 2 Study"; Obesity (Silver Spring) 27, 41-49 (2019).
Kaufman, A., "AKR-001, an Fc-FGF21 Analog, Showed Sustained Pharmacodynamic Effects on Insulin Sensitivity and Lipid Metabolism in Type 2 Diabetes Patients". Cell Rep Med 1, 100057 (2020).
Harrison, S.A., et al. Efruxifermin in non-alcoholic steatohepatitis: a randomized, double-blind, placebo-controlled, phase 2a trial. Nat Med 27, 1262-1271 (2021).
Lin, W., "Advances In Biological Functions and Clinical Studies of FGF21"; Diabetes Metab Syndr Obes 14, 3281-3290 (2021).
Christian, J.B., et al. "Determining triglyceride reductions needed for clinical impact in severe hypertriglyceridemia"; Am J Med 127, 36-44 e31 (2014).
Toth, P.P., "Clinical and Economic Outcomes in a Real-World Population of Patients With Elevated Triglyceride Levels"; Atherosclerosis 237, 790-797 (2014).
Saadatagah, S., et al. "Coronary Heart Disease Risk Ssociated With Primary Isolated Hypertriglyceridemia; a Population-Based Study"; J Am Heart Assoc 10, e019343 (2021).
Wong, N.D., et al. "Residual dyslipidemia among United States adults treated with lipid modifying therapy (data from National Health and Nutrition Examination Survey 2009-2010)"; Am J Cardiol 112, 373-379 (2013).

Das Pradhan, A., et al. "Triglyceride lowering with pemafibrate to reduce cardiovascular risk"; N Engl J Med 387, 1923-1934 (2022).
Rosenson, R.S., et al. "Evinacumab In Severe Hypertriglyceridemia With or Without Lipoprotein Lipase Pathway Mutations: A Phase 2 Randomized Trial". Nat Med 29, 729-737 (2023).
Fazio, S., "Fibrates—The Other Life-Saving Drugs"; US Cardiol 1, 1-6 (2004).
Bhatt, D.L., et al. "Pegozafermin Provides Beneficial Lipid Effects in Subjects With Severe Hypertriglyceridemia Regardless of Background Lipid Therapy Status: An Analysis of the Phase 2 ENTRIGUE Study"; J Am Coll Cardiol 81, 1765-1765 (2023).
European Medicines Agency. "Waylivra Summary of Product Characteristics"; https://www.ema.europa.eu/en/documents/product-information/waylivra-epar-product-information_en.pdf. Mar. 2023.
Pfizer Inc. and Ionis Pharmaceuticals Inc., "Pfizer and Ionis Announce Discontinuation of Vupanorsen Clinical Development Program". https://www.pfizer.com/news/press-release/press-release-detail/pfizer-and-ionis-announce-discontinuation-vupanorsen. Jan. 31, 2022.
Watts, G.F., et al. "Aro-Ang3, An Investigational Rnai Therapeutic, Decreases Serum Angiopoietin-Like Protein 3, Triglycerides, and Cholesterol in Patients With Mixed Dyslipidemia" Circulation 146, e569-e611, p. 104-107, Dec. 19, 2022.
Gaudet, D., et al. "ARO-APOC3, An Investigational Rnai Therapeutic, Decreases Serum Apolipoprotein C3, Triglyceride, and Non-HDL-C Concentrations While Increasing HDL-C In Patients With Severe Hypertriglyceridemia". Circulation 146, e569-e611 p. 107-108, Dec. 19, 2022.
Guo, Y.Y., "Hypertriglyceridemia-Induced Acute Pancreatitis: Progress on Disease Mechanisms and Treatment Modalities"; Discov Med 27, 101-109 (2019).
Fisher, F.M., "Understanding the physiology of FGF21". Annu Rev Physiol 78, 223-241 (2016).
Valdivielso, P., "Current Knowledge of Hypertriglyceridemic Pancreatitis", Eur J Intern Med 25, 689-694 (2014).
Otokozawa, S., et al. "Fasting and Postprandial Apolipoprotein B-48 Levels in Healthy, Obese, and Hyperlipidemic Subjects". Metabolism 58, 1536-1542 (2009).
Taskinen, M.R., et al. "Postprandial metabolism of apolipoproteins B48, B100, C-III, and E in humans with APOC3 loss-of-function mutations"; JCI Insight 7, e160607 (2022).
Loomba, R., "MRI-proton density fat fraction treatment response criteria in nonalcoholic steatohepatitis"; Hepatology 73, 881-883 (2021).
Xu, C., et al. "Influence of Fatty Liver on the Severity and Clinical Outcome in Acute Pancreatitis"; PloS one 10, e0142278 (2015).
Yoon, S.B., et al. "Impact of Fatty Liver on Acute Pancreatitis Severity"; Gastroenterol Res Pract 2017, 4532320 (2017).
Wu, D., et al. "Nonalcoholic Fatty Liver Disease Aggravated the Severity of Acute Pancreatitis in Patients"; Biomed Res Int 2019, 9583790 (2019).
Cuevas-Ramos, D., "C.A. Fibroblast Growth Factor 21 and Browning of White Adipose Tissue"; Front Physiol 10, 37 (2019).
Hui, X., "The FGF21-adiponectin axis in controlling energy and vascular homeostasis"; J Mol Cell Biol 8, 110-119 (2016).
Tanner et al., "Protein Glycosylation in Yeast"; Biochimica et Biophysica. Acta. 906:81-91 (1987).
Hounsell et al, "O-linked Protein Glycosylation Structure and Function". J. 13:19-26 (1996).
Nadano et al. "A Naturally Occurring Deaminated Neuraminic Acid, 3-Deoxy-D-glycero-D-galacto-nonulosonic Acid (KDN)" (1986) J. Biol. Chem. 261:11550-11557.
Varki, "Diversity in the Sialic Acids"; Glycobiology 2:25-40 (1992).
Kumar et al., "Therapeutic Targets, Novel Drugs, and Delivery Systems for Diabetes Associated NAFLD and Liver Fibrosis" Advanced Drug Delivery Reviews, vol. 176, pp. 113888, Sep. 1, 2021.
International Search Report in PCT International Application No. PCT/US2023/069003 mailed Nov. 20, 2023.

* cited by examiner

Median Percent Change in Triglycerides from Baseline at Week 8

Median Percent Change in Triglycerides from Baseline at Week 8

COMPOSITIONS AND METHODS OF TREATMENT FOR SEVERE HYPERTRIGLYCERIDEMIA

RELATED APPLICATIONS

This application claims the benefit of and priority to U.S. Provisional Patent Application Ser. No. 63/355,397, filed Jun. 24, 2022, U.S. Provisional Patent Application Ser. No. 63/399,165, filed Aug. 18, 2022, U.S. Provisional Patent Application Ser. No. 63/373,594, filed Aug. 26, 2022, U.S. Provisional Patent Application Ser. No. 63/386,202, filed Dec. 6, 2022, and U.S. Provisional Patent Application Ser. No. 63/485,641, filed Feb. 17, 2023, the disclosure of each of which is incorporated herein by reference in their entireties.

SEQUENCE LISTING

The instant application contains a Sequence Listing which includes the file entitled 180234-011805.xml, 40,014 bytes in size, which was created Jun. 23, 2023, the contents of which are incorporated herein by reference.

FIELD OF THE INVENTION

Compositions, methods and therapeutic regimens of mutant Fibroblast Growth Factor-21 (FGF-21) peptide conjugates comprising a polyethylene glycol (PEG) moiety attached to a mutant FGF-21 peptide via a glycosyl moiety thereof for the treatment of severe hypertriglyceridemia.

BACKGROUND OF THE INVENTION

FGF-21 is an endocrine hormone that is naturally found as a monomeric non-glycosylated protein. Together with FGF-19 and FGF-23, FGF-21 belongs to the endocrine-acting sub-family while the remaining of the 18 mammalian FGF ligands are grouped into five paracrine-acting sub-families.

SUMMARY OF THE INVENTION

Provided herein are methods for treating severe hypertriglyceridemia in a subject in need thereof. In some embodiments, the methods comprise administering to a subject in need thereof a glycoPEGylated FGF21 analog. In some embodiments, the methods comprise administering to the subject in need thereof a pharmaceutical composition a mutant Fibroblast Growth Factor-21 (FGF-21) peptide conjugate and a pharmaceutically acceptable carrier, wherein the mutant FGF-21 peptide conjugate comprises i) a mutant FGF-21 peptide comprising the amino acid sequence of SEQ ID NO: 2, ii) a glycosyl moiety, and iii) a 20 kDa polyethylene glycol (PEG), wherein the mutant FGF-21 peptide is attached to the glycosyl moiety by a covalent bond between a threonine at amino acid position 173 of SEQ ID NO: 2 and a first site of the glycosyl moiety and wherein the glycosyl moiety is attached to the 20 kDa PEG by a covalent bond between a second site of the glycosyl moiety and the 20 kDa PEG.

Aspects of the disclosure relate to a method of treating severe hypertriglyceridemia (SHTG) in a subject in need thereof, comprising: administering once a week to the subject in need thereof a pharmaceutical composition comprising from 9 mg to 30 mg of a mutant Fibroblast Growth Factor-21 (FGF-21) peptide conjugate and a pharmaceutically acceptable carrier, wherein the mutant FGF-21 peptide conjugate comprises i) a mutant FGF-21 peptide comprising the amino acid sequence of SEQ ID NO: 2, ii) a glycosyl moiety, and iii) a 20 kDa polyethylene glycol (PEG), wherein the mutant FGF-21 peptide is attached to the glycosyl moiety by a covalent bond between a threonine at amino acid position 173 of SEQ ID NO: 2 and a first site of the glycosyl moiety and wherein the glycosyl moiety is attached to the 20 kDa PEG by a covalent bond between a second site of the glycosyl moiety and the 20 kDa PEG, wherein administration of the pharmaceutical composition results in a reduction of triglyceride levels by at least 20% from baseline. In some embodiments, the administration of the pharmaceutical composition results in a median reduction of triglyceride levels by at least 30% from baseline.

In some embodiments, the administration of the pharmaceutical composition results in a median reduction of triglyceride levels by at least 30% from baseline.

In some embodiments, the administration of the pharmaceutical composition results in a median reduction of triglyceride levels by at least 40% from baseline.

In some embodiments, the administration results in normalization of triglyceride levels to less than or equal to 150 mg/dl.

In some embodiments, the administration results in a reduction of non-HDL cholesterol levels by at least 10% from baseline, reduction of apoB levels by at least 10% from baseline, reduction of apoC3 levels by at least 10% from baseline, or a combination thereof.

In some embodiments, the administration results in an increase of the levels of HDL cholesterol by at least 10% from baseline, an increase of the levels of adiponectin by at least 10% from baseline or a combination thereof.

In some embodiments, the administration results in reduction of production of TG-rich lipoproteins.

In some embodiments, the administration results in improvement of clearance of TG-rich lipoproteins.

In some embodiments, the administration results in improvement of insulin sensitivity.

In some embodiments, the subject in need thereof has baseline hepatic steatosis.

In some embodiments, the administration results in reduction greater than 30% in liver fat.

In some embodiments, the method comprising administering the pharmaceutical composition to the subject in need thereof for 8 weeks or more.

In some embodiments, the subject in need thereof is a human subject. In some embodiments, the pharmaceutical composition is administered sub-subcutaneously.

In some embodiments, the subject in need thereof has fasting triglycerides (TG)≥500 mg/dL and ≤2000 mg/dL.

In some embodiments, the pharmaceutical composition comprises 9 mg of the mutant FGF-21 peptide conjugate.

In some embodiments, the pharmaceutical composition comprises from 15 mg to 18 mg of the mutant FGF-21 peptide conjugate.

In some embodiments, the pharmaceutical composition comprises from 27 mg to 30 mg of the mutant FGF-21 peptide conjugate. In some embodiments, the administration results in reduction of alanine transaminase (ALT) marker by at least 10%, reduction of aspartate aminotransferase (AST) marker by at least 10%, median reduction of High-sensitivity C-reactive protein (hsCRP) marker by at least 10% or a combination thereof. In some embodiments, the administration results in reduction of fasting plasma glucose by at least 10%, reduction of HBA1c by at least 0.2% or a combination thereof.

In some embodiments, the subject in need thereof is on background lipid-modifying therapy (LMT). In some embodiments, the LMT comprises statins, prescription fish oil, fibrates or combinations thereof. In some embodiments, the subject in need thereof is on background LMT and wherein the administration results in a reduction of levels of non-HDL cholesterol by at least 10% from baseline. In some embodiments, the subject in need thereof is on background LMT and wherein the administration results in a reduction of levels of apoB cholesterol by at least 10% from baseline.

Aspects of the disclosure relate to a method of treating severe hypertriglyceridemia (SHTG) in a subject in need thereof, comprising: administering once a week to the subject in need thereof a pharmaceutical composition comprising from 27 mg to 30 mg of a mutant Fibroblast Growth Factor-21 (FGF-21) peptide conjugate and a pharmaceutically acceptable carrier, wherein the mutant FGF-21 peptide conjugate comprises i) a mutant FGF-21 peptide comprising the amino acid sequence of SEQ ID NO: 2, ii) a glycosyl moiety, and iii) a 20 kDa polyethylene glycol (PEG), wherein the mutant FGF-21 peptide is attached to the glycosyl moiety by a covalent bond between a threonine at amino acid position 173 of SEQ ID NO: 2 and a first site of the glycosyl moiety and wherein the glycosyl moiety is attached to the 20 kDa PEG by a covalent bond between a second site of the glycosyl moiety and the 20 kDa PEG, wherein administration of the pharmaceutical composition results in a reduction of triglyceride levels by at least 20% from baseline, and wherein administration of the pharmaceutical composition results in one or more of the following: reduction of alanine transaminase (ALT) marker by at least 10% from baseline, reduction of aspartate aminotransferase (AST) marker by at least 10% from baseline, median reduction of High-sensitivity C-reactive protein (hsCRP) marker by at least 10% from baseline, reduction of fasting plasma glucose by at least 10% from baseline, reduction of HBA1c by at least 0.3% from baseline, reduction of non-HDL cholesterol levels by at least 10% from baseline, reduction of apoB levels by at least 10% from baseline, reduction of apoC3 levels by at least 10% from baseline, increase of HDL cholesterol levels by at least 10% from baseline, increase of adiponectin levels by at least 10% from baseline, and reduction greater than 30% in liver fat from baseline.

Other aspects of the disclosure relate to a method of treating severe hypertriglyceridemia (SHTG) in a subject in need thereof, comprising administering once every two weeks to the subject in need thereof a pharmaceutical composition comprising from 31 mg to 44 mg of a mutant Fibroblast Growth Factor-21 (FGF-21) peptide conjugate and a pharmaceutically acceptable carrier, wherein the mutant FGF-21 peptide conjugate comprises i) a mutant FGF-21 peptide comprising the amino acid sequence of SEQ ID NO: 2, ii) a glycosyl moiety, and iii) a 20 kDa polyethylene glycol (PEG), wherein the mutant FGF-21 peptide is attached to the glycosyl moiety by a covalent bond between a threonine at amino acid position 173 of SEQ ID NO: 2 and a first site of the glycosyl moiety and wherein the glycosyl moiety is attached to the 20 kDa PEG by a covalent bond between a second site of the glycosyl moiety and the 20 kDa PEG, wherein administration of the pharmaceutical composition results in a reduction of triglyceride levels by at least 20% from baseline.

In some embodiments, the administration of the pharmaceutical composition results in a median reduction of triglyceride levels by at least 30% from baseline.

In some embodiments, the administration of the pharmaceutical composition results in a median reduction of triglyceride levels by at least 40% from baseline.

In some embodiments, the administration results in normalization of triglyceride levels to less than or equal to 150 mg/dl.

In some embodiments, the administration results in a reduction of non-HDL cholesterol levels by at least 10% from baseline, reduction of apoB levels by at least 10% from baseline, reduction of apoC3 levels by at least 10% from baseline, or a combination thereof.

In some embodiments, the administration results in an increase of the levels of HDL cholesterol by at least 10% from baseline, an increase of the levels of adiponectin by at least 10% from baseline or a combination thereof.

In some embodiments, the administration results in reduction of production of TG-rich lipoproteins.

In some embodiments, the administration results in improvement of clearance of TG-rich lipoproteins.

In some embodiments, the administration results in improvement of insulin sensitivity.

In some embodiments, the subject in need thereof has baseline hepatic steatosis.

In some embodiments, the administration results in reduction greater than 30% in liver fat.

In some embodiments, the method comprising administering the pharmaceutical composition to the subject in need thereof for 8 weeks or more.

In some embodiments, the subject in need thereof is a human subject. In some embodiments, the pharmaceutical composition is administered sub-subcutaneously.

In some embodiments, the subject in need thereof has fasting triglycerides (TG)≥500 mg/dL and ≤2000 mg/dL.

In some embodiments, the pharmaceutical composition comprises from 36 mg to 44 mg of the mutant FGF-21 peptide conjugate. In some embodiments, the administration results in median reduction of hsCRP marker by at least 10%.

In some embodiments, the subject in need thereof is on background lipid-modifying therapy (LMT). In some embodiments, the LMT comprises statins, prescription fish oil, fibrates or combinations thereof. In some embodiments, the subject in need thereof is on background LMT and wherein the administration results in a reduction of levels of non-HDL cholesterol by at least 10% from baseline. In some embodiments, the subject in need thereof is on background LMT and wherein the administration results in a reduction of levels of apoB cholesterol by at least 10% from baseline.

Aspects of the disclosure relate to a method of treating severe hypertriglyceridemia (SHTG) in a subject in need thereof, comprising: administering once every two weeks to the subject in need thereof a pharmaceutical composition comprising from 36 mg to 44 mg of a mutant Fibroblast Growth Factor-21 (FGF-21) peptide conjugate and a pharmaceutically acceptable carrier, wherein the mutant FGF-21 peptide conjugate comprises i) a mutant FGF-21 peptide comprising the amino acid sequence of SEQ ID NO: 2, ii) a glycosyl moiety, and iii) a 20 kDa polyethylene glycol (PEG), wherein the mutant FGF-21 peptide is attached to the glycosyl moiety by a covalent bond between a threonine at amino acid position 173 of SEQ ID NO: 2 and a first site of the glycosyl moiety and wherein the glycosyl moiety is attached to the 20 kDa PEG by a covalent bond between a second site of the glycosyl moiety and the 20 kDa PEG, wherein administration of the pharmaceutical composition results in a reduction of triglyceride levels by at least 20% from baseline, and wherein administration of the pharmaceutical composition results in one or more of the following: median reduction of High-sensitivity C-reactive protein (hsCRP) marker by at least 10% from baseline, reduction of non-HDL cholesterol levels by at least 10% from baseline, reduction of apoB levels by at least 10% from baseline, reduction of apoC3 levels by at least 10% from baseline, increase of HDL cholesterol levels by at least 10% from baseline, increase of adiponectin levels by at least 10% from baseline, and reduction greater than 30% in liver fat from baseline.

In some embodiments, the glycosyl moiety of the mutant FGF-21 peptide conjugate comprises at least one of an N-acetylgalactosamine (GalNAc) residue, a galactose (Gal) residue, a sialic acid (Sia) residue, a 5-amine analogue of a Sia residue, a mannose (Man) residue, mannosamine, a glucose (Glc) residue, an N-acetylglucosamine (GlcNAc) residue, a fucose residue, a xylose residue, or a combination thereof.

In some embodiments, the glycosyl moiety of the mutant FGF-21 peptide conjugate comprises at least one N-acetylgalactosamine (GalNAc) residue, at least one galactose (Gal) residue, at least one sialic acid (Sia) residue, or a combination thereof. In some embodiments, the at least one Sia residue is a nine-carbon carboxylated sugar. In some embodiments, the at least one Sia residue is N-acetylneuraminic acid (2-keto-5-acetamido-3,5-dideoxy-D-glycero-D-galactononulopyranos-1-onic acid (Neu5Ac), N-glycolylneuraminic acid (Neu5Gc), 2-keto-3-deoxy-nonulosonic acid (KDN), or a 9-substituted sialic acid. In some embodiments, the 9-substituted sialic acid is 9-O-lactyl-Neu5Ac, 9-O-acetyl-Neu5Ac, 9-deoxy-9-fluoro-Neu5Ac, or 9-azido-9-deoxy-Neu5Ac.

In some embodiments, the glycosyl moiety of the mutant FGF-21 peptide conjugate comprises the structure -GalNAc-Sia-.

In some embodiments, the 20 kDa PEG moiety of the mutant FGF-21 peptide conjugate is attached to the glycosyl moiety by a covalent bond to a linker, wherein the linker comprises at least one amino acid residue. In some embodiments, the at least one amino acid residue is a glycine (Gly).

In some embodiments, the mutant FGF-21 peptide conjugate comprises the structure -GalNAc-Sia-Gly-PEG (20 kDa).

In some embodiments, the 20 kDa PEG of the FGF-21 peptide conjugate is a linear or branched PEG. In some embodiments, the 20 kDa PEG is a 20 kDa methoxy-PEG.

In some embodiments, the mutant FGF-21 peptide conjugate comprises the structure:

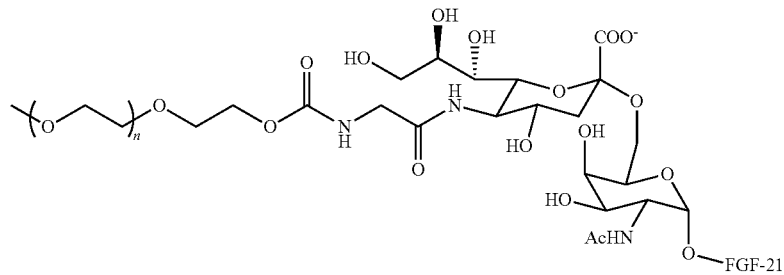

wherein n is an integer selected from 450 to 460.

Aspects of the disclosure relates to the use of a pharmaceutical composition for the treatment of severe hypertriglyceridemia (SHTG), the pharmaceutical composition comprising from 9 mg to 30 mg of a mutant Fibroblast Growth Factor-21 (FGF-21) peptide conjugate and a pharmaceutically acceptable carrier, wherein the pharmaceutical composition is administered once every week, wherein the mutant FGF-21 peptide conjugate comprises i) a mutant FGF-21 peptide comprising the amino acid sequence of SEQ ID NO: 2, ii) a glycosyl moiety, and iii) a 20 kDa polyethylene glycol (PEG), wherein the mutant FGF-21 peptide is attached to the glycosyl moiety by a covalent bond between a threonine at amino acid position 173 of SEQ ID NO: 2 and a first site of the glycosyl moiety and wherein the glycosyl moiety is attached to the 20 kDa PEG by a covalent bond between a second site of the glycosyl moiety and the 20 kDa PEG.

Aspects of the disclosure relates to the use of a pharmaceutical composition for reducing triglyceride levels by at least 20% from baseline in a subject having severe hypertriglyceridemia (SHTG), the pharmaceutical composition comprising from 9 mg to 30 mg of a mutant Fibroblast Growth Factor-21 (FGF-21) peptide conjugate and a pharmaceutically acceptable carrier, wherein the pharmaceutical composition is administered once a week, wherein the mutant FGF-21 peptide conjugate comprises i) a mutant FGF-21 peptide comprising the amino acid sequence of SEQ ID NO: 2, ii) a glycosyl moiety, and iii) a 20 kDa polyethylene glycol (PEG), wherein the mutant FGF-21 peptide is attached to the glycosyl moiety by a covalent bond between a threonine at amino acid position 173 of SEQ ID NO: 2 and a first site of the glycosyl moiety and wherein the glycosyl moiety is attached to the 20 kDa PEG by a covalent bond between a second site of the glycosyl moiety and the 20 kDa PEG. In some embodiments, the pharmaceutical composition reduces triglyceride levels by at least 30% or at least 40% from baseline in a subject having severe hypertriglyceridemia.

In some embodiments, the pharmaceutical composition comprises from 27 mg to 30 mg of a mutant Fibroblast Growth Factor-21 (FGF-21) peptide conjugate and a pharmaceutically acceptable carrier.

Aspects of the disclosure relates to the use of a pharmaceutical composition for the treatment of severe hypertriglyceridemia (SHTG), the pharmaceutical composition comprising from 31 mg to 44 mg of a mutant Fibroblast Growth Factor-21 (FGF-21) peptide conjugate and a pharmaceutically acceptable carrier, wherein the pharmaceutical composition is administered once every two weeks, wherein the mutant FGF-21 peptide conjugate comprises i) a mutant FGF-21 peptide comprising the amino acid sequence of SEQ ID NO: 2, ii) a glycosyl moiety, and iii) a 20 kDa polyethylene glycol (PEG), wherein the mutant FGF-21 peptide is attached to the glycosyl moiety by a covalent bond between a threonine at amino acid position 173 of SEQ ID NO: 2 and a first site of the glycosyl moiety and wherein the glycosyl moiety is attached to the 20 kDa PEG by a covalent bond between a second site of the glycosyl moiety and the 20 kDa PEG.

Aspects of the disclosure relates to the use of a pharmaceutical composition for reducing triglyceride levels by at least 20% from baseline in a subject having severe hypertriglyceridemia (SHTG), the pharmaceutical composition comprising from 31 mg to 44 mg of a mutant Fibroblast Growth Factor-21 (FGF-21) peptide conjugate and a pharmaceutically acceptable carrier, wherein the pharmaceutical composition is administered once every two weeks, wherein the mutant FGF-21 peptide conjugate comprises i) a mutant FGF-21 peptide comprising the amino acid sequence of SEQ ID NO: 2, ii) a glycosyl moiety, and iii) a 20 kDa polyethylene glycol (PEG), wherein the mutant FGF-21 peptide is attached to the glycosyl moiety by a covalent bond between a threonine at amino acid position 173 of SEQ ID NO: 2 and a first site of the glycosyl moiety and wherein the glycosyl moiety is attached to the 20 kDa PEG by a covalent bond between a second site of the glycosyl moiety and the 20 kDa PEG.

In some embodiments, the pharmaceutical composition reduces triglyceride levels by at least 30% or at least 40% from baseline in a subject having severe hypertriglyceridemia.

In some embodiments, the pharmaceutical composition comprises from 36 mg to 44 mg of a mutant Fibroblast Growth Factor-21 (FGF-21) peptide conjugate and a pharmaceutically acceptable carrier.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A: Primary endpoint—median percent change in TG from baseline to week 8. FIG. 1B: Proportion of subjects who achieved TG response of <500 mg/dL, <150 mg/dL, or ≥50% reduction from baseline to week 8. FIG. 1C: TG subgroup analysis among subjects not on background lipid-modifying therapy. FIG. 1D: TG subgroup analysis among subjects on background lipid-modifying therapy. FIG. 1E: TG subgroup analysis among subjects without T2DM. FIG. 1F: TG subgroup analysis among subjects with T2DM. Data based on full analysis set population and analyzed via van Elteren Test for pooled pegozafermin groups and Wilcoxon Rank-sum Test for individual pegozafermin dose groups. QW, once-weekly; Q2W, once-every two weeks.

FIG. 3A: LS mean (+/−SE) percent change from baseline to week 8 in liver fat fraction assessed by MRI-PDFF. FIG. 3B: MRI-proton density fat fraction (MRI-PDFF) images depicting changes in liver fat fraction from representative subjects with baseline liver fat fraction >25%. FIG. 3C: Proportion of subjects who achieved liver fat normalization (i.e., <5% by MRI-PDFF), ≥30% or ≥50% relative reduction in liver fat after 8 weeks. FIG. 3D: LS mean (+/−SE) percent change in adiponectin. FIG. 3E: Median fasting insulin among subjects not taking concomitant insulin. Data based on full analysis set population and analyzed via MMRM or van Elteren test for pooled pegozafermin groups and Wilcoxon rank-sum test for individual pegozafermin dose groups. Images in FIG. 3B were generated using a common colorscale for all subjects. MRI-PDFF, magnetic resonance imaging—whole liver proton density fat fraction; QW, once-weekly; Q2W, once-every two weeks.

FIG. 16A: Median percent change in TG from baseline to week 8 (the primary endpoint), FIG. 16B: Proportion of subjects who achieved TG responses of <500 mg/dL, <150 mg/dL, or a ≥50% reduction from baseline to week 8. TG subgroup analysis among subjects (not on background lipid-modifying therapy (FIG. 16C), on background lipid-modifying therapy (FIG. 16D), without T2DM (FIG. 16E), and with T2DM (FIG. 16F). Data are based on full analysis set population (defined as all randomized subjects who received at least one dose of study treatment, had baseline and at least one post-baseline TG value) and analyzed using the van Elteren Test for pooled pegozafermin groups and the Wilcoxon Rank-sum Test for individual pegozafermin dose groups. N represents independent subjects examined at baseline and 4 post-baseline timepoints for TG related graphs. All p-values are two sided and based on comparison to the placebo arm. QW, once-weekly; Q2W, once-every two weeks; PBO, placebo; PGZ, pegozafermin.

FIG. 18A: Least Square (LS) mean (+/− SE) percent change from baseline to week 8 in liver fat fraction assessed by MRI-PDFF. FIG. 18B: MRI-PDFF images depicting changes in liver fat fraction from representative subjects with elevated baseline liver fat fraction defined as >25%. FIG. 18C: Proportion of subjects who achieved liver fat normalization (i.e., <5% by MRI-PDFF), ≥30% or ≥50% relative reduction in liver fat after 8 weeks. Data are based on full analysis set population (defined as all randomized subjects who received at least one dose of study treatment, had baseline and at least one post-baseline TG) and analyzed using MMRM or the van Elteren test for pooled pegozafermin groups and Wilcoxon rank-sum test for individual pegozafermin dose groups. N represents independent subjects examined at baseline and 1 post-baseline timepoint for liver fat graphs. All individual MRI-PDFF images in FIG. 19B were generated as 384×288 mm and color corrected to a common color-scale to allow direct comparison across images. MRI-PDFF, magnetic resonance imaging—whole liver proton density fat fraction; QW, once-weekly; Q2W, once-every two weeks, PBO, placebo; PGZ, pegozafermin.

DETAILED DESCRIPTION

Definitions

Figure 1A:
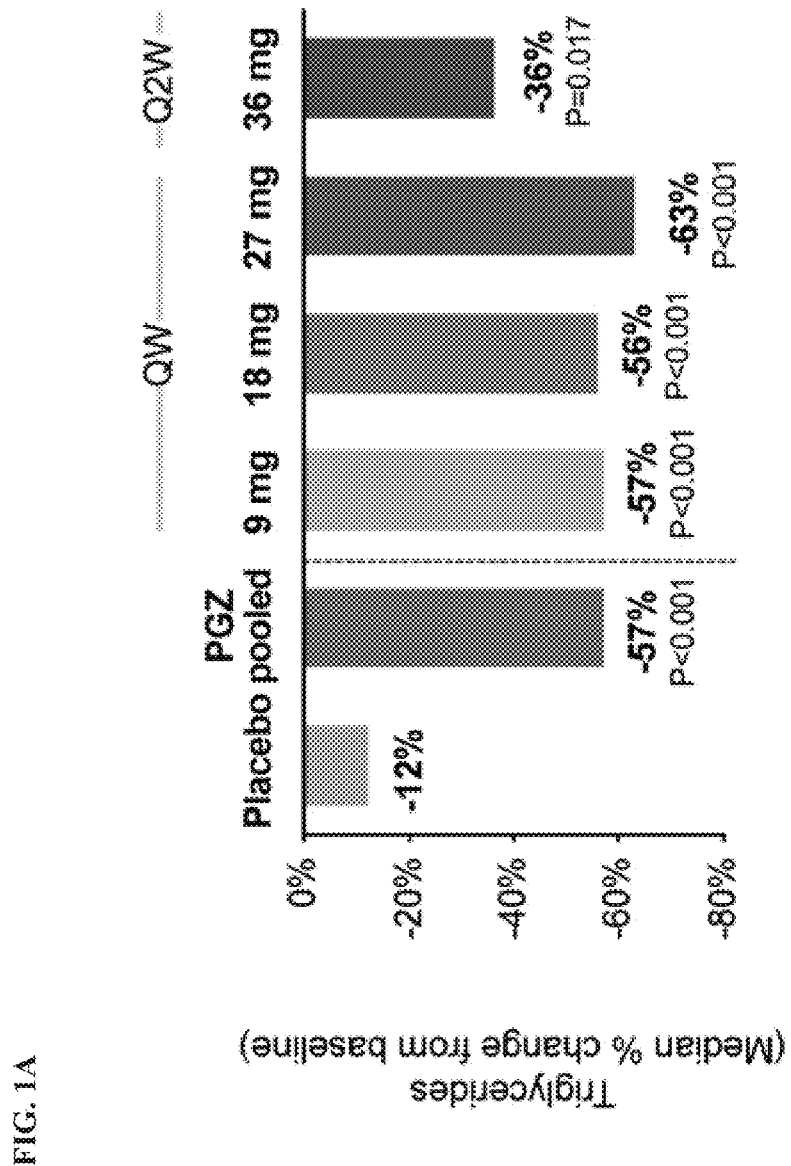
FIGS. 1A-1F are graphs showing the effect of pegozafermin on serum triglycerides.

For the sake of clarity and readability, the following definitions are provided. Any technical feature mentioned for these definitions may be read on each and every embodiment of the invention. Additional definitions and explanations may be specifically provided in the context of these embodiments. Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization are those well-known and commonly employed in the art. Standard techniques are used for nucleic acid and peptide synthesis. The techniques and procedures are generally performed according to conventional methods in the art and various general references (e.g., Sambrook et al., 1989, Molecular Cloning: A Laboratory Manual, 2d ed. Cold Spring Harbor Laboratory Press, Cold Spring Harbor, NY), which are provided throughout this document.

Enzyme: Enzymes are catalytically active biomolecules that perform biochemical reactions such as the transfer of glycosyl moieties or modified glycosyl moieties from the respective glycosyl donors to an amino acid of FGF-21 or to another glycosyl moiety attached to the peptide.

Protein: A protein typically comprises one or more peptides or polypeptides. A protein is typically folded into a 3-dimensional form, which may be required for the protein to exert its biological function. The sequence of a protein or peptide is typically understood to be in the order, i.e. the succession of its amino acids.

Recombinant protein: The term "recombinant protein" refers to proteins produced in a heterologous system, that is, in an organism that naturally does not produce such a protein, or a variant of such a protein, i.e. the protein or peptide is "recombinantly produced". Typically, the heterologous systems used in the art to produce recombinant proteins are bacteria (e.g., *Escherichia (E.) coli*), yeast (e.g., *Saccharomyces (S.) cerevisiae*) or certain mammalian cell culture lines.

Expression host: An expression host denotes an organism which is used for recombinant protein production. General expression hosts are bacteria, such as *E. coli*, yeasts, such as *Saccharomyces cerevisiae* or *Pichia pastoris*, or also mammal cells, such as human cells.

RNA, mRNA: RNA is the usual abbreviation for ribonucleic acid. It is a nucleic acid molecule, i.e. a polymer consisting of nucleotides. These nucleotides are usually adenosine-monophosphate, uridine-monophosphate, guanosine-monophosphate and cytidine-monophosphate monomers which are connected to each other along a so-called backbone. The backbone is formed by phosphodiester bonds between the sugar, i.e. ribose, of a first and a phosphate moiety of a second, adjacent monomer. The specific succession of the monomers is called the RNA sequence.

DNA: DNA is the usual abbreviation for deoxyribonucleic acid. It is a nucleic acid molecule, i.e. a polymer consisting of nucleotide monomers. These nucleotides are usually deoxy-adenosine-monophosphate, deoxy-thymidine-monophosphate, deoxy-guanosine-monophosphate and deoxy-cytidine-monophosphate monomers which are—by themselves—composed of a sugar moiety (deoxyribose), a base moiety and a phosphate moiety, and polymerized by a characteristic backbone structure. The backbone structure is, typically, formed by phosphodiester bonds between the sugar moiety of the nucleotide, i.e. deoxyribose, of a first and a phosphate moiety of a second, adjacent monomer. The specific order of the monomers, i.e. the order of the bases linked to the sugar/phosphate-backbone, is called the DNA-sequence. DNA may be single-stranded or double-stranded. In the double stranded form, the nucleotides of the first strand typically hybridize with the nucleotides of the second strand, e.g. by A/T-base-pairing and G/C-base-pairing.

Sequence of a nucleic acid molecule/nucleic acid sequence: The sequence of a nucleic acid molecule is typically understood to be in the particular and individual order, i.e. the succession of its nucleotides.

Sequence of amino acid molecules/amino acid sequence: The sequence of a protein or peptide is typically understood to be in the order, i.e. the succession of its amino acids.

Sequence identity: Two or more sequences are identical if they exhibit the same length and order of nucleotides or amino acids. The percentage of identity typically describes the extent, to which two sequences are identical, i.e. it typically describes the percentage of nucleotides that correspond in their sequence position to identical nucleotides of a reference sequence, such as a native or wild type sequence. For the determination of the degree of identity, the sequences to be compared are considered to exhibit the same length, i.e. the length of the longest sequence of the sequences to be compared. This means that a first sequence consisting of 8 nucleotides/amino acids is 80% identical to a second sequence consisting of 10 nucleotides/amino acids comprising the first sequence. In other words, in the context of the present invention, identity of sequences particularly relates to the percentage of nucleotides/amino acids of a sequence, which have the same position in two or more sequences having the same length. Gaps are usually regarded as non-identical positions, irrespective of their actual position in an alignment.

Newly introduced amino acids: "Newly introduced amino acids" denote amino acids which are newly introduced into an amino acid sequence in comparison to a native/wild type amino acid sequence. Usually by mutagenesis, the native amino acid sequence is changed in order to have a certain amino acid side chain at a desired position within the amino acid sequence. In the present invention, in particular the amino acid threonine is newly introduced into the amino acid sequence on the C-terminal side adjacent to a proline residue.

Functional group: The term is to be understood according to the skilled person's general understanding in the art and denotes a chemical moiety which is present on a molecule, in particular on the peptide or amino acid of the peptide or glycosyl residue attached to the peptide, and which may participate in a covalent or non-covalent bond to another chemical molecule, i.e. which allows e.g. the attachment of a glycosyl residue or PEG.

Native amino acid sequence: The term is to be understood according to the skilled person's general understanding in the art and denotes the amino acid sequence in the form of its occurrence in nature without any mutation or amino acid amendment by man. It is also called "wild-type sequence". "Native FGF-21" or "wild-type FGF-21" denotes FGF-21 having the amino acid sequence as it occurs in nature, such as the (not mutated) amino acid sequence of human FGF-21 as depicted in SEQ ID NO: 1. The presence or absence of an N-terminal methionine, which depends on the used expression host, usually does not change the status of a protein being considered as having its natural or native/wild-type sequence.

Mutated: The term is to be understood according to the skilled person's general understanding in the art. An amino acid sequence is called "mutated" if it contains at least one additional, deleted or exchanged amino acid in its amino acid sequence in comparison to its natural or native amino acid sequence, i.e. if it contains an amino acid mutation. Mutated proteins are also called mutants. In the present invention, a mutated FGF-21 peptide is particularly a peptide having an amino acid exchange adjacent to a proline residue on the C-terminal side of the proline residue. Thereby a consensus sequence for O-linked glycosylation is introduced into FGF-21 such that the mutant FGF-21 peptide comprises a newly introduced O-linked glycosylation side. Amino acid exchanges are typically denoted as follows: $S^{172}T$ which means that the amino acid serine at position 172, such as in the amino acid sequence of SEQ ID NO: 1, is exchanged by the amino acid threonine.

Pharmaceutically effective amount: A pharmaceutically effective amount in the context of the invention is typically understood to be an amount that is sufficient to induce a pharmaceutical effect.

Therapy/treatment: The term "therapy" refers to "treating" or "treatment" of a disease or condition, inhibiting the disease (slowing or arresting its development), providing relief from the symptoms or side-effects of the disease (including palliative treatment), and relieving the disease (causing regression of the disease).

Therapeutically effective amount: is an amount of a compound that is sufficient to treat a disease or condition, inhibit the disease or condition, provide relief from symptoms or side-effects of the disease, and/or cause regression of the disease or condition.

Half-life: The term "half-life", as used herein in the context of administering a mutant FGF-21 peptide and/or conjugate thereof, is defined as the time required for the plasma concentration of a drug, i.e. of the mutant FGF-21 peptide and/or conjugate, in a subject to be reduced by one half.

O-linked glycosylation: "O-linked glycosylation" takes place at serine or threonine residues (Tanner et al., Biochim. Biophys. Acta. 906:81-91 (1987); and Hounsell et al, Glycoconj. J. 13:19-26 (1996)). In the present invention, O-linked glycosylation sites, which are amino acid motifs in the amino acid sequence of a peptide which are recognized by glycosyl transferases as attachment points for glycosyl residues, include the amino acid motif proline-threonine (PT) not present in the native/wild-type amino acid sequence. In particular, the threonine residue is newly introduced adjacent to a proline and on the C-terminal side of a proline residue. The glycosyl moiety is then attached to the —OH group of the threonine residue by the glycosyl transferase.

Newly introduced O-linked glycosylation side: "Newly introduced O-linked glycosylation side" denotes an O-linked glycosylation side which did not exist in the native or wild-type FGF-21 before introducing a threonine adjacent to and on the C-terminal side of a proline residue as described herein.

Adjacent: Adjacent denotes the amino acid immediately next to another amino acid in the amino acid sequence, either on the N-terminal or on the C-terminal side of the respective amino acid. In the present invention, e.g. the newly introduced threonine residue is adjacent to a proline residue on the C-terminal side of a proline residue.

Glycosyl moiety: A glycosyl moiety is a moiety consisting of one or more, identical or different glycosyl residues which links the mutant FGF-21 peptide to a polyethylene glycol (PEG), thereby forming a conjugate comprising a peptide, glycosyl moiety and PEG. The glycosyl moiety can be a mono-, di-, tri-, or oligoglycosyl moiety. The glycosyl moiety may comprise one or more sialic acid residues, one or more N-acetylgalactosamine (GalNAc) residues, one or more galactose (Gal) residues and others. The glycosyl moiety may be modified, such as with a PEG or methoxy-PEG (m-PEG), an alkyl derivative of PEG.

Glycoconjugation: "Glycoconjugation", as used herein, refers to the enzymatically mediated conjugation of a PEG-modified glycosyl moiety to an amino acid or glycosyl residue of a (poly)peptide, e.g. a mutant FGF-21 of the present invention. A subgenus of "glycoconjugation" is "glyco-PEGylation" in which the modifying group of the modified glycosyl moiety is PEG or m-PEG. The PEG may be linear or branched. Typically, a branched PEG has a central branch core moiety and a plurality of linear polymer chains linked to the central branch core. PEG is commonly used in branched forms that can be prepared by addition of ethylene oxide to various polyols, such as glycerol, pentaerythritol and sorbitol. The central branch moiety can also be derived from several amino acids, such as lysine. The branched PEG can be represented in general form as R(-PEG-OX)$_m$ in which R represents the core moiety, such as glycerol or pentaerythritol, X represents a capping group or an end group, and m represents the number of arms. The terms "glyco-PEG" and "glycosyl-PEG" are used interchangeably and denote a chemical moiety consisting of PEG or methoxy-PEG (mPEG or m-PEG), one or more glycosyl residues (or glycosyl moieties), and optionally a linker between PEG/methoxy-PEG and the glycosyl moieties, such as an amino acid, e.g. glycine. An example of a glycosyl-PEG/glyco-PEG moiety is PEG-sialic acid (PEG-Sia). It should be noted that the terms "glyco-PEG" and "glycosyl-PEG" as well as "PEG-sialic acid" and "PEG-Sia" as well as similar terms for glyco-PEG moieties may or may not include a linker between PEG and the glycosyl moiety or moieties, i.e. "PEG-sialic acid" encompasses e.g. PEG-sialic acid as well as PEG-Gly-sialic acid as well as mPEG-Gly-sialic acid.

Sequence motif: A sequence motif denotes a short amino acid sequence, such as that comprising only two amino acids, which is present at any possible position in a longer amino acid sequence, such as in the amino acid sequence of human FGF-21. Sequence motifs are e.g. denoted as P' 72 T which means that the proline at position 172 is followed C-terminally immediately by a threonine residue.

Sialic acid: The term "sialic acid" or "Sia" refers to any member of a family of nine-carbon carboxylated sugars. The most common member of the sialic acid family is N-acetyl-neuraminic acid (2-keto-5-acetamido-3,5-dideoxy-D-glycero-D-galactononulopyranos-1-onic acid (often abbreviated as Neu5Ac, NeuAc, or NANA). A second member of the family is N-glycolylneuraminic acid (Neu5Gc or NeuGc), in which the N-acetyl group of NeuAc is hydroxylated. A third sialic acid family member is 2-keto-3-deoxy-nonulosonic acid (KDN) (Nadano et al. (1986) J. Biol. Chem. 261:11550-11557). Also included are 9-substituted sialic acids such as a 9-0-$C_1$-$C_6$ acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac. For review of the sialic acid family, see e.g. Varki, Glycobiology 2:25-40 (1992)).

Pharmaceutically acceptable excipient: "Pharmaceutically acceptable" excipient includes any material, which when combined with the mutant FGF-21 peptide conjugate of the invention retains the conjugates' activity and is non-reactive with a subject's immune systems. Examples include, but are not limited to, any of the standard pharmaceutical excipients such as a phosphate buffered saline solution, water, salts, emulsions such as oil/water emulsion, and various types of wetting agents.

Pharmaceutical container: A "pharmaceutical container" is a container which is suitable for carrying a pharmaceutical composition and typically made of an inert material and sterile.

Administering: The term "administering" means oral administration, inhalation, administration as a suppository, topical contact, intravenous, intraperitoneal, intramuscular, intralesional, intranasal or subcutaneous administration, or the implantation of a slow-release device e.g., a mini-osmotic pump, to the subject. Administration is by any route including parenteral, and transmucosal (e.g. oral, nasal, vaginal, rectal, or transdermal). Parenteral administration includes e.g. intravenous, intramuscular, intraarteriole, intradermal, subcutaneous, intraperitoneal, intraventricular and intracranial. Other modes of delivery include, but are not limited to, the use of liposomal formulations, intravenous infusion, transdermal patches, etc.

Fibroblast growth factor 21 (FGF21) is an endogenous hormone regulating lipid and glucose metabolism and energy expenditure.

Provided herein are for treating severe hypertriglyceridemia in a subject in need thereof. In some embodiments, the methods comprise administering to a subject in need thereof a glycoPEGylated FGF21 analog (also referred herein as Pegozafermin (PGZ)), designed to have a longer half-life than native FGF21. Provided herein are methods of treating severe hypertriglyceridemia in a subject in need thereof. In some embodiments, the methods comprise administering to the subject in need thereof a pharmaceutical composition a mutant Fibroblast Growth Factor-21 (FGF-21) peptide conjugate and a pharmaceutically acceptable carrier, wherein the mutant FGF-21 peptide conjugate comprises i) a mutant FGF-21 peptide comprising the amino acid sequence of SEQ ID NO: 2, ii) a glycosyl moiety, and iii) a 20 kDa polyethylene glycol (PEG), wherein the mutant FGF-21 peptide is attached to the glycosyl moiety by a covalent bond between a threonine at amino acid position 173 of SEQ ID NO: 2 and a first site of the glycosyl moiety and wherein the glycosyl moiety is attached to the 20 kDa PEG by a covalent bond between a second site of the glycosyl moiety and the 20 kDa PEG.

Mutant FGF-21 Peptides and Conjugates Thereof

Natural FGF-21 has a comparatively short half-life in vivo, with a reported circulating half-life ranging from 0.5 to 4 hours in rodents and non-human primates, which limits its clinical applicability. The half-life of recombinant human FGF-21 is 1-2 hours. To improve pharmacokinetic properties of FGF-21, various half-life extension strategies have been developed.

See also WO2019/043457, the entire content of which is incorporated herein in its entirety.

Some aspects of the disclosure relate to FGF-21 conjugates for use in the treatment of severe hypertriglyceridemia. According to some embodiments, the methods comprise administering to a subject in need thereof a glycoPEGylated FGF21 analog (also referred herein as Pegozafermin (PGZ)), designed to have a longer half-life than native FGF21. Provided herein are methods of treating severe hypertriglyceridemia in a subject in need thereof. In some embodiments, the methods comprise administering to the subject in need thereof a pharmaceutical composition a mutant Fibroblast Growth Factor-21 (FGF-21) peptide conjugate and a pharmaceutically acceptable carrier, wherein the mutant FGF-21 peptide conjugate comprises i) a mutant FGF-21 peptide comprising the amino acid sequence of SEQ ID NO: 2, ii) a glycosyl moiety, and iii) a 20 kDa polyethylene glycol (PEG), wherein the mutant FGF-21 peptide is attached to the glycosyl moiety by a covalent bond between a threonine at amino acid position 173 of SEQ ID NO: 2 and a first site of the glycosyl moiety and wherein the glycosyl moiety is attached to the 20 kDa PEG by a covalent bond between a second site of the glycosyl moiety and the 20 kDa PEG.

In some embodiments, the 20 kDa PEG moiety is attached to the glycosyl moiety by a covalent bond to a linker, wherein the linker comprises at least one amino acid residue. In some embodiments, the at least one amino acid residue is a glycine (Gly). In some embodiments, the mutant FGF-21 peptide conjugate comprises the structure -GalNAc-Sia-Gly-PEG (20 kDa). In some embodiments, the mutant FGF-21 peptide conjugate comprises the structure:

PEGylation

In glycoPEGylation, a PEG moiety may be transferred to an amino acid or glycosyl residue attached to an amino acid of the protein or peptide using a glycosyltransferase. The general final structure is protein—glycosyl moiety—optional further linker—PEG. A more particular final structure is protein—(N-, C- or internal) amino acid of the protein—one or more glycosyl residues—optional linker (e.g., amino acid linker)—linear or branched PEG moiety of various lengths, wherein the glycosyl moiety may comprise one or more glycosyl residues. The one or more glycosyl residues comprising at least part of the structure linking the protein to the PEG moiety may be any possible glycosyl residue. A diverse array of methods for glycoPEGylating proteins are known in the art and are described in detail herein below.

In some embodiments, Fibroblast Growth Factor-21 (FGF-21) peptide conjugates comprise:
i) a mutant FGF-21 peptide comprising at least one threonine (T) residue adjacent to at least one proline (P) residue on the C-terminal side of said at least one proline residue, thereby forming at least one O-linked glycosylation site which does not exist in the corresponding native FGF-21, wherein the corresponding native FGF-21 has an amino acid sequence that is at least 95% identical to SEQ ID NO: 1, and
ii) a 20 kDa polyethylene glycol (PEG), wherein said 20 kDa PEG is covalently attached to said mutant FGF-21 peptide at said at least one threonine residue via at least one glycosyl moiety.

In a particular embodiment, the mutant FGF-21 peptide conjugate comprises a mutant FGF-21 peptide comprising the amino acid sequence PT. In particular embodiments thereof, the mutant FGF-21 peptide comprises at least one amino acid sequence selected from the group consisting of P172T, P156T, PST, P3T, P9T, PSOT, P61T, P79T, P91T, P116T, P129T, P131T, P134T, P139T, P141T, P144T, P145T, P148T, P150T, P151T, P158T, P159T, P166T, P178T

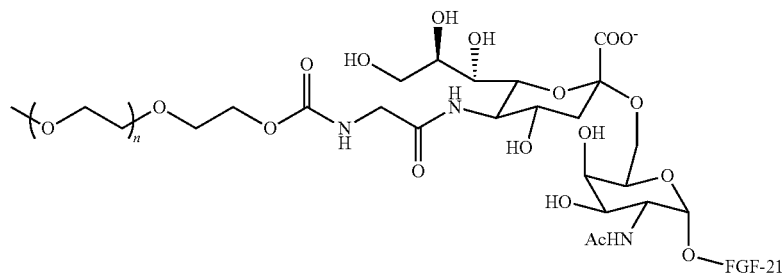

wherein n is an integer selected from 450 to 460.

In some embodiments, the 20 kDa PEG is a linear PEG. In other embodiments, the 20 kDa PEG is a branched PEG. In some embodiments, the 20 kDa PEG is a 20 kDa methoxy-PEG.

In some embodiments, the subject is a human subject.

In some embodiments, the pharmaceutical composition is administered sub-subcutaneously.

In some embodiments, the liquid pharmaceutical composition comprises 9-48 mg/ml FGF-21 peptide conjugate, for example 9 mg/ml, 18 mg/ml, 20 mg/ml, 28 mg/ml, 30 mg/ml, 36 mg/ml, 42 mg/ml, 44 mg/ml, 48 mg/ml.

See U.S. Pat. Nos. 10,407,479, 10,874,714, 11,596,669 and 11,596,669, which are incorporated herein by reference in its their entireties.

and combinations thereof, wherein the positions of proline and threonine are based on the amino acid sequence as depicted in SEQ ID NO: 1. In a more particular embodiment, the mutant FGF-21 peptide comprises at least one amino acid sequence selected from the group consisting of P172T, P156T, PST and combinations thereof, particularly consisting of P172T, P156T and combinations thereof, wherein the positions of proline and threonine are based on the amino acid sequence as depicted in SEQ ID NO: 1. In a still more particular embodiment, the proline residue is located between amino acid 145 and the C-terminus of the mutant FGF-21 peptide, wherein the position of amino acid 145 is based on the amino acid sequence as depicted in SEQ ID NO: 1.

In another particular embodiment, the mutant FGF-21 peptide comprises the amino acid sequence P172T, wherein the positions of proline and threonine are based on the amino acid sequence as depicted in SEQ ID NO: 1.

In another particular embodiment, the mutant FGF-21 peptide comprises the mutations S173T and R176A, wherein the positions of the amino acids S and R are based on the amino acid sequence as depicted in SEQ ID NO: 1, particularly the mutant FGF-21 peptide comprises the amino acid sequence as depicted in SEQ ID NO: 2.

In another particular embodiment, the mutant FGF-21 peptide comprises the mutation Q157T, wherein the position of the amino acid Q is based on the amino acid sequence as depicted in SEQ ID NO: 1, particularly the mutant FGF-21 peptide comprises the amino acid sequence as depicted in SEQ ID NO: 4.

In another particular embodiment, the mutant FGF-21 peptide comprises the mutation D6T, wherein the position of the amino acid D is based on the amino acid sequence as depicted in SEQ ID NO: 1, particularly the mutant FGF-21 peptide comprises the amino acid sequence as depicted in SEQ ID NO: 5.

In other particular embodiments, the mutant FGF-21 peptide comprises an amino acid sequence selected from the group consisting of SEQ ID NOs: 2 to 28, particularly an amino acid sequence selected from the group consisting of SEQ ID NOs: 2 to 5, more particularly an amino acid sequence selected from the group consisting of SEQ ID NOs: 2 to 4, and most particularly the mutant FGF-21 peptide comprises the amino acid sequence as depicted in SEQ ID NO: 2.

In other particular embodiments, the mutant FGF-21 peptide conjugate comprises at least one glycosyl moiety comprising N-acetylgalactosamine (GalNAc), galactose (Gal) and/or sialic acid (Sia). In a particular embodiment thereof, the at least one glycosyl moiety comprises the structure -GalNAc-Sia-.

In other particular embodiments, the mutant FGF-21 peptide conjugate comprises a 20 kDa PEG moiety which is attached to the at least one glycosyl moiety via an amino acid residue, particularly glycine (Gly). In an even more particular embodiment, the mutant FGF-21 peptide conjugate comprises the structure -GalNAc-Sia-Gly-PEG(20 kDa). Still more particularly, the mutant FGF-21 peptide conjugate comprises the structure:

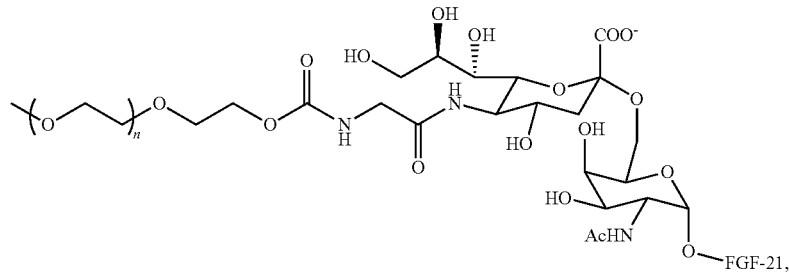

wherein n is an integer selected from 450 to 460.

In some embodiments, the mutant FGF-21 peptide conjugate comprises a 20 kDa PEG which is a linear or branched PEG. In some embodiments, the mutant FGF-21 peptide conjugate comprises a 20 kDa PEG which is a linear PEG. In some embodiments, the 20 kDa PEG is a 20 kDa methoxy-PEG.

In an exemplary embodiment, the polymeric modifying group is PEG. In another exemplary embodiment, the PEG moiety has a molecular weight of 20-30 kDa. In exemplary embodiments, the PEG moiety has a molecular weight of 17 kDa, 18 kDa, 19 kDa, 20 kDa, 21 kDa, 22 kDa, 23 kDa, 24 kDa, 25 kDa, 26 kDa, 27 kDa, 28 kDa, 29 kDa, 30 kDa, 31 kDa, 32 kDa, or 33 kDa. In another exemplary embodiment, the PEG moiety has a molecular weight of 20 kDa. In another exemplary embodiment, the PEG moiety has a molecular weight of 30 kDa. In another exemplary embodiment, the PEG moiety has a molecular weight of about 5 kDa. In another exemplary embodiment, the PEG moiety has a molecular weight of about 10 kDa. In another exemplary embodiment, the PEG moiety has a molecular weight of about 40 kDa.

In some embodiments, the glycosyl linking group is a linear 10 kDa-PEG-sialyl, and one or two of these glycosyl linking groups are covalently attached to the peptide.

In some embodiments, the glycosyl linking group is a linear 20 kDa-PEG-sialyl, and one or two of these glycosyl linking groups are covalently attached to the peptide. In an exemplary embodiment, the glycosyl linking group is a linear 30 kDa-PEG-sialyl, and one or two of these glycosyl linking groups are covalently attached to the peptide. In an exemplary embodiment, the glycosyl linking group is a linear 5 kDa-PEG-sialyl, and one, two or three of these glycosyl linking groups are covalently attached to the peptide. In an exemplary embodiment, the glycosyl linking group is a linear 40 kDa-PEG-sialyl, and one or two of these glycosyl linking groups are covalently attached to the peptide.

In some embodiments, a mutant FGF-21 peptide is pegylated in accordance with methods described herein. In some embodiments, the mutant FGF-21 peptide comprises the mutations $S^{172}T$ and $R^{176}A$, wherein the positions of the amino acids S and R are based on the amino acid sequence as depicted in SEQ ID NO: 1. In some embodiments, the mutant FGF-21 peptide comprises the amino acid sequence as depicted in SEQ ID NO: 2. As detailed herein above, the at least one glycosyl moiety attached to the threonine residue and linking the newly introduced threonine residue to the PEG moiety may virtually be any possible glycosyl moiety. The only limitation is that it should be able to attach to threonine and that it should be able to be attached to PEG or m-PEG, for example via a linker, e.g. an amino acid residue, including but not limited to glycine. In some embodiments, the at least one glycosyl moiety comprises N-acetylgalactosamine (GalNAc), galactose (Gal) and/or sialic acid (Sia). In some embodiments, the at least one glycosyl moiety comprises the structure -GalNAc-Sia-, i.e. two glycosyl moieties, namely GalNAc and Sia, wherein the PEG residue may be attached to GalNAc or Sia. The glycosyl moiety which is not attached to the PEG moiety may be attached to the newly introduced threonine residue.

In some embodiments, the 20 kDa PEG moiety is attached to the at least one glycosyl linker via a linker, e.g. an amino acid residue, for example a small amino acid, such as alanine or glycine, for example via glycine (Gly). Hence, the PEG or m-PEG moiety is attached to the amino acid and the amino acid is attached to a glycosyl moiety, such as Sia. The glycosyl moiety is attached to the amino acid linker, if present, and to the newly introduced threonine residue in the mutant FGF-21 amino acid sequence. The amino acid residue is attached to PEG and the glycosyl residue via a method described in WO 03/031464 which is incorporated herein by reference.

In some embodiments, the mutant FGF-21 peptide (e.g., SEQ ID NO: 2) conjugate comprises the structure -GalNAc-Sia-Gly-PEG(20 kDa), wherein GalNAc is attached, e.g. to a newly introduced threonine residue and to Sia. Sia is further attached via a glycine residue to a PEG of 17 kDa, 18 kDa, 19 kDa, 20 kDa, 21 kDa, 22 kDa, 23 kDa, 24 kDa, 25 kDa, 26 kDa, 27 kDa, 28 kDa, 29 kDa, 30 kDa, 31 kDa, 32 kDa, or 33 kDa.

In some embodiments, the mutant FGF-21 peptide (e.g., SEQ ID NO: 2) conjugate comprises the structure -GalNAc-Sia-Gly-PEG(20 kDa), wherein GalNAc is attached, e.g. to a newly introduced threonine residue and to Sia. Sia is further attached via a glycine residue to a PEG of 20 kDa, 21 kDa, 22 kDa, 23 kDa, 24 kDa, 25 kDa, 26 kDa, 27 kDa, 28 kDa, 29 kDa, or kDa.

In some embodiments, the mutant FGF-21 peptide (e.g., SEQ ID NO: 2) conjugate comprises the structure -GalNAc-Sia-Gly-PEG(20 kDa), wherein GalNAc is attached, e.g. to a newly introduced threonine residue and to Sia. Sia is further attached via a glycine residue to a PEG of 20 kDa, 25 kDa, or 30 kDa.

In some embodiments, the mutant FGF-21 peptide (e.g., SEQ ID NO: 2) conjugate comprises the structure -GalNAc-Sia-Gly-PEG(20 kDa), wherein GalNAc is attached, e.g. to a newly introduced threonine residue and to Sia. Sia is further attached via a glycine residue to a PEG of 20 kDa or 30 kDa.

In some embodiments, the mutant FGF-21 peptide (e.g., SEQ ID NO: 2) conjugate comprises the structure -GalNAc-Sia-Gly-PEG(20 kDa), wherein GalNAc is attached, e.g. to a newly introduced threonine residue and to Sia. Sia is further attached via a glycine residue to a PEG of 20 kDa.

In some embodiments, the mutant FGF-21 peptide conjugate comprises the structure:

20 kDa means that the size of the PEG residues is 20 kDa in average and that the majority of the PEG residues are 20 kDa in size.

Mutant FGF-21 Peptides and Conjugates Thereof

As described herein, variants of Fibroblast Growth Factor-21 (FGF-21) having surprising properties, including variants having exceptionally long half-lives are produced, which variants are peptide conjugates comprising
   i) a mutant FGF-21 peptide comprising at least one threonine (T) residue adjacent to at least one proline (P) residue on the C-terminal side of the at least one proline residue, thereby forming at least one O-linked glycosylation site which does not exist in the corresponding native FGF-21, wherein the corresponding native FGF-21 has an amino acid sequence that is at least 95% identical to SEQ ID NO: 1, and
   ii) a 20-30 kDa polyethylene glycol (PEG), wherein said 20-30 kDa PEG is covalently attached to said mutant FGF-21 peptide at the at least one threonine residue via at least one glycosyl moiety.

For the attachment of the 20-30 kDa PEG residue, a threonine residue is introduced into the amino acid sequence of native FGF-21 adjacent to and on the C-terminal side of a proline residue which is already present in the amino acid sequence of native FGF-21, i.e. is a native proline residue. For this purpose, either (i) an additional threonine may be introduced immediately next to the native proline residue or (ii) the native amino acid which is present in the native amino acid sequence of FGF-21 adjacent to and located on the C-terminal side of a native proline residue is exchanged for a threonine residue. In the present invention, option (ii) is an exemplary embodiment. As described herein, more than one threonine residue may be introduced adjacent and C-terminal to a proline residue which is already present. A mutant FGF-21 of the present invention may thus comprise both threonine residues which have been additionally introduced and threonine residues which have been introduced instead of a native amino acid.

By the introduction of a new threonine residue on the C-terminal side and adjacent to a proline residue, a consensus sequence for O-glycosylation enzyme is formed. Because proline residues are typically found on the surface of proteins (in, e.g., turns, kinks, and/or loops), a design that calls for O-glycosylation and PEGylation thereto using a

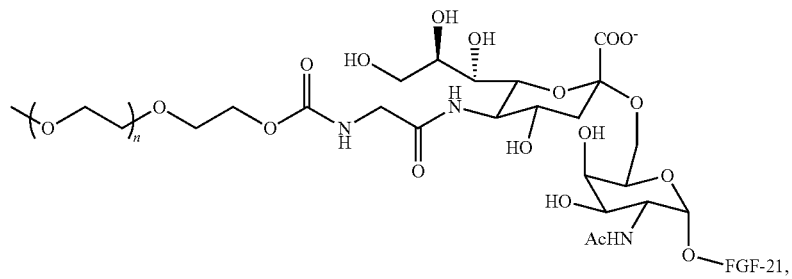

wherein n is an integer selected from 450 to 460.

The 20 kDa PEG may be linear or branched. In some embodiments, the 20 kDa PEG is a linear 20 kDa PEG. Further, the 20 kDa PEG can be a 20 kDa methoxy-PEG (mPEG, m-PEG). PEG and mPEG of different molecular weight can be obtained from various suppliers, such as from JenKem Technology USA, Plano, TX, USA, or Merckle Biotec, Ulm, Germany. It is understood in the art that PEG PEG-glycosyl moiety in close proximity to a proline residue benefits from the relative accessibility of the target attachment site for the glycosyl transferase that transfers the glycosyl or glycol-PEG moiety and the potential to accommodate the conjugated glycosyl and/or PEG structure without disruption of protein structure.

For introduction of the threonine residues into the native amino acid sequence of FGF-21, the general methods include Sambrook and Russell, Molecular Cloning, A Laboratory Manual (3rd ed. 2001); Kriegler, Gene Transfer and Expression: A Laboratory Manual (1990); and Ausubel et al., eds., Current Protocols in Molecular Biology (1994).

In some embodiments, the native FGF-21 amino acid sequence corresponds to the native amino acid sequence of human FGF-21 depicted in SEQ ID NO: 1.

In some embodiments, the mutant FGF-21 peptide comprises the amino acid sequence PT, i.e. a threonine residue C-terminally adjacent to a proline residue. The sequence PT is not present in the native FGF-21 amino acid sequence.

Optionally, the mutant FGF-21 peptide comprises at least one amino acid sequence selected from the group consisting of $P^{172}T$ (e.g. SEQ ID NO: 2 or 3), $P^{156}T$ (e.g. SEQ ID NO: 4), $P^{5}T$ (e.g. SEQ ID NO: 5), $P^{3}T$ (e.g. SEQ ID NO: 6), $P^{9}T$ (e.g. SEQ ID NO: 7), $P^{50}T$ (e.g. SEQ ID NO: 8), $P^{61}T$ (e.g. SEQ ID NO: 9), $P^{79}T$ (e.g. SEQ ID NO: 10), $P^{91}T$ (e.g. SEQ ID NO: 11), $P^{116}T$ (e.g. SEQ ID NO: 12), $P^{120}T$ (e.g. SEQ ID NO: 13), $P^{125}T$ (e.g. SEQ ID NO: 14), $P^{129}T$ (e.g. SEQ ID NO: 15), $P^{131}T$ (e.g. SEQ ID NO: 16), $P^{134}T$ (e.g. SEQ ID NO: 17), $P^{139}T$ (e.g. SEQ ID NO: 18), $P^{141}T$ (e.g. SEQ ID NO: 19), $P^{144}T$ (e.g. SEQ ID NO: 20, $P^{145}T$ (e.g. SEQ ID NO: 21), $P^{148}T$ (e.g. SEQ ID NO: 22), $P^{150}T$ (e.g. SEQ ID NO: 23), $P^{151}T$ (e.g. SEQ ID NO: 24), $P^{158}T$ (e.g. SEQ ID NO: 25), $P^{159}T$ (e.g. SEQ ID NO: 26), $P^{166}T$ (e.g. SEQ ID NO: 27), $P^{178}T$ (e.g. SEQ ID NO: 28), and combinations thereof, wherein the positions of proline and threonine are based on the native amino acid sequence of FGF-21 as depicted in SEQ ID NO: 1. In some embodiments, the mutant FGF-21 peptide comprises at least one amino acid sequence selected from the group consisting of $P^{172}T$, $P^{156}T$, $P^{5}T$ and combinations thereof. In some embodiments, the mutant FGF-21 peptide comprises at least one amino acid sequence selected from the group consisting of $P^{172}T$, $P^{156}T$ and combinations thereof. In some embodiments, the mutant FGF-21 peptide comprises the sequence motif $P^{172}T$, based on the amino acid sequence as depicted in SEQ ID NO: 1, wherein the positions of proline and threonine are based on the amino acid sequence as depicted in SEQ ID NO: 1.

In some embodiments, the proline residue is located between amino acid 145 and the C-terminus of the mutant FGF-21 peptide, wherein the position of amino acid 145 is based on the amino acid sequence as depicted in SEQ ID NO: 1. As demonstrated by results presented herein, the C-terminus of FGF-21 surprisingly tolerates attachment of PEG and in particular of glycosyl-PEG moieties. This was unexpected since the literature reports that the intact C-terminus is necessary for β-Klotho binding of FGF-21.

In some embodiments, the mutant FGF-21 peptide comprises the mutations $S^{172}T$ and $R^{176}A$, wherein the positions of the amino acids S and R are based on the amino acid sequence as depicted in SEQ ID NO: 1. In some embodiments, the mutant FGF-21 peptide comprises the amino acid sequence as depicted in SEQ ID NO: 2. The mutation $R^{176}A$ has been found beneficial to the protein's overall stability after introducing the O-linked glycosylation site at threonine 173. By this mutation, the relatively large arginine side chain was removed and replaced by the small side chain of alanine. It is assumed that the smaller side chain of alanine interferes less with the voluminous glycosyl-PEG moiety to be attached to thindicae mutated FGF-21 peptide.

In an alternative embodiment, the mutant FGF-21 peptide comprises the mutation $Q^{157}T$, wherein the position of the amino acid Q is based on the amino acid sequence as depicted in SEQ ID NO: 1. In some embodiments, the mutant FGF-21 peptide comprises the amino acid sequence as depicted in SEQ ID NO: 4, or the mutation $D^{6}T$, wherein the position of the amino acid D is based on the amino acid sequence as depicted in SEQ ID NO: 1. In some embodiments, the mutant FGF-21 peptide comprises the amino acid sequence as depicted in SEQ ID NO: 5.

In some embodiments, the mutant FGF-21 peptide conjugate comprises an amino acid sequence selected from the group consisting of SEQ ID NOs: 2 to 28. In some embodiments, the mutant FGF-21 peptide conjugate comprises an amino acid sequence selected from the group consisting of SEQ ID NOs: 2 to 5. In some embodiments, the mutant FGF-21 peptide conjugate comprises an amino acid sequence selected from the group consisting of SEQ ID NOs: 2 to 4. In some embodiments, the mutant FGF-21 peptide conjugate comprises an amino acid sequence as depicted in SEQ ID NO: 2.

In some embodiments, exemplary conjugates of a modified sugar and a mutant FGF-21 peptide are presented. In some embodiments, mutant FGF-21 peptide conjugates were made comprising a mutant FGF peptide and at least one modified sugar, wherein a first of the at least one modified sugar is linked to an amino acid of the peptide through a glycosyl linking group. As described herein, the amino acid to which the glycosyl linking group is attached is mutated to create a site recognized by the glycosyltransferase.

In some embodiments, a mutant FGF-21 peptide conjugate can comprise a mutant FGF-21 peptide and a glycosyl group attached to the mutated amino acid residue of the mutant FGF-21 peptide.

In some embodiments, the glycosyl group is an intact glycosyl linking group. In another exemplary embodiment, the glycosyl group further comprises a modifying group. In another exemplary embodiment, the modifying group is a non-glycosidic modifying group. In another exemplary embodiment, the modifying group does not include a naturally occurring saccharide moiety.

Pharmaceutical Composition

In some embodiments, the pharmaceutical compositions are suitable for use in a variety of drug delivery systems. Suitable formulations for use in the present invention are found in Remington's Pharmaceutical Sciences, Mack Publishing Company, Philadelphia, PA, $17^{th}$ ed. (1985). The pharmaceutical compositions are intended for parenteral, intranasal, topical, oral, or local administration, such as by subcutaneous injection, aerosol inhalation, or transdermal adsorption, for prophylactic and/or therapeutic treatment. Commonly, the pharmaceutical compositions are administered parenterally, e.g., subcutaneously or intravenously.

In some embodiments, the invention provides compositions for parenteral administration which comprise the mutant FGF-21 peptide conjugate dissolved or suspended in an acceptable carrier, particularly an aqueous carrier, e.g., water, buffered water, saline, phosphate buffered saline (PBS) and the like. The compositions may also contain detergents such as Tween 20 and Tween 80; stabilizers such as mannitol, sorbitol, sucrose, and trehalose; and preservatives such as EDTA and m-cresol. The compositions may contain pharmaceutically acceptable auxiliary substances as required to approximate physiological conditions, such as pH adjusting and buffering agents, tonicity adjusting agents, wetting agents, detergents and the like.

In some embodiments, the pharmaceutical compositions may be sterilized by conventional sterilization techniques or may be sterile filtered. The resulting aqueous solutions may be packaged for use as is, or lyophilized, the lyophilized preparation being combined with a sterile aqueous carrier prior to administration. The compositions containing the FGF peptide conjugates can be administered for prophylactic and/or therapeutic treatments, in particular for the treatment of SHTG. In therapeutic applications, compositions are administered to a subject already suffering from a disease or condition related to SHTG, in an amount sufficient to cure or at least partially arrest the symptoms of the disease and its complications. An amount adequate to accomplish this is defined as a "therapeutically effective amount" and usually depends on the patient's state of health and weight.

In some embodiments, the therapeutic dosing regimen comprises a range of about 3 mg to about 44 mg, a range of about 3 mg to about 36 mg; a range of about 3 mg to about 30 mg; a range of about 3 mg to about 27 mg; a range of about 3 mg to about 18 mg; a range of about 3 mg to about 15 mg; a range of about 9 mg to about 44 mg, a range of about 9 mg to about 36 mg, a range of about 9 mg to about 30 mg, a range of about 9 mg to about 27 mg; a range of about 9 mg to about 18 mg; a range of about 9 mg to about 15 mg; a range of about 15 mg to about 44 mg, a range of about 15 mg to about 36 mg, a range of about 15 mg to about 30 mg, a range of about 15 mg to about 27 mg; a range of about 15 mg to about 18 mg; a range of about 18 mg to about 44 mg, a range of about 18 mg to about 36 mg, a range of about 18 mg to about 30 mg, a range of 18 mg to 27 mg; a range of about 15 mg to about 44 mg, a range of about 15 mg to about 36 mg, a range of about 15 mg to about 30 mg, a range of 15 mg to 27 mg; a range of 15 mg to 18 mg; a range about 3 mg to about 9 mg; a range of about 9 mg to about 15 mg; a range of about 9 mg to about 18 mg; a range of about 18 mg to about 27 mg; a range of about 27 mg to about 30 mg; a range of about 18 mg to about 27 mg; a range of about 3 mg to about 18 mg; a range of about 18 mg to about 36 mg. In some embodiments, the therapeutic dosing regimen comprises a range of about 3 mg to about 50 mg; a range of about 5 mg to about 50 mg; a range of about 10 mg to about mg; a range of about 20 mg to about 50 mg; a range of about 30 mg to about 50 mg; or a range of about 40 mg to about 50 mg; and any whole integer within any of the indicated ranges. In some embodiments, the therapeutic dosing regimen comprises a range of about 5 mg to about 40 mg; a range of about 10 mg to about 40 mg; a range of about 20 mg to about 40 mg; a range of about 30 mg to about 40 mg; or a range of about 35 mg to about 40 mg; and any whole integer within any of the indicated ranges. In some embodiments, the therapeutic dosing regimen comprises a range of about 5 mg to about 30 mg; a range of about 10 mg to about 30 mg; a range of about 20 mg to about 30 mg; or a range of about 25 mg to about 30 mg; and any whole integer within any of the indicated ranges. In some embodiments, the therapeutic dosing regimen comprises a range of about 10 mg to about 20 mg; or a range of about 15 mg to about 20 mg; and any whole integer within any of the indicated ranges. In some embodiments, the therapeutic dosing regimen comprises a dose of about 3 mg; about 9 mg; about 15 mg, about 18 mg; about 27 mg, about 30 mg, about 36 mg or about 44 mg. The term "about" as used herein refers to an amount equal to 10% more or 10% less of the particularly indicated amount. For example, about 10 mg refers to a range of 9-11 mg. In yet another particular embodiment thereof, the therapeutic dosing regimen comprises a dose of 9.1 mg; about 18.2 mg; or about 39 mg.

In some embodiments, the pharmaceutical composition is a liquid pharmaceutical composition comprising at least one mutant FGF-21 peptide conjugate and a pharmaceutically acceptable carrier. In some embodiments, the mutant FGF-21 peptide conjugate is present in a concentration in the range from 0.1 mg/mL to 50 mg/mL. In some embodiments, the mutant FGF-21 peptide conjugate is present in a concentration in the range from 10 mg/mL to 48 mg/mL. In some embodiments the mutant FGF-21 peptide conjugate is present in a concentration of 26±4 mg/mL. For example, the FGF-21 peptide conjugate is present at a concentration of about 22, 23, 24, 25, 26, 27, 28, 29, 30, 31, 32, 33, 34, 35, 36 mg/mL. In some embodiments, the mutant FGF-21 peptide conjugate is present in a 36±6 mg/mL. For example, the FGF-21 peptide conjugate is present at a concentration of about 30, 31, 32, 33, 34, 35, 36, 37, 38, 39, 40, 41, 42 mg/mL.

In some embodiments, the liquid pharmaceutical composition comprises 10-48 mg/ml FGF-21 peptide conjugate, for example 15 mg/ml, 18 mg/ml, 20 mg/ml, 28 mg/ml, 30 mg/ml, 36 mg/ml, 42 mg/ml, 44 mg/ml, 48 mg/ml.

In some embodiments, liquid pharmaceutical composition comprises or consists of from about 10 mg/ml to about 48 mg/ml of a mutant Fibroblast Growth Factor-21 (FGF-21) peptide conjugate, from about 50 mM to about 500 mM arginine; from about 0.01 to about 0.1% (w/v) Polysorbate 80 (PS-80) or Polysorbate 20 (PS-20); about 20 mM buffer, pH 7-8; and a pharmaceutically acceptable carrier. In some embodiments, liquid pharmaceutical composition comprises or consists of from about 10 mg/ml to about 48 mg/ml of a mutant Fibroblast Growth Factor-21 (FGF-21) peptide conjugate, from about 150 mM to about 500 mM arginine; from about to about 0.1% (w/v) Polysorbate 80 (PS-80) or Polysorbate 20 (PS-20); about 20 mM buffer, pH 7-8; and a pharmaceutically acceptable carrier. In some embodiments, the formulation has an osmolality between about 250 mOsmol/kg to about 510 mOsmol/kg. In some embodiments, the liquid formulation comprises or consists of from 10 mg/ml to 48 mg/ml of a mutant Fibroblast Growth Factor-21 (FGF-21) peptide conjugate comprising a mutant FGF-21 peptide comprising the amino acid sequence of SEQ ID NO: 2, a glycosyl moiety, and a 20 kDa polyethylene glycol (PEG), wherein the mutant FGF-21 peptide is attached to the glycosyl moiety by a covalent bond between a threonine at amino acid position 173 of SEQ ID NO: 2 and a first site of the glycosyl moiety and wherein the glycosyl moiety is attached to the 20 kDa PEG by a covalent bond between a second site of the glycosyl moiety and the 20 kDa PEG; from 50 mM to 500 mM Arginine; from to 0.1% (w/v) Polysorbate 80 (PS-80) or Polysorbate 20 (PS-20); 20 mM buffer, pH 7-8; and a pharmaceutically acceptable carrier. In some embodiments, the liquid formulation comprises or consists of from 10 mg/ml to 48 mg/ml of a mutant Fibroblast Growth Factor-21 (FGF-21) peptide conjugate comprising a mutant FGF-21 peptide comprising the amino acid sequence of SEQ ID NO: 2, a glycosyl moiety, and a 20 kDa polyethylene glycol (PEG), wherein the mutant FGF-21 peptide is attached to the glycosyl moiety by a covalent bond between a threonine at amino acid position 173 of SEQ ID NO: 2 and a first site of the glycosyl moiety and wherein the glycosyl moiety is attached to the 20 kDa PEG by a covalent bond between a second site of the glycosyl moiety and the 20 kDa PEG; from 150 mM to 500 mM Arginine; from 0.01 to 0.1% (w/v) Polysorbate 80 (PS-80) or Polysorbate 20 (PS-20); 20 mM buffer, pH 7-8; and a pharmaceutically acceptable carrier. In some embodiments, the formulation has an osmolality between about 250 mOsmol/kg to about 550 mOsmol/kg. In some embodiments, the liquid pharmaceutical composition comprising or consisting of from about 10 mg/ml to about 48 mg/ml of a mutant Fibroblast Growth Factor-21 (FGF-21) peptide conjugate comprising a mutant FGF-21 peptide comprising the amino acid sequence of SEQ ID NO: 2, a glycosyl moiety, and a 20 kDa polyethylene glycol (PEG), wherein the mutant FGF-21 peptide is attached to the glycosyl moiety by a covalent bond between a threonine at amino acid position 173 of SEQ ID NO: 2 and a first site of the glycosyl moiety and wherein the glycosyl moiety is attached to the 20 kDa PEG by a covalent bond between a second site of the glycosyl moiety and the 20 kDa PEG; from about 50 mM to about 500 mM arginine, from about 50 mM to about 250 mM alanine, about 50 mM to about 250 mM proline, about 50 mM to about 250 mM glycine, about 50 mM to about 250 mM MgCl2, about 1% to about 5% (v/v) glycerol, about 1% to 5% (v/v) PEG 400, or combination thereof; from about 0.01 to about 0.1% (w/v) Polysorbate 80 (PS-80) or Polysorbate 20 (PS-20); about 20 mM buffer at pH 7-8; and a pharmaceutically acceptable carrier. In some embodiments, the liquid pharmaceutical composition comprising or consisting of from about 10 mg/ml to about 48 mg/ml of a mutant Fibroblast Growth Factor-21 (FGF-21) peptide conjugate comprising a mutant FGF-21 peptide comprising the amino acid sequence of SEQ ID NO: 2, a glycosyl moiety, and a 20 kDa polyethylene glycol (PEG), wherein the mutant FGF-21 peptide is attached to the glycosyl moiety by a covalent bond between a threonine at amino acid position 173 of SEQ ID NO: 2 and a first site of the glycosyl moiety and wherein the glycosyl moiety is attached to the 20 kDa PEG by a covalent bond between a second site of the glycosyl moiety and the 20 kDa PEG; from about 150 mM to about 500 mM arginine, from about 50 mM to about 250 mM alanine, about 50 mM to about 250 mM proline, about 50 mM to about 250 mM glycine, about 50 mM to about 250 mM MgCl2, about 1% to about 5% (v/v) glycerol, about 1% to 5% (v/v) PEG 400, or combination thereof; from about 0.01 to about 0.1% (w/v) Polysorbate 80 (PS-80) or Polysorbate 20 (PS-20); about 20 mM buffer at pH 7-8; and a pharmaceutically acceptable carrier. In some embodiments, the weight ratio of mutant FGF-21 to arginine is from about 0.6 to about 0.7, from about 0.6 to about 0.8, about 0.6 to about 0.9, from about 0.6 to about 1, e.g. about 0.6, 0.7, 0.8, 0.9, 0.1. In some embodiments, the molar ratio of mutant FGF-21 to arginine is from about from about 0.006 to about 0.008, 0.006 to about 0.009, 0.006 to about 0.010, from about 0.007 to about 0.008, from about 0.007 to about 0.009, from about 0.007 to about 0.010, e.g about 0.006, 0.007, 0.008, 0.009.

In some embodiments, the liquid formulation has an osmolality of about 250 mOsmol/kg to about 550 mOsmol/kg.

Liquid pharmaceutical compositions in some embodiments comprise 20 mg/mL PEG-FGF21 in 20 mM Tris, 150 mM Arginine, 0.02% (w/v) PS-80, pH 7.5. Liquid pharmaceutical formulations in some embodiments comprise 20 mg/mL PEG-FGF21 in 20 mM Phosphate, 150 mM Arginine, 0.02% (w/v) PS-80, pH 7.5. In some embodiments, the composition has an osmolality between about 250 mOsm/kg to about 380 mOsm/kg. In some embodiments, the composition has an osmolality of about 300 mOsm/kg. Liquid pharmaceutical compositions in some embodiments comprise 28 mg/mL PEG-FGF21 in 20 mM Tris, 275 mM Arginine, 0.02% (w/v) PS-80, pH 7-8. In some embodiments, the composition has an osmolality of about 505 mOsm/kg. Liquid pharmaceutical formulations in some embodiments comprise 18-44 mg/mL PEG-FGF21 in 20 mM Tris, 200-350 mM Arginine, 0.02% (w/v) PS-80, pH 7.0-pH 7.5. In some embodiments, the liquid pharmaceutical composition comprises about 20 mg/mL PEG-FGF21, about 150 mM arginine HCl, about 20 mM Tris, 0.02% (w/v) PS-80, wherein pH is about 7.5 and has an osmolality is about 300 mOsm/kg. In some embodiments, the liquid pharmaceutical composition comprises about 28 mg/mL PEG-FGF21, about 260 mM Arginine HCl, about 20 mM Tris, about 0.02% (w/v) PS80, wherein pH is about 7.1. In some embodiments, the liquid pharmaceutical composition comprises about 28 mg/mL PEG-FGF21, about 260 mM Arginine HCl, about 20 mM Tris, about 0.02% (w/v) PS80, wherein pH is about 7.1 and has an osmolality of about 505 mOsm/kg. In some embodiments, the liquid pharmaceutical composition comprises about 36 mg/mL PEG-FGF21, about 270 mM Arginine HCl, about 20 mM Tris, about 0.02% (w/v) PS80, wherein pH is about 7.1. In some embodiments, the liquid pharmaceutical composition comprises about 36 mg/mL PEG-FGF21, about 270 mM Arginine HCl, about 20 mM Tris, about 0.02% (w/v) PS80, wherein pH is about 7.1 and has a osmolality is about 530 mOsm/kg. In some embodiments, the liquid pharmaceutical composition comprises 36 mg/mL PEG-FGF21, 200 mM Arginine HCl, 20 mM Tris, 0.02% (w/v) PS80, wherein pH is about 7.1. In some embodiments, the liquid pharmaceutical composition comprises 36 mg/mL PEG-FGF21, 200 mM Arginine HCl, Tris, 0.02% (w/v) PS80, wherein pH is about 7.1 and has an osmolality is about 421 mOsm/kg. In some embodiments, the liquid pharmaceutical composition comprises about 42 mg/mL PEG-FGF21, about 270 mM Arginine HCl, about 20 mM Tris, about 0.02% (w/v) PS80, wherein pH is about 7.1. In some embodiments, the liquid pharmaceutical composition comprises about 42 mg/mL PEG-FGF21, about 270 mM Arginine HCl, about 20 mM Tris, about 0.02% (w/v) PS80, wherein pH is about 7.1 and has an osmolality is about 528 mOsm/kg. In some embodiments, the liquid pharmaceutical composition comprises 44 mg/mL mutant FGF21, 200 mM Arginine HCl, 20 mM Tris, 0.02% (w/v) PS80, wherein pH is 7.1. In some embodiments, the liquid pharmaceutical composition comprises 44 mg/mL PEG-FGF21, 200 mM Arginine HCl, Tris, 0.02% (w/v) PS80, wherein pH is 7.1 and has an osmolality is about 455 mOsm/kg. In some embodiments, the liquid pharmaceutical composition comprises 44 mg/mL PEG-FGF21, 230 mM Arginine HCl, 20 mM Tris, 0.02% (w/v) PS80, wherein pH is 7.1. In some embodiments, the liquid pharmaceutical composition comprises 44 mg/mL PEG-FGF21, 230 mM Arginine HCl, 20 mM Tris, 0.02% (w/v) PS80, wherein pH is 7.1 and has an osmolality is about 485 mOsm/kg.

In some embodiments, the liquid composition further comprises a surfactant. In some embodiments, the surfactant comprises cetrimonium bromide, sodium gluconate or combination thereof. In some embodiments, the liquid formulation comprises from about 0.05% to about 0.1% (w/v) cetrimonium bromide, from about 0.05% to about 0.1% (w/v) sodium gluconate or combination thereof.

In some embodiments, the liquid pharmaceutical composition further comprising one or more active agent. In some embodiments, the PEG-FGF21 is co-formulated with one or more active agent.

The buffering agent may be present in a concentration from 1 mM to 100 mM. In some embodiments, the buffering agent is present at a concentration ranging from 2 mM to 75 mM, 5 mM to 50 mM, 10 mM to 25 mM, 14 to 22 mM. In some embodiments, the buffering agent is present at a concentration of about 14, 16, 18, 20, 22, 24, 26, 30, 32, 34, 36, 38, 40 mM or more. For example, the buffering agent is present at a concentration of about 20 mM. The pH may be in the range from 6.0 to 8.5, from 6.5 to 8.0, from 6.75 to 8.0, from 7.1 to 8. The buffering agent may be a Tris phosphate buffer. For example, the buffering agent can have a pH of 7, 7.1, 7.2, 7.3, 7.4, 7.5, 7.6, 7.7, 7.8, 7.9 or 8.

The liquid pharmaceutical composition may further comprise a tonicity modifying agent. Suitable tonicity modifying agents include glycerol, amino acids, sodium chloride, proteins, or sugars and sugar alcohols. For example, the modifying agent comprise arginine, such as arginine HCl or arginine sulfate. The tonicity modifying agent is present in a concentration of 50 mM to 500 mM. For example, the modifying agent (e.g. arginine HCL) comprises from 150 mM to 500 mM arginine, 150 to 275 mM or 245 to 275 mM. In some embodiments, modifying agent comprise arginine, such as arginine HCl or arginine sulfate is present at a concentration between 31.6 mg/ml (150 mM) and 54.8 mg/ml (260 mM).

The liquid pharmaceutical composition may further comprise a non-ionic surfactant. The non-ionic surfactant may be a polysorbate-based non-ionic surfactant, particularly polysorbate 20 or polysorbate 80, and more particularly polysorbate 80. The non-ionic surfactant may be present in a concentration of 0.01% (w/v) to 1% (w/v). For example, the non-ionic surfactant may be present in a concentration of 0.01%, 0.02%. 0.03%, 0.04%, 0.05%, 0.06%, 0.07%, 0.08%, 0.09%, 0.2%, 0.3%, 0.4%, 0.5%, 0.6%, 0.7%, 0.8%, 0.9%, or 1% (w/v).

In some embodiments, the liquid pharmaceutical composition may further comprise cetrimonium bromide, sodium gluconate or combination thereof. For example, the composition may comprise from 0.05% to 0.1% (w/v) cetrimonium bromide, from 0.05% to 0.1% (w/v) sodium gluconate or combination thereof.

In an embodiment, the liquid pharmaceutical composition comprises 10 mg/mL to 50 mg/mL of mutant FGF-21 peptide conjugate, 1 mM to 100 mM buffering agent, for example Tris buffer, 150 mM to 500 mM tonicity arginine, and 0.02% to 1% (w/v) polysorbate-based non-ionic surfactant, particularly polysorbate 80, and has a pH of 7.0 to 8.0.

In some embodiments, the liquid formulation comprises 0.02% (w/v) PS80 (0.2 mg/ml). In some embodiments, the buffer is Tris or phosphate buffer. In some embodiments, the liquid formulation comprises 20 mM Tris buffer. In some embodiments, the liquid formulation comprises 28 mg/ml of mutant FGF-21. In some embodiments, the liquid formulation comprises 36 mg/ml of mutant FGF-21. In some embodiments, the liquid formulation comprises 44 mg/ml of mutant FGF-21. In some embodiments, the liquid formulation comprises from 150 mM to 275 mM arginine. In some embodiments, arginine is arginine HCl or arginine sulfate. In some embodiments, the pH is 7.1.

In some embodiments, the liquid pharmaceutical composition comprises about 20 mg/mL mutant FGF21, about 150 mM arginine HCl, about 20 mM Tris, 0.02% (w/v) PS-80 and wherein pH is about 7.5. In some embodiments, the liquid pharmaceutical composition comprises about 28 mg/mL mutant FGF21, about 260 mM arginine HCl, about 20 mM Tris, about 0.02% (w/v) PS80 and wherein pH is about 7.1. In some embodiments, the liquid pharmaceutical composition comprises about 36 mg/mL mutant FGF21, about 270 mM arginine HCl, about 20 mM Tris, about (w/v) PS80 and wherein pH is about 7.1. In some embodiments, the liquid pharmaceutical composition comprises 36 mg/mL mutant FGF21, 20 0 mM arginine HCl, 20 mM Tris, 0.02% (w/v) PS80 and wherein pH is about 7.1 In some embodiments, the liquid pharmaceutical composition comprises about 42 mg/mL mutant FGF21, about 270 mM arginine HCl, about 20 mM Tris, about (w/v) PS80 and wherein pH is about 7.1. In some embodiments, the liquid pharmaceutical composition comprises 44 mg/mL mutant FGF21, 200 mM arginine HCl, 20 mM Tris, 0.02% (w/v) PS80 and wherein pH is 7.1. In some embodiments, the liquid pharmaceutical composition comprises 44 mg/mL mutant FGF21, 230 mM arginine HCl, 20 mM Tris, 0.02% (w/v) PS80 and wherein pH is 7.1.

In some embodiments, the pharmaceutical composition is a liquid pharmaceutical composition comprising: (a) from 10 mg/ml to 48 mg/ml of a mutant Fibroblast Growth Factor-21 (FGF-21) peptide conjugate comprising a mutant FGF-21 peptide comprising the amino acid sequence of SEQ ID NO: 2, a glycosyl moiety, and a 20 kDa polyethylene glycol (PEG), wherein the mutant FGF-21 peptide is attached to the glycosyl moiety by a covalent bond between a threonine at amino acid position 173 of SEQ ID NO: 2 and a first site of the glycosyl moiety and wherein the glycosyl moiety is attached to the 20 kDa PEG by a covalent bond between a second site of the glycosyl moiety and the 20 kDa PEG; (b) from 50 mM to 500 mM arginine; (c) from to 0.1% (w/v) Polysorbate 80 (PS-80) or Polysorbate 20 (PS-20); (d) from 5 to 25 mM buffer, pH 7-8; and (e) a pharmaceutically acceptable carrier.

In some embodiments, the pharmaceutical composition is a liquid pharmaceutical composition comprising: (a) from 10 mg/ml to 48 mg/ml of a mutant Fibroblast Growth Factor-21 (FGF-21) peptide conjugate comprising a mutant FGF-21 peptide comprising the amino acid sequence of SEQ ID NO: 2, a glycosyl moiety, and a 20 kDa polyethylene glycol (PEG), wherein the mutant FGF-21 peptide is attached to the glycosyl moiety by a covalent bond between a threonine at amino acid position 173 of SEQ ID NO: 2 and a first site of the glycosyl moiety and wherein the glycosyl moiety is attached to the 20 kDa PEG by a covalent bond between a second site of the glycosyl moiety and the 20 kDa PEG; (b) from 150 mM to 500 mM arginine; (c) from 0.01% to 0.1% (w/v) Polysorbate 80 (PS-80) or Polysorbate 20 (PS-20); (d) from 5 to 25 mM buffer, pH 7-8; and (e) a pharmaceutically acceptable carrier.

In some embodiments, the liquid pharmaceutical composition comprises: (a) from 10 mg/ml to 48 mg/ml of a mutant Fibroblast Growth Factor-21 (FGF-21) peptide conjugate comprising a mutant FGF-21 peptide comprising the amino acid sequence of SEQ ID NO: 2, a glycosyl moiety, and a 20 kDa polyethylene glycol (PEG), wherein the mutant FGF-21 peptide is attached to the glycosyl moiety by a covalent bond between a threonine at amino acid position 173 of SEQ ID NO: 2 and a first site of the glycosyl moiety and wherein the glycosyl moiety is attached to the 20 kDa PEG by a covalent bond between a second site of the glycosyl moiety and the 20 kDa PEG; (b) from 150 mM to 500 mM arginine, from 50 mM to 250 mM alanine, 50 mM to 250 mM proline, 50 mM to 250 mM glycine, 50 mM to 250 mM MgCl2, 1 to 5% (v/v) glycerol, 1 to 5% (v/v) PEG 400, or combination thereof; (c) from 0.01% to 0.1% (w/v) Polysorbate 80 (PS-80) or Polysorbate 20 (PS-20); (d) a buffer having a pH of 7-8; and (e) a pharmaceutically acceptable carrier.

In some embodiments, the liquid formulation, further comprises a surfactant. In some embodiments, the surfactant comprises cetrimonium bromide, sodium gluconate or combination thereof. In some embodiments, the liquid formulation comprises from 0.05% to 0.1% (w/v) cetrimonium bromide, from 0.05% to 0.1% (w/v) sodium gluconate or combination thereof.

In some embodiments, the buffer is Tris or phosphate buffer. In some embodiments, the liquid formulation comprises 20 mM Tris buffer. In some embodiments, the pH of the liquid formulation is from 7.0 to 7.5.

In some embodiments, the liquid pharmaceutical composition comprises from 20 to 44 mg/ml of the mutant FGF-21 peptide conjugate.

In some embodiments, the liquid pharmaceutical composition comprises from 150 mM to 275 mM arginine. In some embodiments, the arginine in the liquid pharmaceutical composition comprises arginine HCl, arginine sulfate or combination thereof. In some embodiments, the weight ratio of mutant FGF-21 peptide conjugate to arginine is from 0.6 to 0.9. In some embodiments, the molar ratio of mutant FGF-21 peptide conjugate to arginine is from about 0.006 to about 0.009.

In some embodiments, the liquid pharmaceutical composition comprises about 28 mg/mL mutant FGF-21 peptide conjugate, about 260 mM arginine HCl, about 20 mM Tris, 0.02% (w/v) PS-80 and wherein pH is about 7.1.

In some embodiments, the liquid pharmaceutical composition comprises about 20 mg/mL mutant FGF-21 peptide conjugate, about 150 mM arginine HCl, about 20 mM Tris, 0.02% (w/v) PS-80 and wherein pH is about 7.5.

In some embodiments, the liquid pharmaceutical composition comprises about 36 mg/mL mutant FGF-21 peptide conjugate, about 200 mM arginine HCl, about 20 mM Tris, 0.02% (w/v) PS-80 and wherein pH is about 7.1.

In some embodiments, the liquid pharmaceutical composition comprises about 44 mg/mL mutant FGF-21 peptide conjugate, about 200 mM arginine HCl, about 20 mM Tris, 0.02% (w/v) PS-80 and wherein pH is about 7.1.

In some embodiments, the liquid pharmaceutical composition comprises about 44 mg/mL mutant FGF-21 peptide conjugate, about 230 mM arginine HCl, about 20 mM Tris, 0.02% (w/v) PS-80 and wherein pH is about 7.1.

In some embodiments, the liquid formulation has an osmolality of about 250 mOsmol/kg to about 550 mOsmol/kg.

In some embodiments, the liquid formulation is a liquid formulation as described in U.S. Patent application publication No. 2022-0296678, which is incorporated by reference in its entirety.

In some embodiments, also encompassed herein is a pharmaceutical container comprising any one of or at least one of a mutant FGF-21 peptide conjugate described herein or a pharmaceutical composition comprising same. Exemplary such pharmaceutical containers include, without limitation, a syringe, vial, infusion bottle, ampoule, carpoule, a syringe equipped with a needle protection system, or a carpoule within an injection pen.

Method of Treating Severe Hypertriglyceridemia

Pegozafermin (PGZ) is a glycoPEGylated FGF21 analogue that has an N-terminal methionine residue, two point-mutations, and a single 20 kDa linear polyethylene glycol (PEG) covalently attached via a glycosyl moiety. PGZ data from a Phase 1b/2a POC study in subjects with NASH demonstrated overall metabolic benefit with improvements in lipids (TG, LDL, non-HDL and HDL), insulin resistance, HbA1c, body weight, and liver fat.

Severe hypertriglyceridemia (SHTG; ≥500 mg/dL) increases the risk of acute pancreatitis and cardiovascular disease. Current therapies rarely reduce TG levels to desired levels, highlighting the need for new therapeutic options. In some embodiments, the pharmaceutical compositions and methods provided herein reduces triglyceride levels by at least 20% from baseline, by at least 25% from baseline, by at least 30% from baseline, by at least 35% from baseline, by at least 40% from baseline.

In some embodiments, the administration significantly reduced TG, non-HDL-C, ApoB and liver fat, increased HDL-C with minimal change in LDL-C, and improved liver transaminases.

In some embodiments, the administration results in reduction of production of TG-rich lipoproteins.

In some embodiments, the administration results in improvement of clearance of TG-rich lipoproteins.

In some embodiments, the administration results in improvement of insulin sensitivity.

In some embodiments, the administration results in normalization of triglyceride levels to less than or equal to 150 mg/dl.

In some embodiments, the administration results in reduction of fasting plasma glucose by at least 10%, reduction of HBA1c by at least 0.2% or a combination thereof.

In some embodiments, the administration results in reduction of Alanine Transaminase (ALT) marker by at least 10%, reduction of Aspartate aminotransferase (AST) by at least 10%, median reduction of High-sensitivity C-reactive protein (hsCRP) by at least 10% or a combination thereof.

SHTG is commonly associated with obesity, metabolic syndrome, insulin resistance, type 2 diabetes mellitus and non-alcoholic fatty liver disease (NAFLD) An ideal therapy would not only lower TG levels but provide benefit for other metabolic comorbidities.

According to some aspects of the disclosure, administration of the mutant FGF-21 peptide conjugate significantly reduced TG and other atherogenic lipids in patients with SHTG. These results remained consistent in patients on background lipid modifying therapy (LMT) whether statin, statin combination, prescription fish oil, or fibrates. See FIGS. 7A-14. In some embodiments, administration of the mutant FGF-21 peptide conjugate provides cardiometabolic improvements (such as glycemic regulation and liver fat reduction).

In some embodiments, the method comprises administering the mutant FGF-21 peptide conjugate and background lipid modifying therapy (LMT) to the patient in need thereof.

Aspects of the disclosure relate to a method of treating severe hypertriglyceridemia (SHTG) in a subject in need thereof, comprising: administering once a week to the subject in need thereof a pharmaceutical composition comprising from about 9 mg to about 30 mg of a mutant Fibroblast Growth Factor-21 (FGF-21) peptide conjugate and a pharmaceutically acceptable carrier, wherein the mutant FGF-21 peptide conjugate comprises i) a mutant FGF-21 peptide comprising the amino acid sequence of SEQ ID NO: 2, ii) a glycosyl moiety, and iii) a 20 kDa polyethylene glycol (PEG), wherein the mutant FGF-21 peptide is attached to the glycosyl moiety by a covalent bond between a threonine at amino acid position 173 of SEQ ID NO: 2 and a first site of the glycosyl moiety and wherein the glycosyl moiety is attached to the 20 kDa PEG by a covalent bond between a second site of the glycosyl moiety and the 20 kDa PEG, wherein administration of the pharmaceutical composition results in a reduction of triglyceride levels by at least 20% from baseline. In some embodiments, the administration of the pharmaceutical composition results in a median reduction of triglyceride levels by at least 30% from baseline. In some embodiments, the administration of the pharmaceutical composition results in a median reduction of triglyceride levels by at least 40% from baseline.

In some embodiments, the administration results in normalization of triglyceride levels to less than or equal to 150 mg/dl.

In some embodiments, the administration results in a reduction of levels of non-HDL cholesterol by at least 10% from baseline, reduction of apoB by at least 10% from baseline, reduction of apoC3 by at least 10% from baseline, or a combination thereof.

In some embodiments, the administration results in an increase of the levels of HDL cholesterol by at least 10% from baseline, an increase of the levels of adiponectin by at least 10% from baseline or a combination thereof.

In some embodiments, the administration results in reduction of production of TG-rich lipoproteins.

In some embodiments, the administration results in improvement of clearance of TG-rich lipoproteins.

In some embodiments, the administration results in improvement of insulin sensitivity.

In some embodiments, the subject in need thereof has baseline hepatic steatosis.

In some embodiments, the administration results in reduction greater than 30% in liver fat.

In some embodiments, the method comprising administering the pharmaceutical composition to the subject in need thereof for 8 weeks or more.

In some embodiments, the pharmaceutical composition is administered sub-subcutaneously.

In some embodiments, the subject in need thereof is a human subject. In some embodiments, the subject in need thereof has fasting triglycerides (TG)≥500 mg/dL and ≤2000 mg/dL.

In some embodiments, the pharmaceutical composition comprises from about 9 mg to about 30 mg of the mutant FGF-21 peptide conjugate. For example, the pharmaceutical composition comprises about 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg of the mutant FGF-21 peptide conjugate.

In some embodiments, the pharmaceutical composition comprises from about 9 mg to about 14 mg, from about 15 mg to about 18 mg, from about 19 mg to about 26 mg, from about 27 mg to about 30 mg.

In some embodiments, the pharmaceutical composition comprises about 9 mg of the mutant FGF-21 peptide conjugate.

In some embodiments, the pharmaceutical composition comprises from about 15 mg to about 18 mg of the mutant FGF-21 peptide conjugate. In some embodiments, the pharmaceutical composition comprises about 15 mg of the mutant FGF-21 peptide conjugate. In some embodiments, the pharmaceutical composition comprises about 18 mg of the mutant FGF-21 peptide conjugate.

In some embodiments, the pharmaceutical composition comprises from about 27 mg to about 30 mg of the mutant FGF-21 peptide conjugate. In some embodiments, the pharmaceutical composition comprises about 27 mg of the mutant FGF-21 peptide conjugate. In some embodiments, the pharmaceutical composition comprises about 30 mg of the mutant FGF-21 peptide conjugate. In some embodiments, the administration results in reduction of Alanine Transaminase (ALT) marker by at least 10%, reduction of Aspartate aminotransferase (AST) by at least 10%, median reduction of High-sensitivity C-reactive protein (hsCRP) by at least 10% or a combination thereof. In some embodiments, the administration results in reduction of fasting plasma glucose by at least 10%, reduction of HBA1c by at least 0.2% or a combination thereof.

In some embodiments, the subject in need thereof is on background lipid-modifying therapy (LMT). In some embodiments, the LMT comprises statins, prescription fish oil, fibrates or combinations thereof. In some embodiments, the subject in need thereof is on background LMT and wherein the administration results in a reduction of levels of non-HDL cholesterol by at least 10% from baseline. In some embodiments, the subject in need thereof is on background LMT and wherein the administration results in a reduction of levels of apoB cholesterol by at least 10% from baseline.

Aspects of the disclosure relate to a method of treating severe hypertriglyceridemia (SHTG) in a subject in need thereof, comprising: administering once a week to the subject in need thereof a pharmaceutical composition comprising from about 27 mg to about 30 mg of a mutant Fibroblast Growth Factor-21 (FGF-21) peptide conjugate and a pharmaceutically acceptable carrier, wherein the mutant FGF-21 peptide conjugate comprises i) a mutant FGF-21 peptide comprising the amino acid sequence of SEQ ID NO: 2, ii) a glycosyl moiety, and iii) a 20 kDa polyethylene glycol (PEG), wherein the mutant FGF-21 peptide is attached to the glycosyl moiety by a covalent bond between a threonine at amino acid position 173 of SEQ ID NO: 2 and a first site of the glycosyl moiety and wherein the glycosyl moiety is attached to the 20 kDa PEG by a covalent bond between a second site of the glycosyl moiety and the 20 kDa PEG, wherein administration of the pharmaceutical composition results in a reduction of triglyceride levels by at least 20% from baseline, and wherein administration of the pharmaceutical composition results in one or more of the following: reduction of Alanine Transaminase (ALT) marker by at least 10% from baseline, reduction of Aspartate aminotransferase (AST) by at least 10% from baseline, median reduction of High-sensitivity C-reactive protein (hsCRP) by at least 10% from baseline, reduction of fasting plasma glucose by at least 10% from baseline, reduction of HBA1c by at least from baseline, reduction of levels of non-HDL cholesterol by at least 10% from baseline, reduction of apoB by at least 10% from baseline, reduction of apoC3 by at least 10% from baseline, increase of the levels of HDL cholesterol by at least 10% from baseline, increase of the levels of adiponectin by at least 10% from baseline, and reduction greater than 30% in liver fat from baseline.

Other aspects of the disclosure relate to a method of treating severe hypertriglyceridemia (SHTG) in a subject in need thereof, comprising administering once every two weeks to the subject in need thereof a pharmaceutical composition comprising from about 31 mg to about 44 mg of a mutant Fibroblast Growth Factor-21 (FGF-21) peptide conjugate and a pharmaceutically acceptable carrier, wherein the mutant FGF-21 peptide conjugate comprises i) a mutant FGF-21 peptide comprising the amino acid sequence of SEQ ID NO: 2, ii) a glycosyl moiety, and iii) a 20 kDa polyethylene glycol (PEG), wherein the mutant FGF-21 peptide is attached to the glycosyl moiety by a covalent bond between a threonine at amino acid position 173 of SEQ ID NO: 2 and a first site of the glycosyl moiety and wherein the glycosyl moiety is attached to the 20 kDa PEG by a covalent bond between a second site of the glycosyl moiety and the 20 kDa PEG, wherein administration of the pharmaceutical composition results in a reduction of triglyceride levels by at least 20% from baseline.

In some embodiments, the administration of the pharmaceutical composition results in a median reduction of triglyceride levels by at least 30% from baseline.

In some embodiments, the administration of the pharmaceutical composition results in a median reduction of triglyceride levels by at least 40% from baseline.

In some embodiments, the pharmaceutical composition comprises from about 31 mg to about 44 mg of the mutant FGF-21 peptide conjugate. In some embodiments, the pharmaceutical composition comprises from about 31 mg to about 35 mg of the mutant FGF-21 peptide conjugate. In some embodiments, the pharmaceutical composition comprises from about 36 mg to about 44 mg of the mutant FGF-21 peptide conjugate. For example, the pharmaceutical composition comprises about 31 mg, 32 mg, 33 mg, 34 mg, 35 mg, 36 mg, 37 mg, 38 mg, 39 mg, 40 mg, 41 mg, 42 mg, 43 mg, 44 mg of the mutant FGF-21 peptide conjugate.

In some embodiments, the administration results in normalization of triglyceride levels to less than or equal to 150 mg/dl.

In some embodiments, the administration results in a reduction of levels of non-HDL cholesterol by at least 10% from baseline, reduction of apoB by at least 10% from baseline, reduction of apoC3 by at least 10% from baseline, or a combination thereof.

In some embodiments, the administration results in an increase of the levels of HDL cholesterol by at least 10% from baseline, an increase of the levels of adiponectin by at least 10% from baseline or a combination thereof.

In some embodiments, the administration results in reduction of production of TG-rich lipoproteins.

In some embodiments, the administration results in improvement of clearance of TG-rich lipoproteins.

In some embodiments, the administration results in improvement of insulin sensitivity.

In some embodiments, the subject in need thereof has baseline hepatic steatosis.

In some embodiments, the administration results in reduction greater than 30% in liver fat.

In some embodiments, the method comprising administering the pharmaceutical composition to the subject in need thereof for 8 weeks or more.

In some embodiments, the subject in need thereof is a human subject.

In some embodiments, the subject in need thereof has fasting triglycerides (TG) ≥500 mg/dL and ≤2000 mg/dL.

In some embodiments, the pharmaceutical composition comprises from about 36 mg to about 44 mg of the mutant FGF-21 peptide conjugate. In some embodiments, the administration results in median reduction of hsCRP by at least 10%.

In some embodiments, the subject in need thereof is on background lipid-modifying therapy (LMT). In some embodiments, the LMT comprises statins, prescription fish oil, fibrates or combinations thereof. In some embodiments, the subject in need thereof is on background LMT and wherein the administration results in a reduction of levels of non-HDL cholesterol by at least 10% from baseline. In some embodiments, the subject in need thereof is on background LMT and wherein the administration results in a reduction of levels of apoB cholesterol by at least 10% from baseline.

In some embodiments, the pharmaceutical composition is administered sub-subcutaneously.

Aspects of the disclosure relate to a method of treating severe hypertriglyceridemia (SHTG) in a subject in need thereof, comprising: administering once every two weeks to the subject in need thereof a pharmaceutical composition comprising from about 36 mg to about 44 mg of a mutant Fibroblast Growth Factor-21 (FGF-21) peptide conjugate and a pharmaceutically acceptable carrier, wherein the mutant FGF-21 peptide conjugate comprises i) a mutant FGF-21 peptide comprising the amino acid sequence of SEQ ID NO: 2, ii) a glycosyl moiety, and iii) a 20 kDa polyethylene glycol (PEG), wherein the mutant FGF-21 peptide is attached to the glycosyl moiety by a covalent bond between a threonine at amino acid position 173 of SEQ ID NO: 2 and a first site of the glycosyl moiety and wherein the glycosyl moiety is attached to the 20 kDa PEG by a covalent bond between a second site of the glycosyl moiety and the 20 kDa PEG, wherein administration of the pharmaceutical composition results in a reduction of triglyceride levels by at least 20% from baseline, and wherein administration of the pharmaceutical composition results in one or more of the following:

median reduction of High-sensitivity C-reactive protein (hsCRP) by at least 10% from baseline, reduction of levels of non-HDL cholesterol by at least 10% from baseline, reduction of apoB by at least 10% from baseline, reduction of apoC3 by at least 10% from baseline, increase of the levels of HDL cholesterol by at least 10% from baseline, increase of the levels of adiponectin by at least 10% from baseline, and reduction greater than 30% in liver fat from baseline.

In some embodiments, the glycosyl moiety of the FGF-21 peptide conjugate comprises at least one of an N-acetylgalactosamine (GalNAc) residue, a galactose (Gal) residue, a sialic acid (Sia) residue, a 5-amine analogue of a Sia residue, a mannose (Man) residue, mannosamine, a glucose (Glc) residue, an N-acetylglucosamine (GlcNAc) residue, a fucose residue, a xylose residue, or a combination thereof.

In some embodiments, the glycosyl moiety of the FGF-21 peptide conjugate comprises at least one N-acetylgalactosamine (GalNAc) residue, at least one galactose (Gal) residue, at least one sialic acid (Sia) residue, or a combination thereof. In some embodiments, the at least one Sia residue is a nine-carbon carboxylated sugar. In some embodiments, the at least one Sia residue is N-acetylneuraminic acid (2-keto-5-acetamido-3,5-dideoxy-D-glycero-D-galactononulopyranos-1-onic acid (Neu5Ac), N-glycolylneuraminic acid (Neu5Gc), 2-keto-3-deoxy-nonulosonic acid (KDN), or a 9-substituted sialic acid. In some embodiments, the 9-substituted sialic acid is 9-O-lactyl-NeuSAc, 9-O-acetyl-NeuSAc, 9-deoxy-9-fluoro-Neu5Ac, or 9-azido-9-deoxy-Neu5Ac.

In some embodiments, the glycosyl moiety of the FGF-21 peptide conjugate comprises the structure -GalNAc-Sia-.

In some embodiments, the 20 kDa PEG moiety is attached to the glycosyl moiety by a covalent bond to a linker, wherein the linker comprises at least one amino acid residue. In some embodiments, the at least one amino acid residue is a glycine (Gly).

In some embodiments, the mutant FGF-21 peptide conjugate comprises the structure -GalNAc-Sia-Gly-PEG (20 kDa).

In some embodiments, the 20 kDa PEG of the FGF-21 peptide conjugate is a linear or branched PEG. In some embodiments, the 20 kDa PEG is a 20 kDa methoxy-PEG.

In some embodiments, the mutant FGF-21 peptide conjugate comprises the structure:

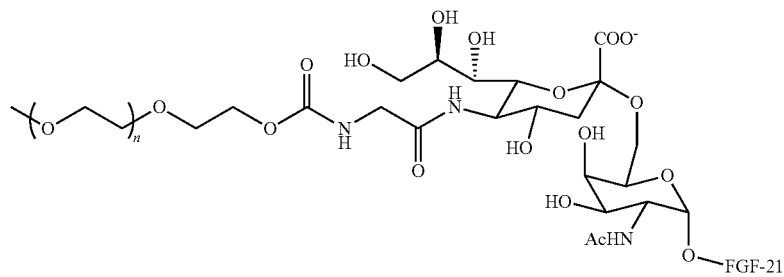

wherein n is an integer selected from 450 to 460.

Without being bound to the theory, FGF-21 conjugate of the disclosure is an attractive therapy in severe hypertriglyceridemia with the potential to address multiple co-morbidities simultaneously, including cardiac, glycemic, and hepatic risks.

Specific examples of methods and kits have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

The embodiments of the invention described above are intended to be exemplary only. Those skilled in this art will understand that various modifications of detail may be made to these embodiments, all of which come within the scope of the invention.

All publications mentioned herein are hereby incorporated by reference in their entireties. While the foregoing invention has been described in some detail for purposes of clarity and understanding, it will be appreciated by one skilled in the art from a reading of the disclosure that various changes in form and detail can be made without departing from the true scope of the invention in the appended claims.

EXAMPLES

Example 1

Randomized Phase 2 Trial of Pegozafermin in Severe Hypertriglyceridemia

Summary of Randomized Phase 2 Trial of Pegozafermin in Severe Hypertriglyceridemia
Background
Pegozafermin is a long-acting glycopegylated recombinant analog of human fibroblast growth factor 21 in development for severe hypertriglyceridemia and non-alcoholic steatohepatitis.

Methods
ENTRIGUE was a phase 2, double-blind, randomized, 5-arm trial of pegozafermin at 4 different doses versus placebo for 8 weeks in patients with triglycerides ≥500 mg/dL and ≤2000 mg/dL. The primary endpoint was percent change in triglycerides from baseline. Prespecified secondary endpoints included other lipids, a magnetic resonance imaging liver fat fraction sub-study, and markers of insulin sensitization and inflammation.
Results
A total of 85 patients were randomized and treated (18 to placebo and 67 to 4 different doses of pegozafermin; 55% of patients on background lipid-lowering therapy; mean baseline triglycerides, 733 mg/dL). There were significant reductions in median triglycerides for the pooled pegozafermin doses versus placebo (57.3% versus 11.9%, difference of 45.4%, 95% confidence interval (CI): 30.3%, 57.1%; p<0.001), as well as in all 4 treatment arms versus placebo, with reductions ranging from 36.4% to 63.4%. Results were consistent in those on or not on background lipid lowering therapy. Mean apoB and non-HDL-C changed by −10.5% and −18.3% on pooled doses versus 1.1% and −0.6% on placebo (p=0.019 and p=0.007, respectively). Liver fat (n=23) was significantly reduced for the pooled arms versus placebo (34.8%, p=0.012). There were no serious adverse events related to study drug.
Conclusions
Pegozafermin reduced triglycerides, non-HDL-C, apoB, and liver fat fraction. If these results are confirmed in a phase 3 trial, pegozafermin could be a promising treatment for severe hypertriglyceridemia.

Severe hypertriglyceridemia (SHTG; ≥500 mg/dL) increases risk for both acute pancreatitis and cardiovascular disease.[1-10] Although lifestyle modification strategies are often recommended as first-line treatment, triglyceride (TG) levels often remain elevated and require pharmacologic treatment in almost all patients.[11-13] Current therapies for severe hypertriglyceridemia rarely reduce TGs to desired levels, highlighting the need for new therapeutic options. Moreover, as SHTG is commonly associated with obesity, metabolic syndrome, insulin resistance, type 2 diabetes mellitus (T2DM) and non-alcoholic fatty liver disease (NAFLD),[12,14-16] an ideal therapy should not only lower TG levels, but also provide benefit for other metabolic comorbidities.

Fibroblast growth factor 21 (FGF21) is an endogenous stress hormone that regulates lipid and glucose metabolism and energy expenditure. FGF21 is thought to reduce TG by decreasing de novo lipogenesis in the liver, inhibiting release of free fatty acids from adipose tissue, and increasing free fatty acid oxidation in muscle and liver.[17-20] Pegozafermin is a glycopegylated recombinant analog of human FGF21 designed to have a longer half-life than native FGF21 while recapitulating the receptor activity profile of the native hormone. It is being developed for SHTG and non-alcoholic steatohepatitis (NASH). Pegozafermin has previously demonstrated efficacy on serum lipids (TG, LDL, non-HDL and HDL), insulin resistance, HbA1c, body weight, and liver fat, albeit in a NASH population.[21,22] Though previous clinical trials with pegozafermin and other FGF21 analogs have consistently demonstrated improvements in lipids in both healthy volunteers as well as patients with NASH or diabetes, FGF21 analogs have not been assessed in SHTG.[21,23-27] The ENTRIGUE trial was designed to investigate pegozafermin as a novel therapeutic agent for the treatment of SHTG.

Methods

Trial Design

The ENTRIGUE trial was a randomized, double-blind, placebo-controlled, dose-ranging, phase 2 trial designed to assess the efficacy, safety and tolerability of pegozafermin administered subcutaneously once-weekly (QW) or every 2 weeks (Q2W) in participants with SHTG. Participants with screening fasting TG≥500 mg/dL (5.6 mmol/L) and ≤2000 mg/dL (22.6 mmol/L) were eligible to enroll regardless of background lipid-modifying therapy of statins, prescription omega-3 fatty acids and fibrates. Participants were enrolled into one of two cohorts: 1) main study cohort (could not be on concurrent fibrate therapy); or 2) fibrate cohort.

Figure 4:
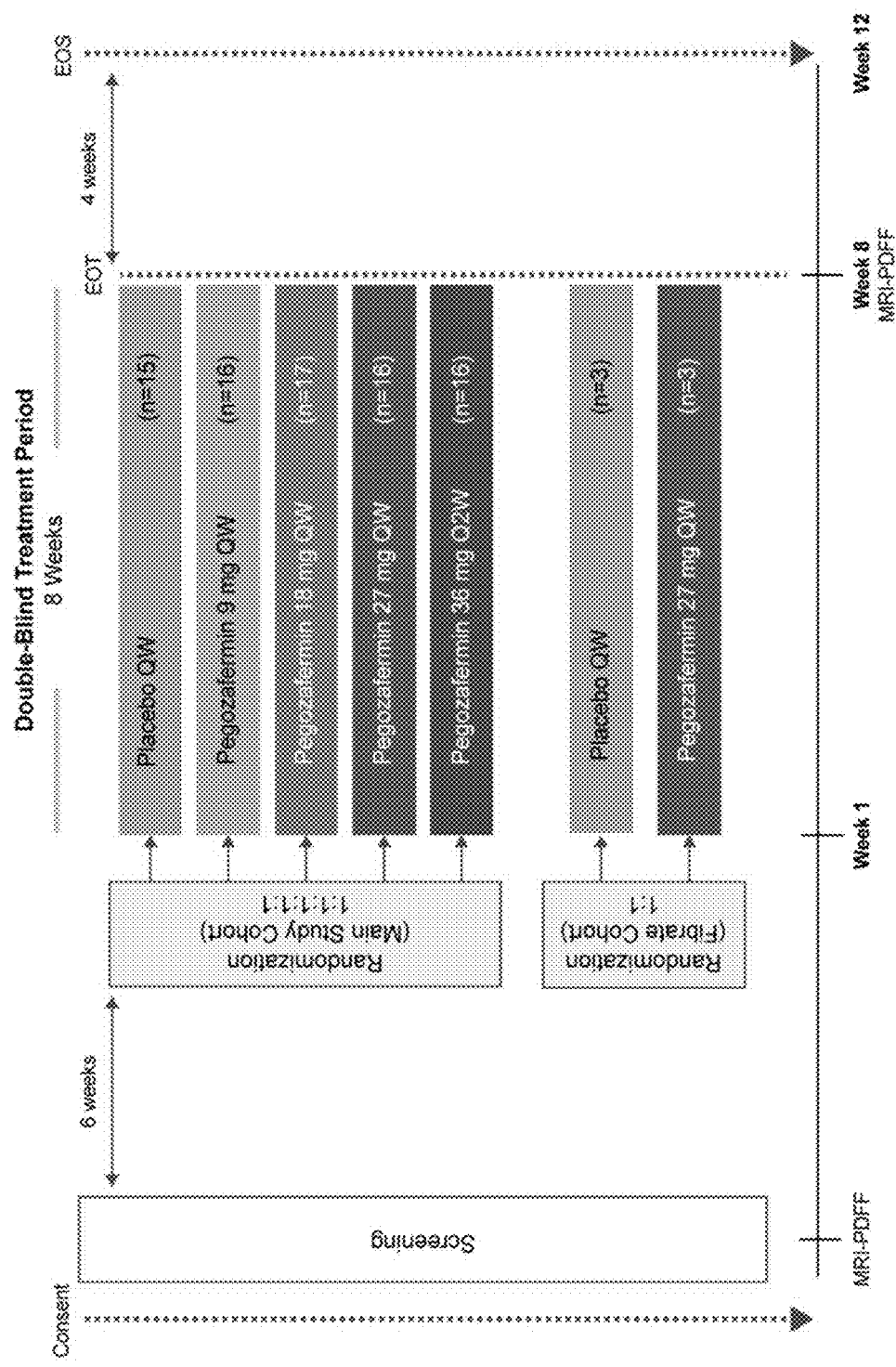
FIG. 4 is a diagram showing the main study cohort was randomized 1:1:1:1:1 to one of four doses of pegozafermin (9 mg QW, 18 mg QW, 27 mg QW or 36 mg Q2W) or placebo, and the fibrate cohort was randomized 1:1 to either pegozafermin 27 mg QW or placebo QW for 8 weeks.

The main study cohort was randomized 1:1:1:1:1 to one of four doses of pegozafermin (9 mg QW, 18 mg QW, 27 mg QW or 36 mg Q2W) or placebo, and the fibrate cohort was randomized 1:1 to either pegozafermin 27 mg QW or placebo QW for 8 weeks (FIG. 4). All participants were stratified by TG level (<750 mg/dL or ≥750 mg/dL [8.5 mmol/L]) with additional stratification in the main study by whether they were taking background therapy. A magnetic resonance imaging proton density fat fraction (MRI-PDFF) sub-study was conducted at sites able to perform MRI-PDFF imaging, and participants in the fibrate cohort were required to have MRI-PDFF≥6.0% at enrollment. After completing the 8-week treatment period, participants underwent a 4-week safety follow-up period.

Participants were required to fast for 12-14 hours and abstain from alcohol for 48 hours prior to each lipid assessment throughout the study. Following a lifestyle stabilization period (4 weeks if on stable approved lipid-modifying therapy; up to 6 weeks if washing out ineligible lipid-modifying therapy), an ~2-week qualification period occurred consisting of two fasting TG assessments at least one week apart. If mean TG levels from these two laboratory evaluations were not within the inclusion range, an additional third assessment was collected at least one week apart from the previous assessment. The mean TG value from the last two assessments served as TG qualification for the study and was the basis for participant TG stratification at randomization. Exclusion criteria included uncontrolled or recent diagnosis of hypertension, uncontrolled or recent diagnosis of T2DM within 6 months of screening, BMI>45 kg/m², or cardiovascular or cerebrovascular disease. Additional qualification and full exclusion criteria are provided in the study protocol.

The trial was conducted at 50 clinical sites in the United States, Hungary, Poland and Czech Republic from September 2020 to June 2022. The trial was approved by the Institutional Review Board or Ethics Committee at each site. Participants provided written informed consent. All authors had access to trial data, participated in the preparation of the manuscript, and assume responsibility for the data and analyses.

Study Outcomes

The study objectives and endpoints were similar for the main study and fibrate cohorts. A small number of patients enrolled in the fibrate cohort (n=6) therefore data were pooled and presented for both cohorts. The primary efficacy endpoint was percentage change in serum TG from baseline to week 8. Secondary efficacy endpoints included select serum lipids and lipoproteins, metabolic markers, and change in liver fat content as assessed by MRI-PDFF. Safety endpoints included overall safety and tolerability assessments, liver function markers and immunogenicity.

Baseline TG level was defined as the average of randomization day assessment collected pre-dose and the preceding two lipid-qualifying assessments collected during the TG qualifying period. The TG value at week 8 was defined as the average of TG values at week 7 and week 8. In case of missing TG values at week 7 or 8, the non-missing result was used as the week 8TG value. Responder analysis of TG reduction at various threshold levels was performed and proportion of participants with TG normalization (<150 mg/dL) was also analyzed.

Statistical Analysis

The study was designed to have at least 86% power to detect a 45% difference in TG between each of the pegozafermin arms and placebo groups, assuming 50% reduction in pegozafermin dose groups and 5% reduction in the placebo group. Both pooled pegozafermin from all dose groups and individual pegozafermin dose groups were compared to placebo. All analysis were performed at the two-sided alpha level of 0.05 without adjustment for multiplicity, and confidence intervals (CI) were two-sided (95%). Summary descriptive statistics were used to present demographics and baseline characteristics, safety endpoints, and pharmacodynamic parameters.

Figure 5:
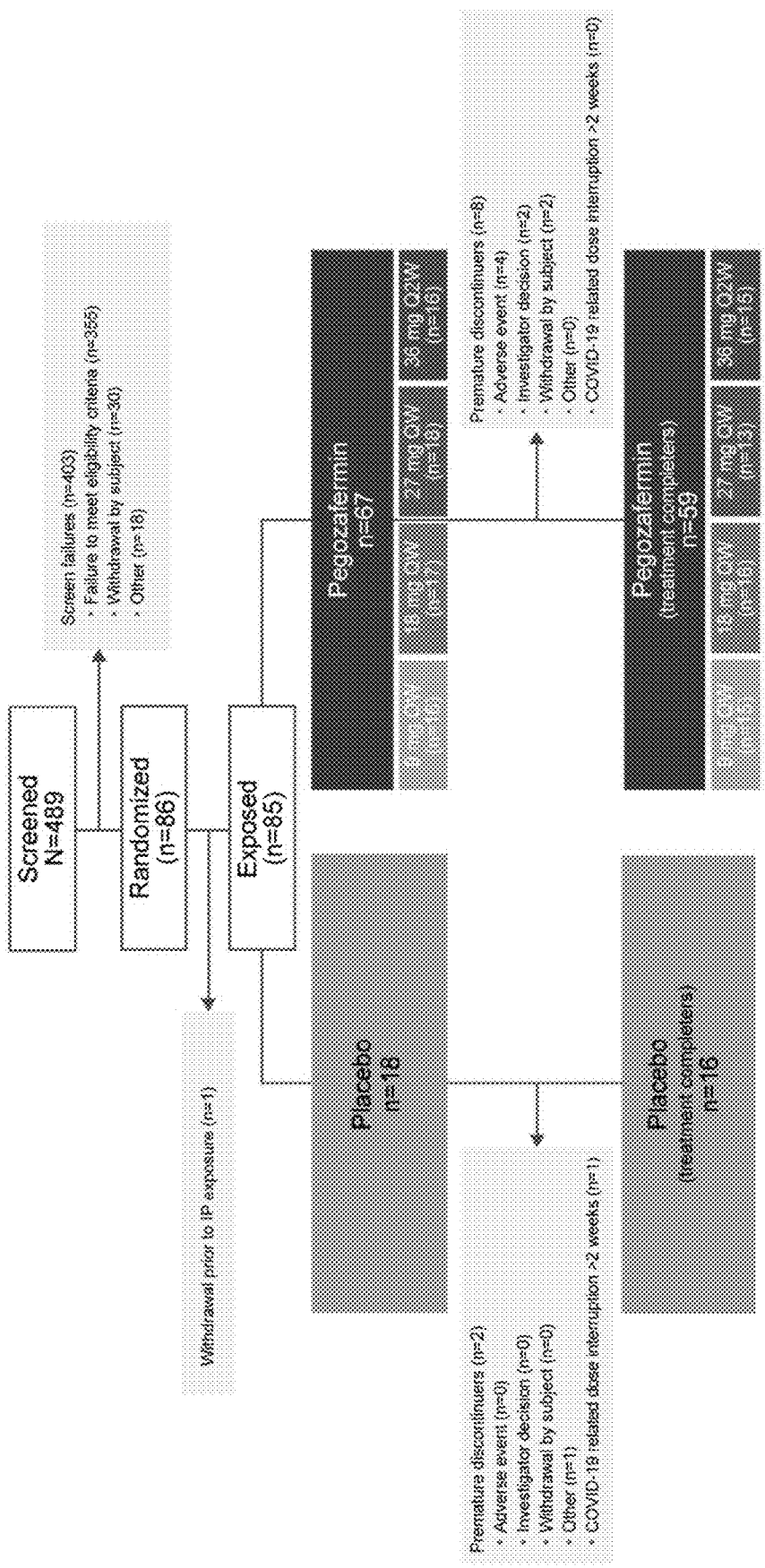
FIG. 5 is a diagram showing the patient disposition and population analysis sets.

Patient disposition and population analysis sets are presented in FIG. 5 and Table 3.

TABLE 3

| Population | Definition | n (%) |
|---|---|---|
| Screened Analysis Set | All participants who signed informed consent underwent screening. | 489 |
| Randomized Analysis Set | All participants in screened analysis set who were assigned a randomization number in the study. | 86 (100%) |
| Full Analysis Set | All randomized participants who received at least 1 dose of investigational product, had a baseline, and at least 1 post-baseline TG measurement, not including end-of-study visit. | 82 (95.3%) |
| Safety Analysis Set | All participants who received at least 1 dose of investigational product. | 85 (98.8%) |
| MRI-PDFF Analysis Set | All participants in the Full Analysis Set who had baseline and a follow up MRI-PDFF assessment. | 23 (26.7%) |

The primary efficacy analysis was performed using a non-parametric van Elteren test, stratified by baseline TG level and background lipid therapy to test the treatment difference using pooled data based on the full analysis set. The location shift estimate and Hodges-Lehmann 2-tailed 95% CI are presented. Comparison between the individual pegozafermin dose group and placebo used the unstratified Wilcoxon rank-sum test due to low sample size. If the proportion of participants within any subgroup was less than 33% of the overall cohort, only descriptive analysis was performed.

Secondary efficacy endpoints were analyzed by mixed model repeated measurements. If the mixed model assumption was severely violated, non-parametric methods were used for the analysis. The proportion of participants with TG<500 mg/dL at week 8 were analyzed using stratified Cochran Mantel Haenszel (CMH) method using patients with both baseline and week 8 TG results. Unstratified chi-square test was performed for comparisons between placebo and the individual pegozafermin dose group. There was no adjustment for multiple testing in this phase 2 study. Statistical analysis was performed using SAS®, version 9.4 or later. Full description of study endpoints and pre-specified analyses are provided in the study protocol and statistical analysis plan.

Results

Patient Characteristics

A total of 489 patients underwent screening, with 85 patients (17.4%) randomized and treated (18 to placebo; 67 to 4 different doses of pegozafermin). Among the subjects treated with pegozafermin, the distribution was as follows: 9 mg QW, n=16; 18 mg QW, n=17; 27 mg QW, n=18; and 36 mg Q2W, n=16. The baseline characteristics of the patients, shown in Table 1, were reasonably balanced across groups, with a mean age of 53.7 years, 75.3% male, mean BMI 33.1 kg/m 2, 50.6% with T2DM, 55.3% on background lipid-lowering therapy (including statins, prescription omega-3 fatty acids, fibrates, bempedoic acid, and ezetimibe) and a mean baseline TG level of 732.5 mg/dL. Other baseline lipids were at typical levels for this population: LDL-C, 89.1 mg/dL; HDL-C, 28.4 mg/dL; and non-HDL-C, 211.5 mg/dL. At clinical sites with MRI capability, a subset of patients (n=24) underwent proton density fat-fraction (PDFF) evaluation to measure hepatic steatosis. All patients assessed by MRI-PDFF had evidence of fatty liver (>5% hepatic fat) at baseline, with an overall mean value of 20.1% (Table 1).

TABLE 1

| Characteristic Mean or % | Placebo (n = 18) | PGZ Pooled (n = 67) | PGZ 9 mg QW (n = 16) | PGZ 18 mg QW (n = 17) | PGZ 27 mg QW (n = 18) | PGZ 36 mg Q2W (n = 16) | Total (n = 85) |
|---|---|---|---|---|---|---|---|
| Age (years) | 57.5 | 52.7 | 54.6 | 49.2 | 53.9 | 53.1 | 53.7 |
| Male (%) | 66.7 | 77.6 | 68.8 | 82.4 | 72.2 | 87.5 | 75.3 |
| White (%) | 94.4 | 95.5 | 93.8 | 100 | 100 | 87.5 | 95.3 |
| BMI (kg/m$^2$) | 33.1 | 33.1 | 32.9 | 32.3 | 34.2 | 32.9 | 33.1 |
| Type 2 diabetes, n (%) | 11 (61.1) | 32 (47.8) | 9 (56.3) | 6 (35.3) | 10 (55.6) | 7 (43.8) | 43 (50.6) |
| Hypertension, n (%) | 13 (72.2) | 39 (58.2) | 11 (68.8) | 7 (41.2) | 11 (61.1) | 10 (62.5) | 52 (61.2) |
| Triglyceride (mg/dL) | 720.3 | 735.8 | 721.7 | 709.5 | 680.3 | 840.3 | 732.5 |
| Triglyceride <750 mg/dL at screening (%) | 66.7 | 59.7 | 62.5 | 58.8 | 61.1 | 56.3 | 61.2 |
| Triglyceride ≥750 mg/dL at screening (%) | 33.3 | 40.3 | 37.5 | 41.2 | 38.9 | 43.8 | 38.8 |
| non-HDL cholesterol (mg/dL) | 219.6 | 209.3 | 216.2 | 203.2 | 203.4 | 215.4 | 211.5 |
| HDL cholesterol (mg/dL) | 28.3 | 28.4 | 30.7 | 27.3 | 30.6 | 24.8 | 28.4 |
| LDL cholesterol (mg/dL) | 87.9 | 89.4 | 91.6 | 88.3 | 97.3 | 79.5 | 89.1 |
| VLDL cholesterol (mg/dL) | 133.2 | 117.8 | 123.2 | 115.0 | 104.7 | 130.1 | 120.9 |
| VLDL triglyceride (mg/dL) | 610.2 | 633.6 | 588.0 | 574.2 | 590.0 | 791.4 | 628.9 |
| Total cholesterol (mg/dL) | 247.9 | 237.6 | 246.9 | 230.5 | 234.0 | 240.1 | 239.8 |
| Apolipoprotein B (mg/dL) | 116.3 | 115.3 | 120.1 | 115.3 | 119.3 | 105.9 | 115.5 |
| Apolipoprotein C3 (mg/dL) | 29.7 | 29.5 | 29.4 | 28.0 | 30.7 | 30.0 | 29.6 |
| Apolipoprotein A1 (mg/dL) | 138.8 | 137.1 | 143.3 | 137.7 | 141.0 | 125.9 | 137.5 |
| Lipoprotein (a) (nmol/L) | 42.5 | 45.4 | 48.2 | 21.1 | 55.1 | 58.3 | 44.8 |
| Free fatty acids (mmol/L) | 0.6 | 0.5 | 0.5 | 0.6 | 0.6 | 0.5 | 0.5 |
| HbA1c (%) | 6.28 | 6.55 | 6.63 | 6.59 | 6.61 | 6.37 | 6.50 |
| HbA1c ≥6.5%, n (%) | 7 (38.9) | 30 (44.8) | 9 (56.3) | 6 (35.3) | 9 (50.0) | 6 (37.5) | 37 (43.5) |
| High-sensitivity C-reactive protein (mg/L) | 4.6 | 4.5 | 5.9 | 3.6 | 3.2 | 5.7 | 4.6 |
| Adiponectin (µg/mL) | 4.0 | 3.3 | 3.3 | 2.4 | 4.9 | 2.5 | 3.5 |
| Fasting plasma glucose (mg/dL) | 124.4 | 148.7 | 158.5 | 139.3 | 157.0 | 139.0 | 143.6 |
| ALT (U/L) | 29.1 | 33.9 | 36.3 | 36.9 | 33.0 | 29.2 | 32.8 |
| AST (U/L) | 24.2 | 24.7 | 26.7 | 27.6 | 23.7 | 20.6 | 24.6 |
| Any background lipid-modifying therapy, n (%) | 11 (61.1) | 36 (53.7) | 8 (50.0) | 9 (52.9) | 11 (61.1) | 8 (50.0) | 47 (55.3) |
| Statins | 9 (50.0) | 29 (43.3) | 6 (37.5) | 9 (52.9) | 7 (38.9) | 7 (43.8) | 38 (44.7) |
| High intensity statins | 4 (22.2) | 17 (25.4) | 6 (37.5) | 5 (29.4) | 4 (22.2) | 2 (12.5) | 21 (24.7) |
| Prescription fish oils | 2 (11.1) | 10 (14.9) | 1 (6.3) | 2 (11.8) | 4 (22.2) | 3 (18.8) | 12 (14.1) |
| Fibrates | 3 (16.7) | 3 (4.5) | 0 | 0 | 3 (16.7) | 0 | 6 (7.1) |

TABLE 1-continued

| Characteristic Mean or % | Placebo (n = 18) | PGZ Pooled (n = 67) | PGZ 9 mg QW (n = 16) | PGZ 18 mg QW (n = 17) | PGZ 27 mg QW (n = 18) | PGZ 36 mg Q2W (n = 16) | Total (n = 85) |
|---|---|---|---|---|---|---|---|
| Ezetimibe | 1 (5.6) | 8 (11.9) | 2 (12.5) | 2 (11.8) | 2 (11.1) | 2 (12.5) | 9 (10.6) |
| Bempedoic acid | 0 | 1 (1.5) | 0 | 1 (5.9) | 0 | 0 | 1 (1.2) |
| Liver fat fraction by MRI-PDFF (%) (n = 24) | 16.5 [n = 6] | 21.3 [n = 18] | 19.8 [n = 3] | 18.0 [n = 5] | 22.4 [n = 7] | 25.5 [n = 3] | 20.1 [n = 24] |

Efficacy Endpoints
Effect on Triglyceride Levels (Primary Endpoint)

Figure 1B:
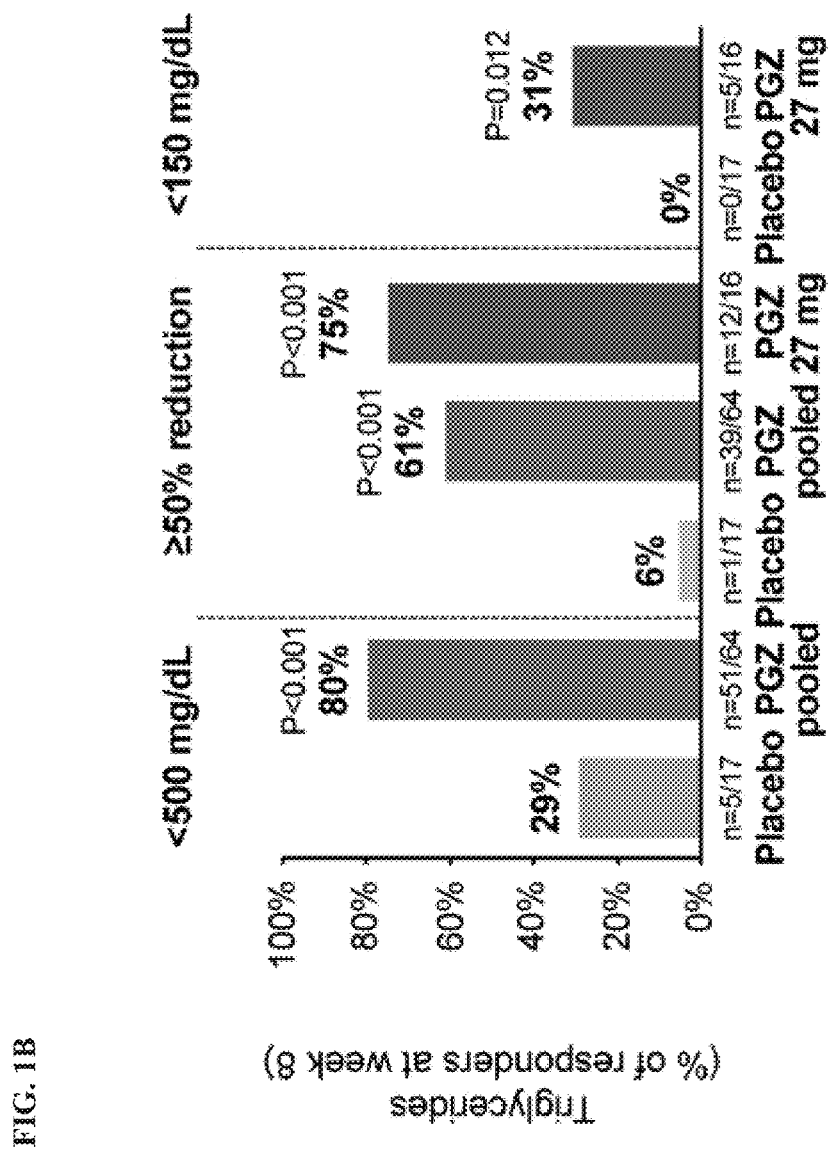
Figure 1C:
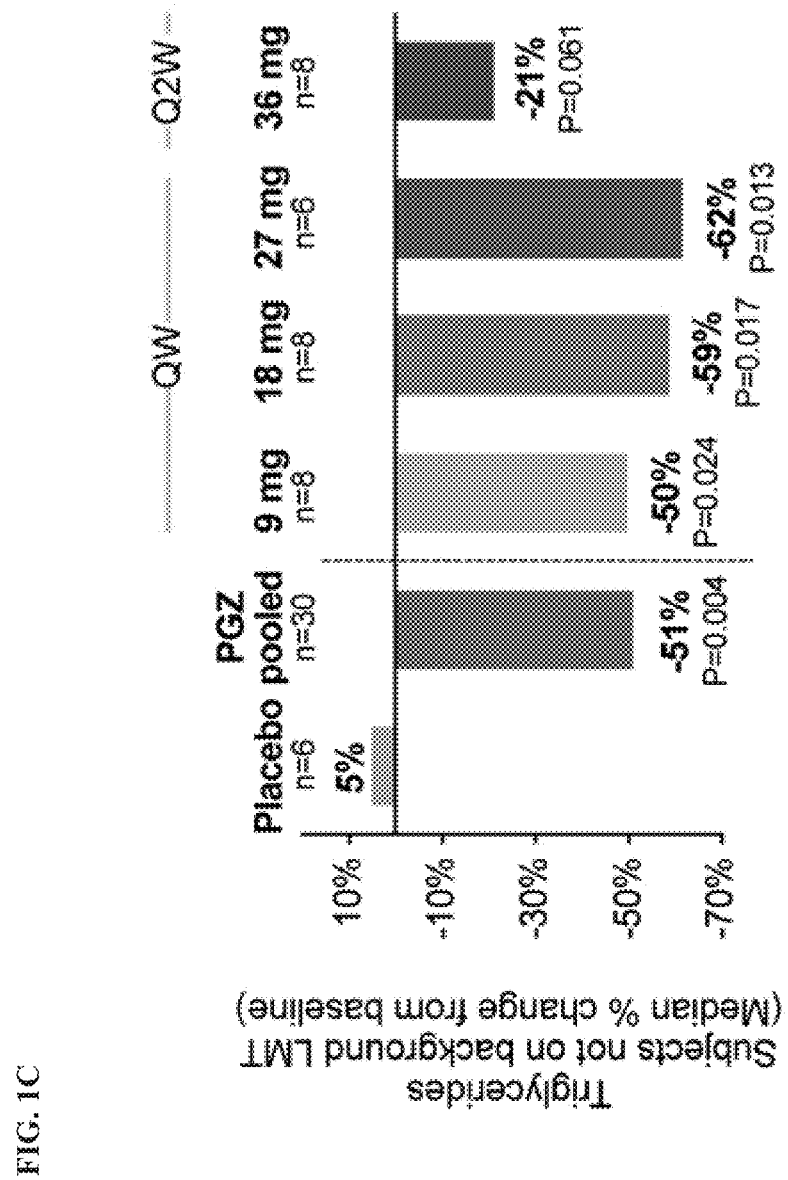
Figure 1D:
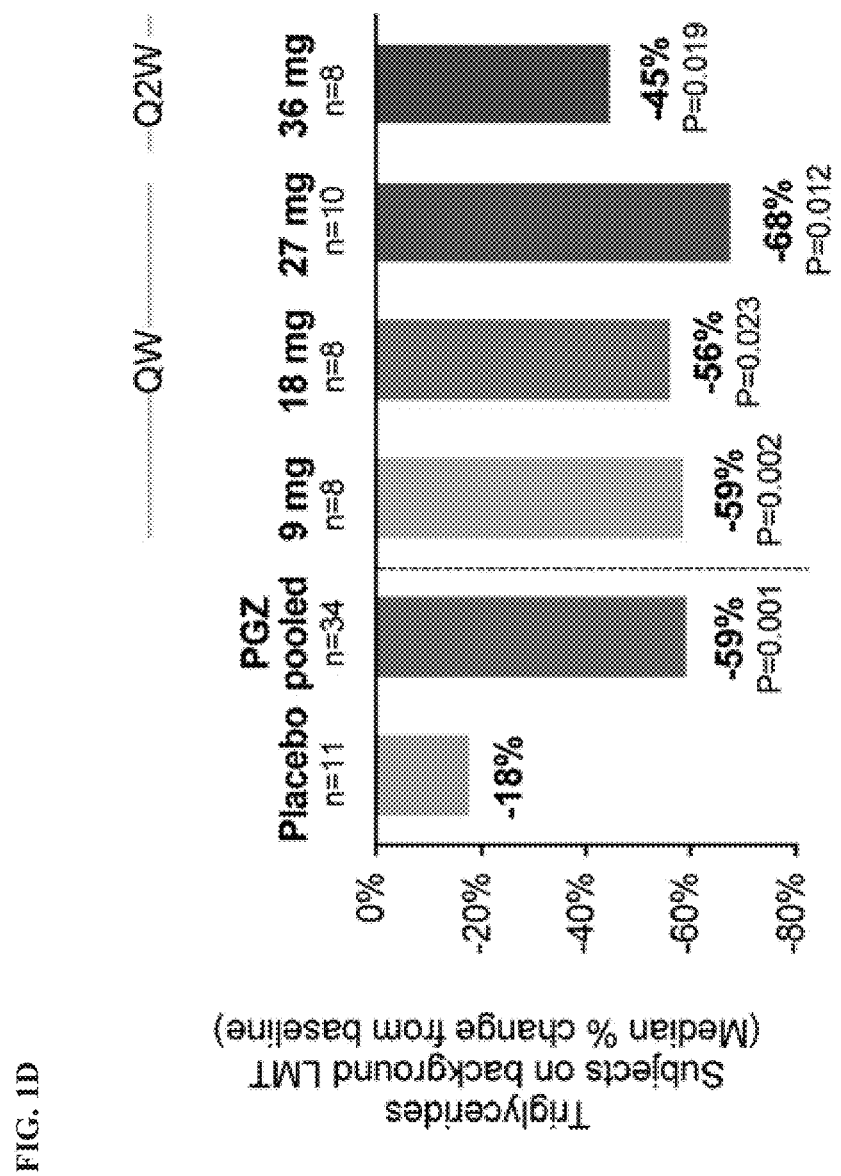
Figure 1E:
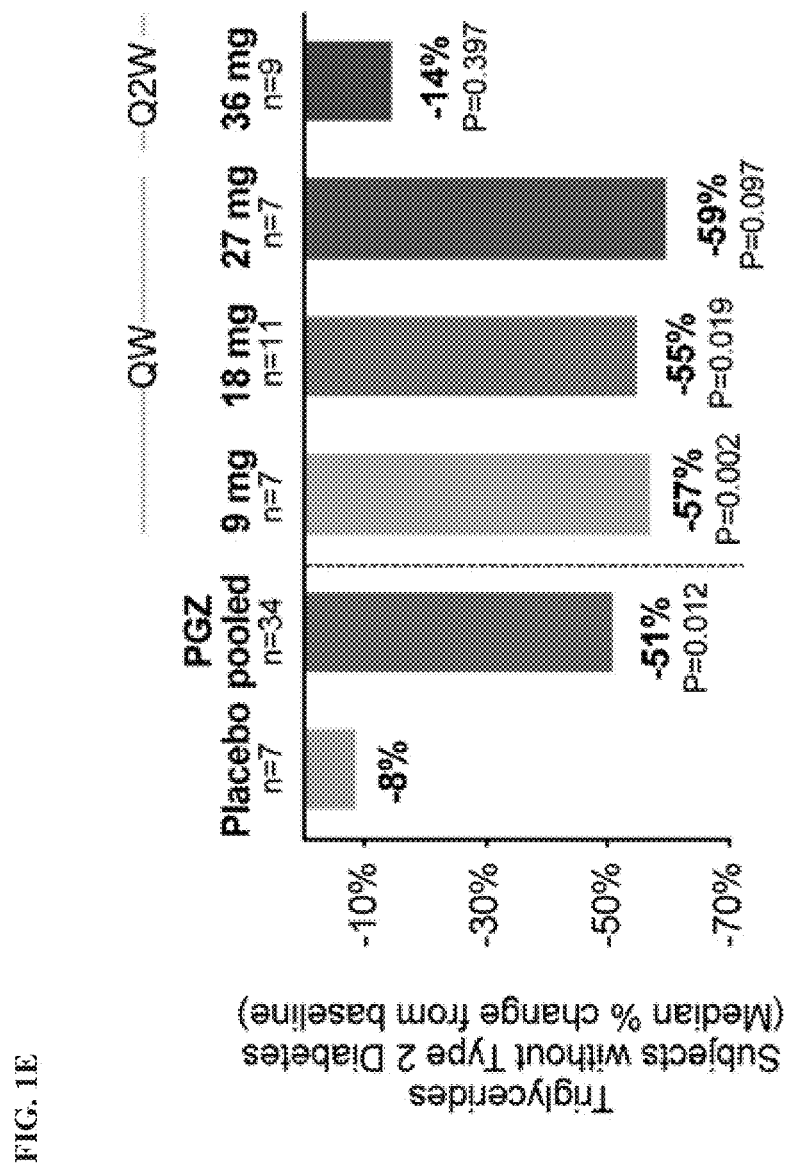
Figure 1F:
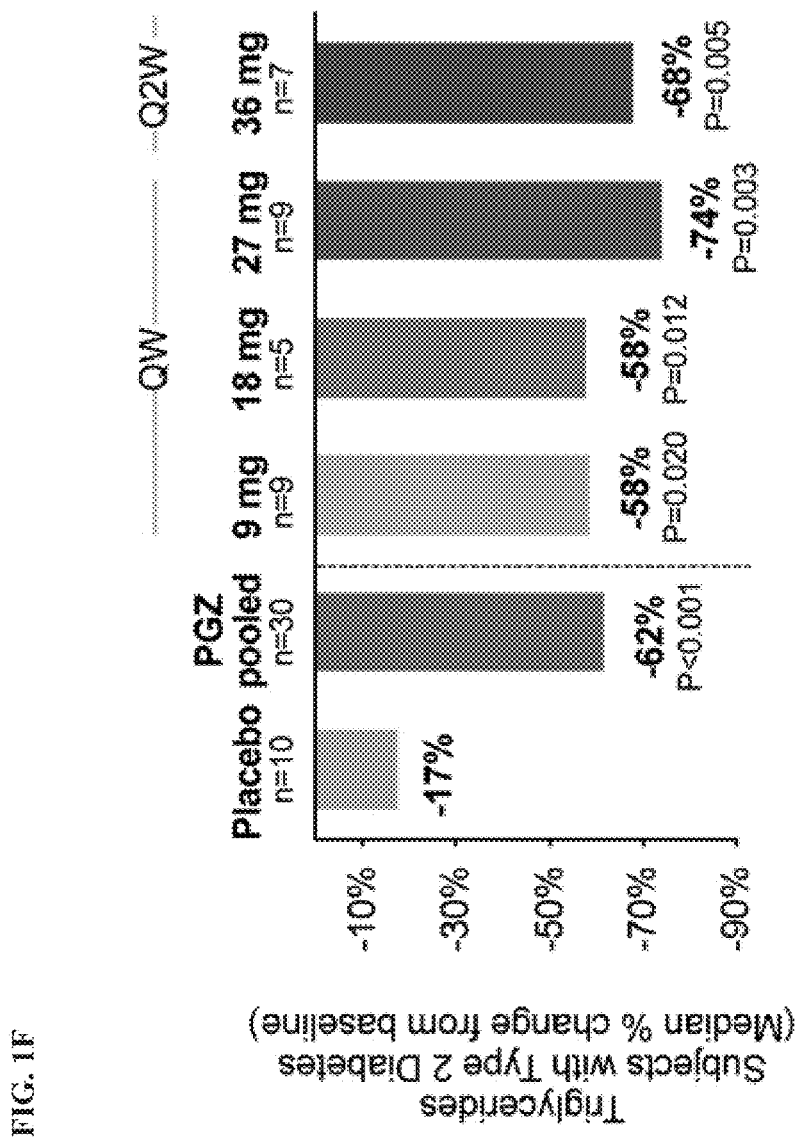

Pegozafermin significantly reduced TG after 8 weeks of therapy across all dose groups, with placebo-corrected reductions ranging from −24.6% to −51.5%. Pooled pegozafermin data showed a median percent change in TG levels of −45.4% (−57.3% vs. −11.9% placebo; 95% CI−57.1%, −30.3%; p<0.001) (FIG. 1A). The magnitude of TG reduction seen in this study was clinically significant, as 79.7% of patients treated with pegozafermin achieved a target TG level of <500 mg/dL, compared with 29.4% of patients on placebo (95% CI: 29.4%, 74.7%; p<0.001) (FIG. 1B). Furthermore, 60.9% of all patients treated with pegozafermin had reductions of ≥50% from baseline (95% CI: 36.7%, 69.5%; p<0.001), while at the highest QW dose (27 mg), 75.0% of patients saw a TG reduction of ≥50% from baseline (95% CI: 45.1%, 93.1%; p<0.001) and 31.3% were able to normalize their TG to <150 mg/dL (95% CI: 8.5%, 54.0%; p=0.012) (FIG. 1B). TG reduction was comparable across all prespecified groups (FIG. 20) and remained consistent irrespective of background lipid lowering therapy or T2DM status (FIGS. 1C-1F).

Effects on Overall Lipid Profile

Figure 2A:
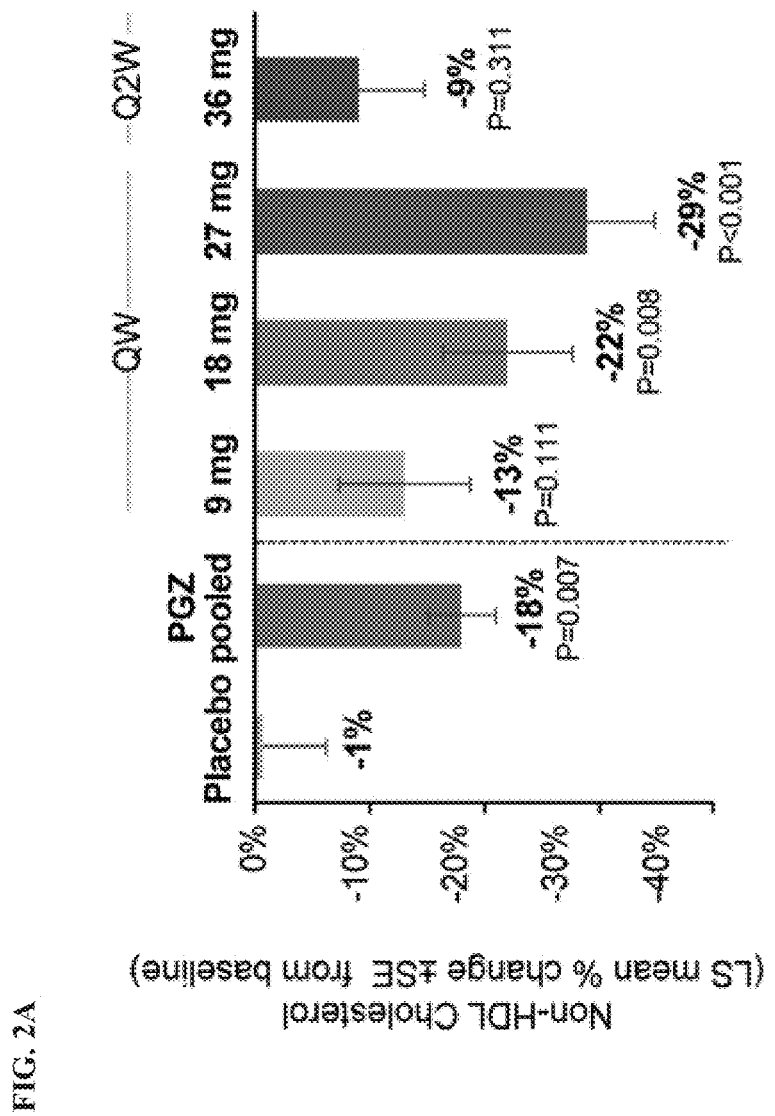
FIGS. 2A-2E are graphs showing the effect of pegozafermin on serum lipids. LS mean (+/−SE) percent change in non-HDL-C (FIG. 2A), apolipoprotein B (FIG. 2B), apolipoprotein C3 (FIG. 2C), LDL cholesterol (FIG. 2D), and HDL cholesterol (FIG. 2E) from baseline to week 8. Data based on full analysis set population and analyzed via MMRM. QW, once-weekly; Q2W, once-every two weeks.
Figure 2B:
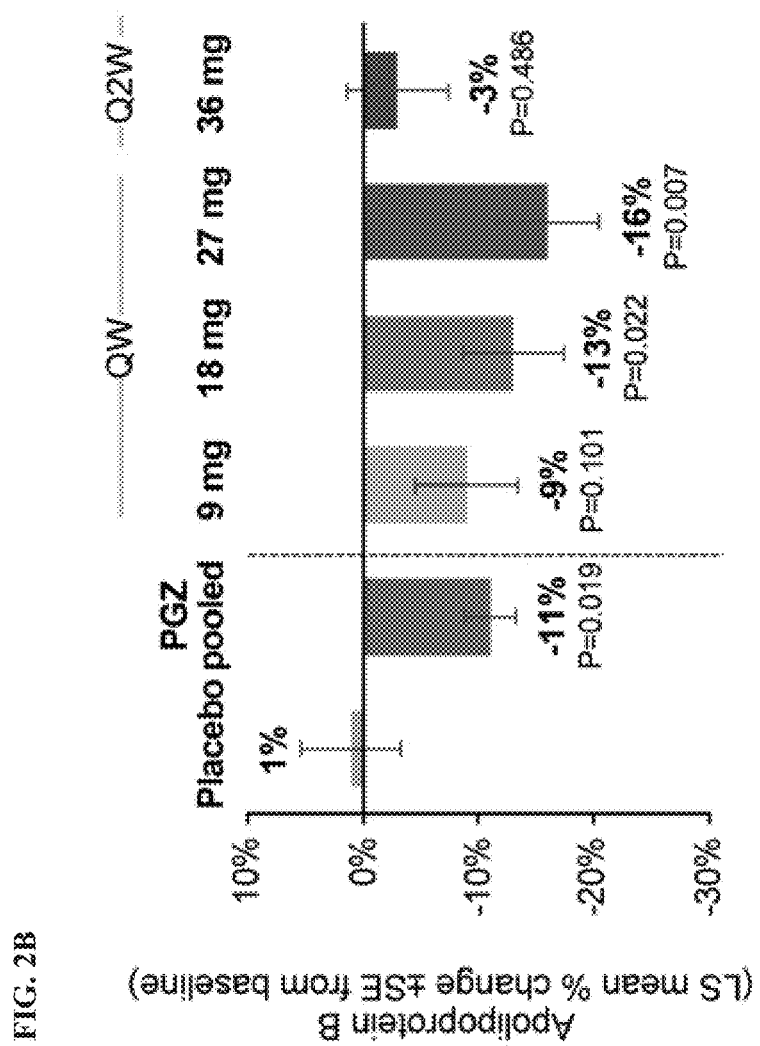
Figure 2C:
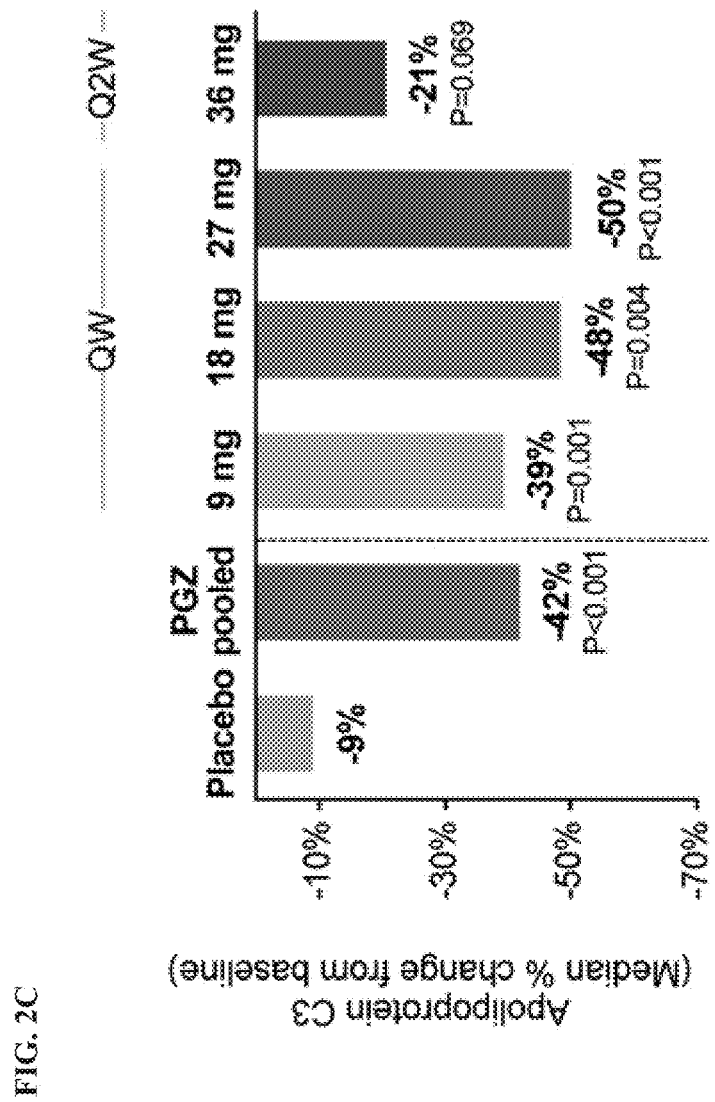
Figure 2D:
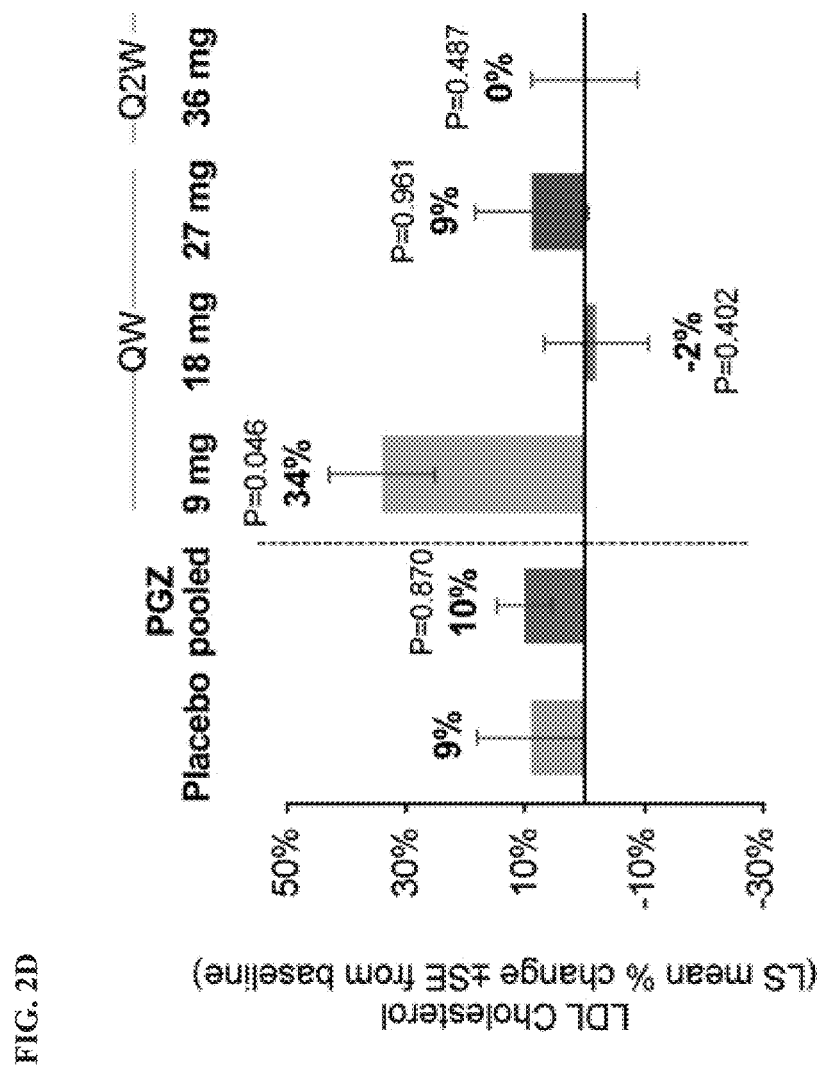
Figure 2E:
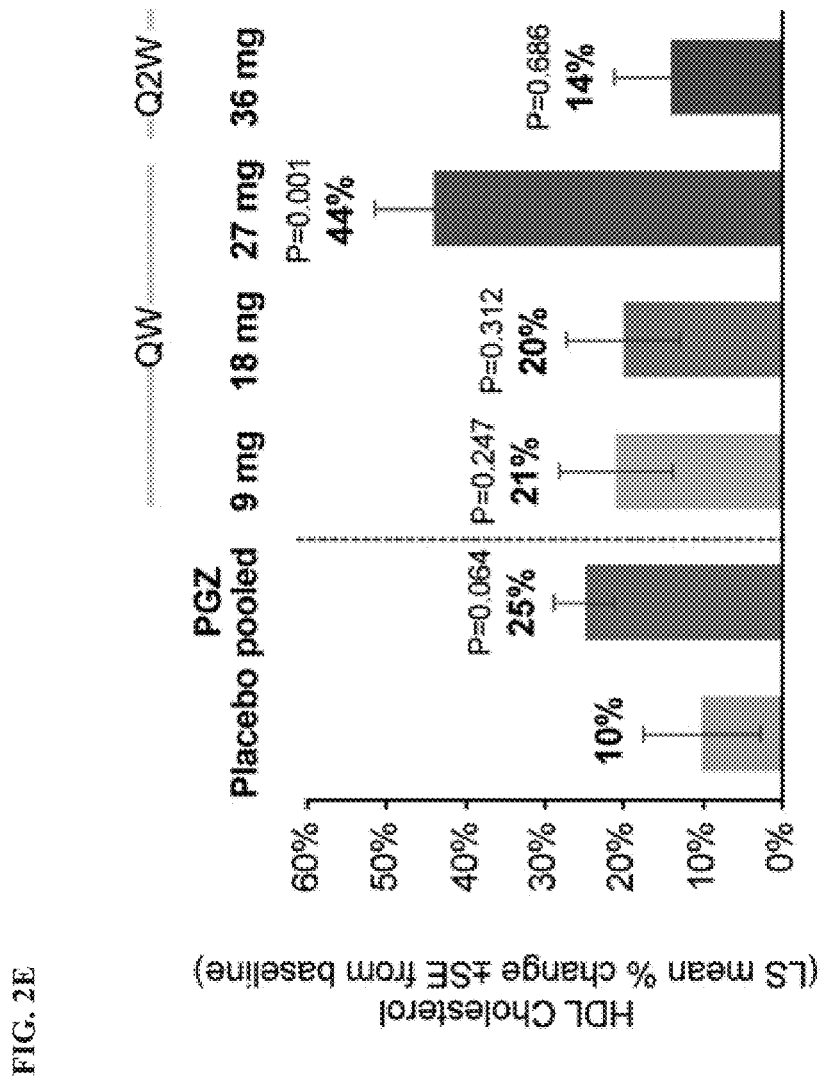

Treatment with pegozafermin resulted in clinically meaningful improvements in non-HDL-C and apoB, with an LS mean percent reduction for pooled pegozafermin of −18.3% versus −0.6% for placebo (95% CI: −30.7%, −5.1%; p=0.007) and −10.5% versus 1.1% for placebo (95% CI: −21.5%, −2.0%; p=0.019), respectively (FIG. 2A-2B). Treatment with pegozafermin also led to a significant reduction in apoC3 (median percent change −41.9% vs. −8.9% placebo; 95% CI: −44.7%, −18.0%; p<0.001) (FIG. 2C). Although minimal changes in LDL-C were detected in pooled pegozafermin (FIG. 2D), mean percent change in HDL-C levels from baseline in pegozafermin subjects receiving the 27 mg weekly dose significantly increased (44.5% vs. 9.7% for placebo; 95% CI: 14.5%, 55.1%; p=0.001) (FIG. 2E). Additional lipid data available in Table 4.

TABLE 4

| | Placebo (n = 17) | PGZ Pooled (n = 65) | PGZ 9 mg QW (n = 16) | PGZ 18 mg QW (n = 17) | PGZ 27 mg QW (n = 16) | PGZ 36 mg Q2W (n = 16) |
|---|---|---|---|---|---|---|
| Apoliporotein A1 | | | | | | |
| Mean baseline (mg/dL) | 140.15 | 137.24 | 143.34 | 137.70 | 142.03 | 125.85 |
| Mean week 8 (mg/dL) | 145.94 | 142.65 | 145.50 | 138.44 | 155.60 | 131.88 |
| % mean change from baseline | 4.28 | 4.48 | 1.86 | 0.77 | 10.02 | 5.60 |
| % median change from baseline | 4.85 | 2.95 | −0.02 | 0.71 | 13.89 | 3.59 |
| Q1, Q3 (% change) | 1.65, 9.32 | −4.73, 11.59 | −7.12, 8.16 | −6.06, 7.66 | −5.78, 24.11 | −2.00, 9.17 |
| P-value | | 0.995 | 0.608 | 0.309 | 0.101 | 0.872 |
| Apoliporotein B48 | | | | | | |
| Mean baseline (mg/dL) | 3.27 | 6.07 | 6.93 | 6.12 | 5.99 | 5.23 |
| Mean week 8 (mg/dL) | 3.18 | 2.79 | 2.73 | 2.54 | 1.98 | 3.88 |
| % mean change from baseline | 24.68 | −34.29 | −49.21 | −28.48 | −58.68 | −2.30 |
| % median change from baseline | −6.57 | −58.20 | −57.85 | −65.43 | −72.52 | −10.62 |
| Q1, Q3 (% change) | −41.28, 19.39 | −78.89, −10.34 | −77.25, −33.58 | −81.75, −28.08 | −85.69, −51.88 | −66.39, 56.51 |
| P-value | | 0.026 | 0.029 | 0.130 | 0.012 | 0.444 |
| VLDL cholesterol | | | | | | |
| Mean baseline (mg/dL) | 132.61 | 118.12 | 123.16 | 114.98 | 104.45 | 130.09 |
| Mean week 8 (mg/dL) | 118.25 | 74.13 | 76.00 | 62.56 | 51.07 | 107.53 |

TABLE 4-continued

| | Placebo (n = 17) | PGZ Pooled (n = 65) | PGZ 9 mg QW (n = 16) | PGZ 18 mg QW (n = 17) | PGZ 27 mg QW (n = 16) | PGZ 36 mg Q2W (n = 16) |
|---|---|---|---|---|---|---|
| % mean change from baseline | −9.00 | −26.57 | −15.11 | −32.67 | −50.45 | −8.39 |
| % median change from baseline | −0.41 | −47.96 | −47.86 | −57.40 | −57.98 | −16.67 |
| Q1, Q3 (% change) | −30.38, 10.98 | −63.14, −16.67 | −60.58, −32.97 | −64.56, −29.69 | −79.89, −38.58 | −45.37, 19.79 |
| P-value | | 0.006 | 0.002 | 0.009 | 0.002 | 0.740 |
| VLDL triglycerides | | | | | | |
| Mean baseline (mg/dL) | 588.74 | 637.88 | 588.02 | 574.18 | 601.88 | 791.42 |
| Mean week 8 (mg/dL) | 516.38 | 405.28 | 394.94 | 293.94 | 246.80 | 714.14 |
| % mean change from baseline | −7.47 | −18.97 | 7.96 | −32.30 | −57.68 | 6.95 |
| % median change from baseline | −0.85 | −58.50 | −60.35 | −63.51 | −67.83 | −26.03 |
| Q1, Q3 (% change) | −27.72, 14.25 | −72.53, −32.80 | −68.25, −46.01 | −76.34, −41.50 | −85.86, −46.05 | −38.26, 13.85 |
| P-value | | 0.002 | <0.001 | 0.003 | <0.001 | 0.471 |
| Total cholesterol | | | | | | |
| Mean baseline (mg/dL) | 247.04 | 237.47 | 246.89 | 230.46 | 232.84 | 240.13 |
| Mean week 8 (mg/dL) | 235.53 | 199.84 | 211.25 | 184.13 | 186.87 | 216.31 |
| % mean change from baseline | −2.10 | −13.43 | −10.43 | −17.21 | −19.66 | −6.83 |
| % median change from baseline | −0.65 | −14.94 | −10.44 | −19.43 | −19.44 | −6.34 |
| Q1, Q3 (% change) | −9.03, 5.71 | −28.30, −1.67 | −22.22, −2.71 | −41.29, −1.91 | −33.49, −7.62 | −20.00, 7.21 |
| P-value | | 0.010 | 0.059 | 0.032 | 0.003 | 0.397 |
| Free fatty acids | | | | | | |
| Mean baseline (mmol/L) | 0.58 | 0.53 | 0.50 | 0.55 | 0.53 | 0.53 |
| Mean week 8 (mmol/L) | 0.48 | 0.53 | 0.57 | 0.54 | 0.48 | 0.51 |
| % mean change from baseline | −12.54 | 6.82 | 27.79 | 7.64 | −5.08 | −5.33 |
| % median change from baseline | −17.45 | −3.97 | 12.93 | −5.43 | −8.83 | −2.87 |
| Q1, Q3 (% change) | −27.70, 12.92 | −19.65, 22.97 | −25.26, 51.94 | −16.30, 32.16 | −37.58, 17.59 | −19.65, 4.83 |
| P-value | | 0.209 | 0.101 | 0.236 | 0.597 | 0.419 |
| Lipoprotein (a) | | | | | | |
| Mean baseline (nmol/L) | 43.69 | 41.86 | 48.18 | 21.12 | 42.15 | 58.30 |
| Mean week 8 (nmol/L) | 47.94 | 61.28 | 74.31 | 31.75 | 57.63 | 81.19 |
| % mean change from baseline | −0.97 | 53.09 | 68.58 | 33.06 | 59.79 | 51.25 |
| % median change from baseline | −1.09 | 39.49 | 50.21 | 23.44 | 27.87 | 43.17 |
| Q1, Q3 (% change) | −34.55, 25.26 | 10.00, 83.08 | 37.31, 111.55 | 0.00, 59.29 | 3.80, 115.63 | 11.76, 69.52 |
| P-value | | 0.002 | 0.002 | 0.090 | 0.021 | 0.003 |
| LDL particle size | | | | | | |
| Mean baseline (nm) | 19.79 | 19.79 | 19.87 | 19.69 | 19.86 | 19.73 |
| Mean week 8 (nm) | 19.59 | 20.06 | 20.07 | 19.79 | 20.55 | 19.81 |
| % mean change from baseline | −1.18 | 1.40 | 1.27 | 0.45 | 3.52 | 0.40 |
| % median change from baseline | −1.03 | 1.03 | 0.50 | 0.00 | 3.60 | 0.00 |
| Q1, Q3 (% change) | −2.53, 0.52 | −0.50, 3.55 | −1.02, 2.60 | −2.01, 3.32 | 2.54, 5.10 | −0.50, 1.29 |
| P-value | | 0.004 | 0.130 | 0.232 | <0.001 | 0.097 |

TABLE 4-continued

|  | Placebo (n = 17) | PGZ Pooled (n = 65) | PGZ 9 mg QW (n = 16) | PGZ 18 mg QW (n = 17) | PGZ 27 mg QW (n = 16) | PGZ 36 mg Q2W (n = 16) |
|---|---|---|---|---|---|---|
| LDL particle number |  |  |  |  |  |  |
| Mean baseline (nmol/L) | 1533.16 | 1653.29 | 1656.31 | 1675.73 | 1789.67 | 1501.38 |
| Mean week 8 (nmol/L) | 1515.94 | 1605.57 | 1650.73 | 1522.87 | 1764.13 | 1492.13 |
| % mean change from baseline | 5.49 | 4.54 | 13.04 | −8.40 | 1.38 | 9.83 |
| % median change from baseline | 3.03 | −2.06 | 4.93 | −7.78 | −4.19 | −5.95 |
| Q1, Q3 (% change) | −16.37, 19.72 | −20.44, 18.32 | −3.87, 32.03 | −24.46, 18.68 | −26.42, 10.64 | −27.97, 18.30 |
| P-value |  | 0.435 | 0.455 | 0.381 | 0.419 | 0.678 |

Hepatic and Metabolic Effects

Figure 3A:
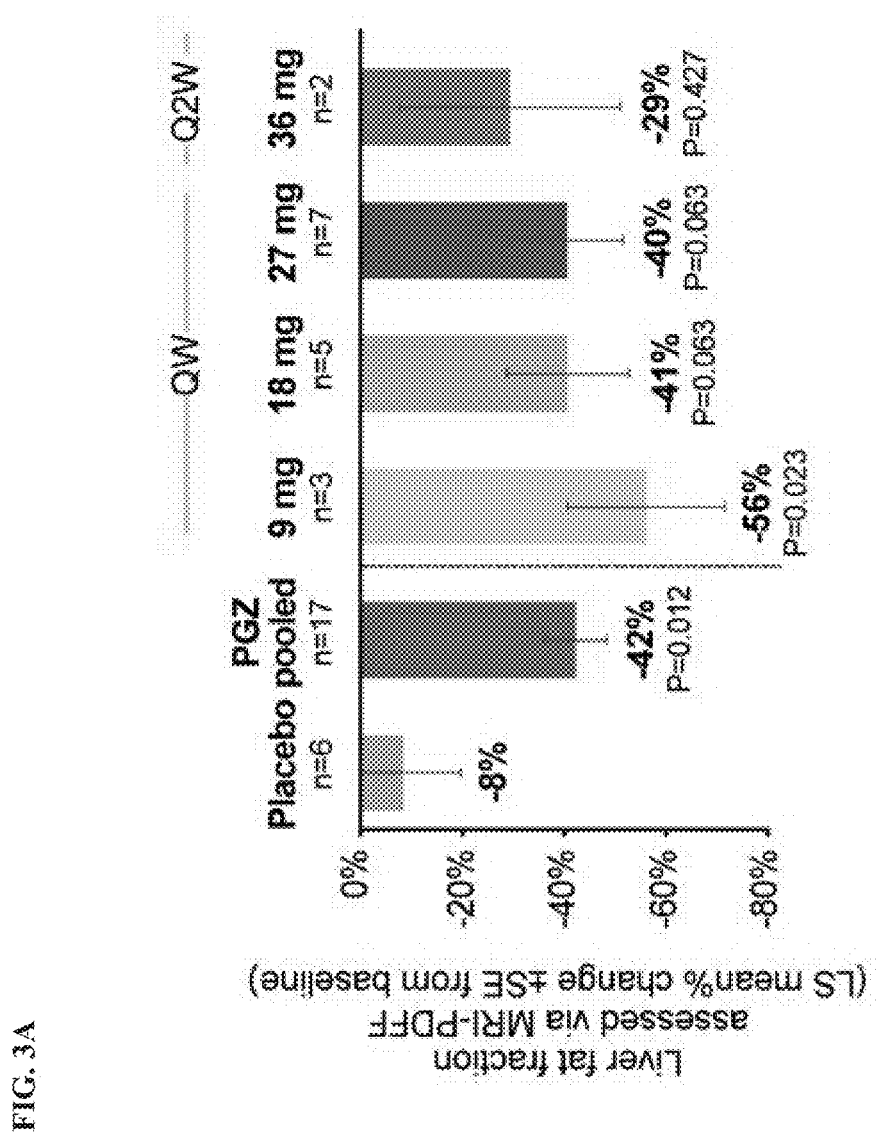
FIGS. 3A-3E show the effect of pegozafermin on markers of liver health and metabolic dysregulation.
Figure 3B:
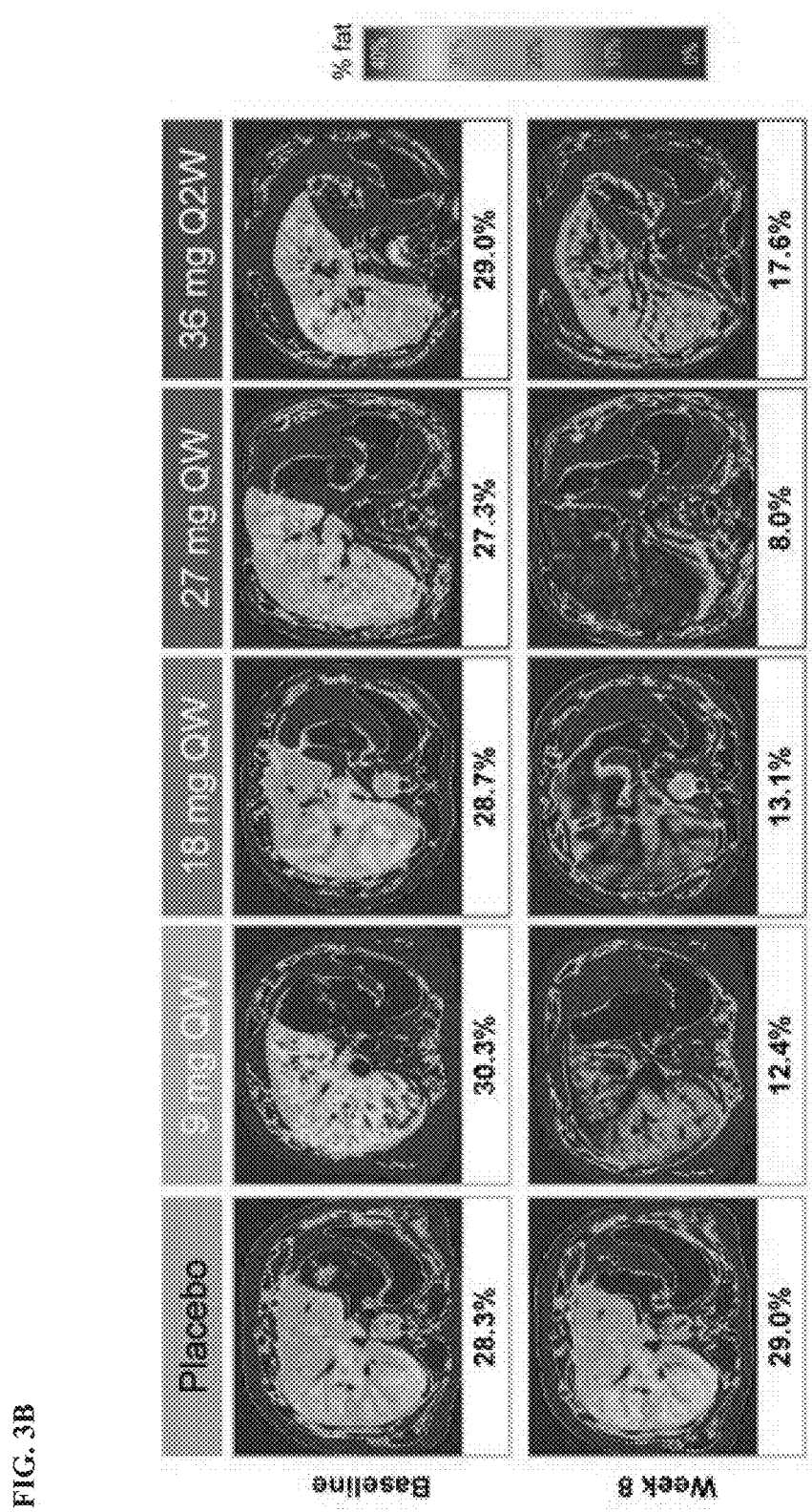
Figure 3C:
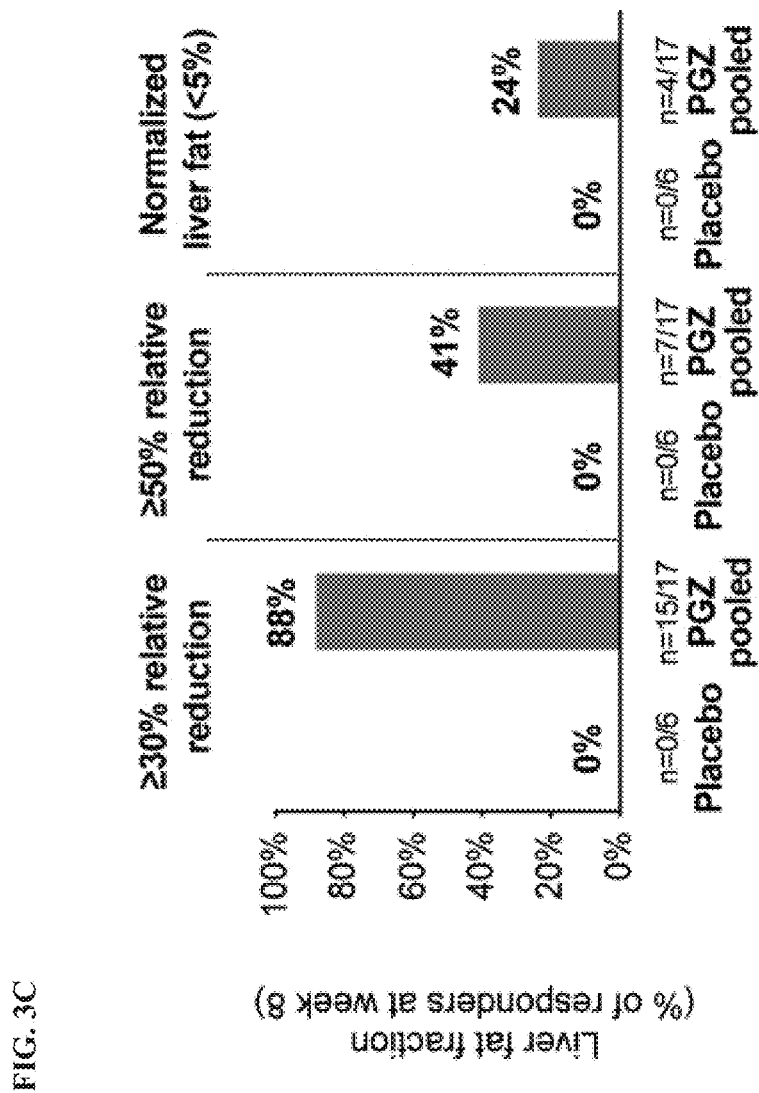
Figure 6A:
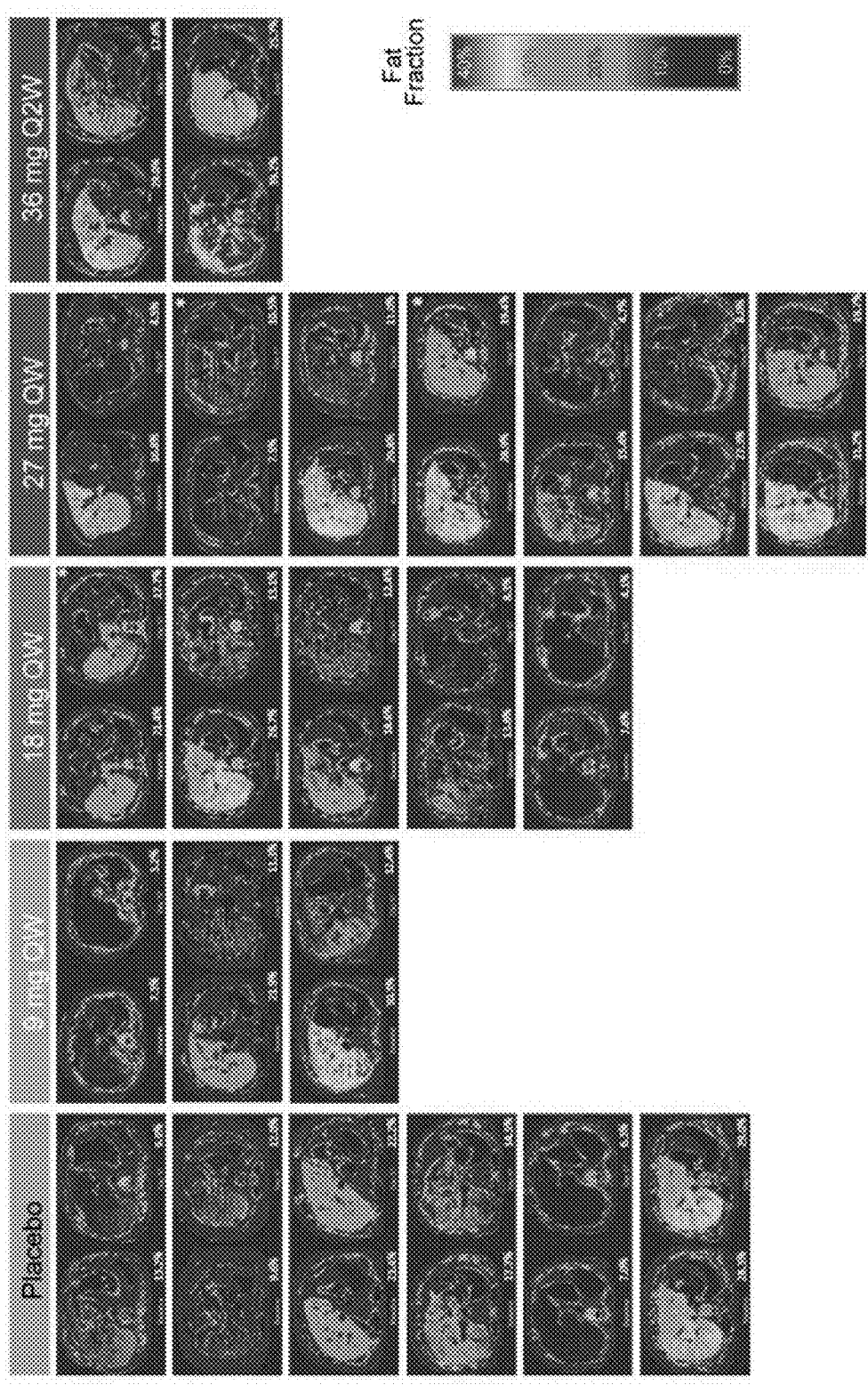
FIG. 6A show MRI-PDFF images are shown for all individual.
Figure 6B:
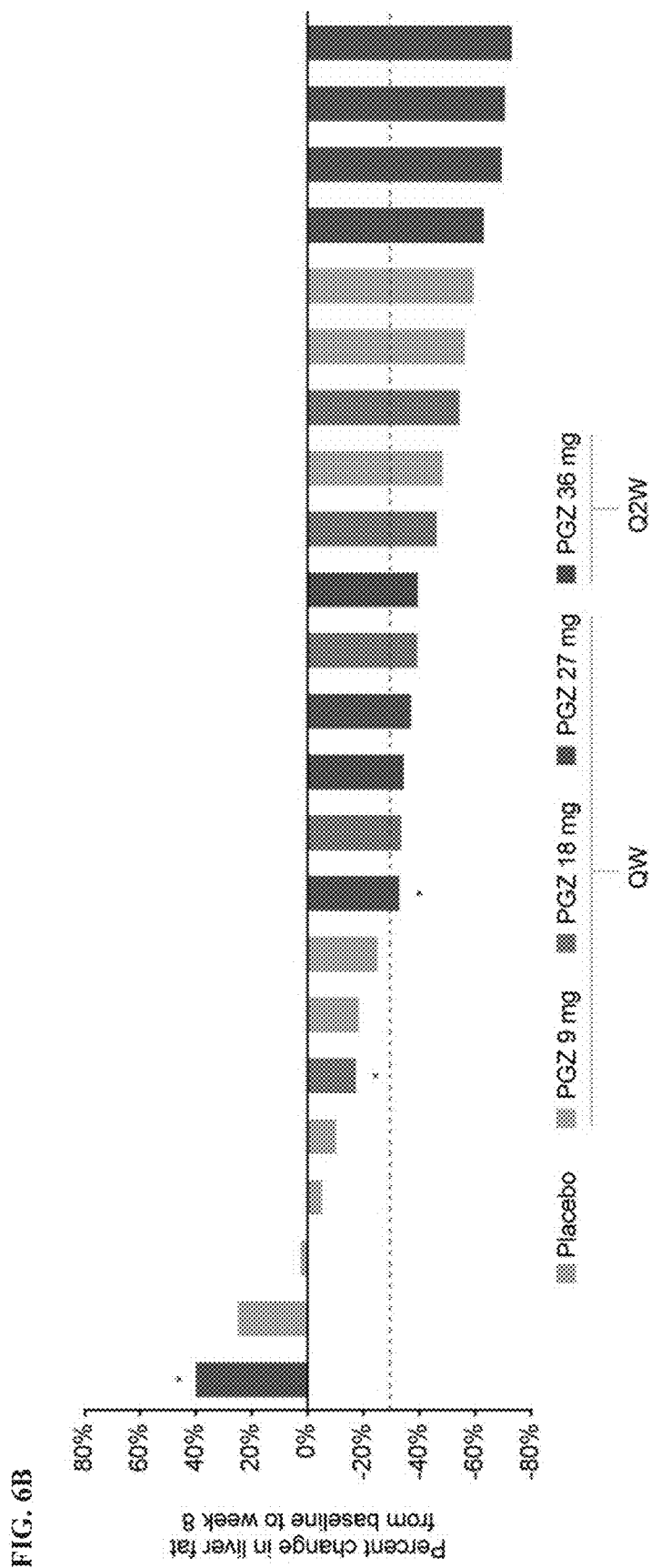
FIG. 6B is a graph showing all individual treatment responses.

Patients treated with pegozafermin for 8 weeks had significant reductions in liver steatosis compared with placebo (LS mean percent change −42.2% vs. −8.3%; 95% CI: −60.9%, −8.7%; p=0.012) (FIG. 3A). Representative MRI-PDFF images are shown in FIG. 3B, with all individual treatment responses and images presented in FIGS. 6A-6B. Many patients treated with pegozafermin attained important clinical thresholds, including ≥30% reduction, ≥50% reduction or normalization of liver fat (defined as <5%), with response rates of 88%, 41% and 24%, respectively, compared with 0% in placebo across all measurements (FIG. 3C). Patients receiving the 27 mg weekly dose also saw improvement in body weight and the following markers: ALT, AST and hsCRP (Table 5).

Figure 3D:
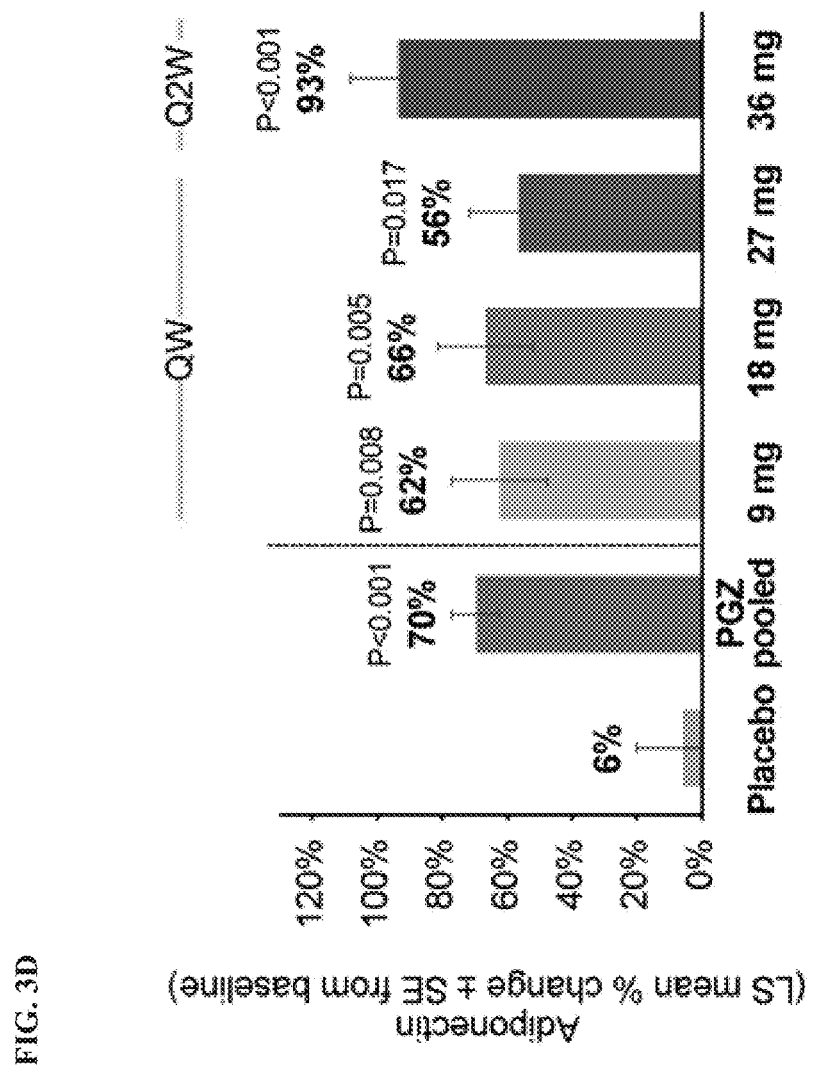
Figure 3E:
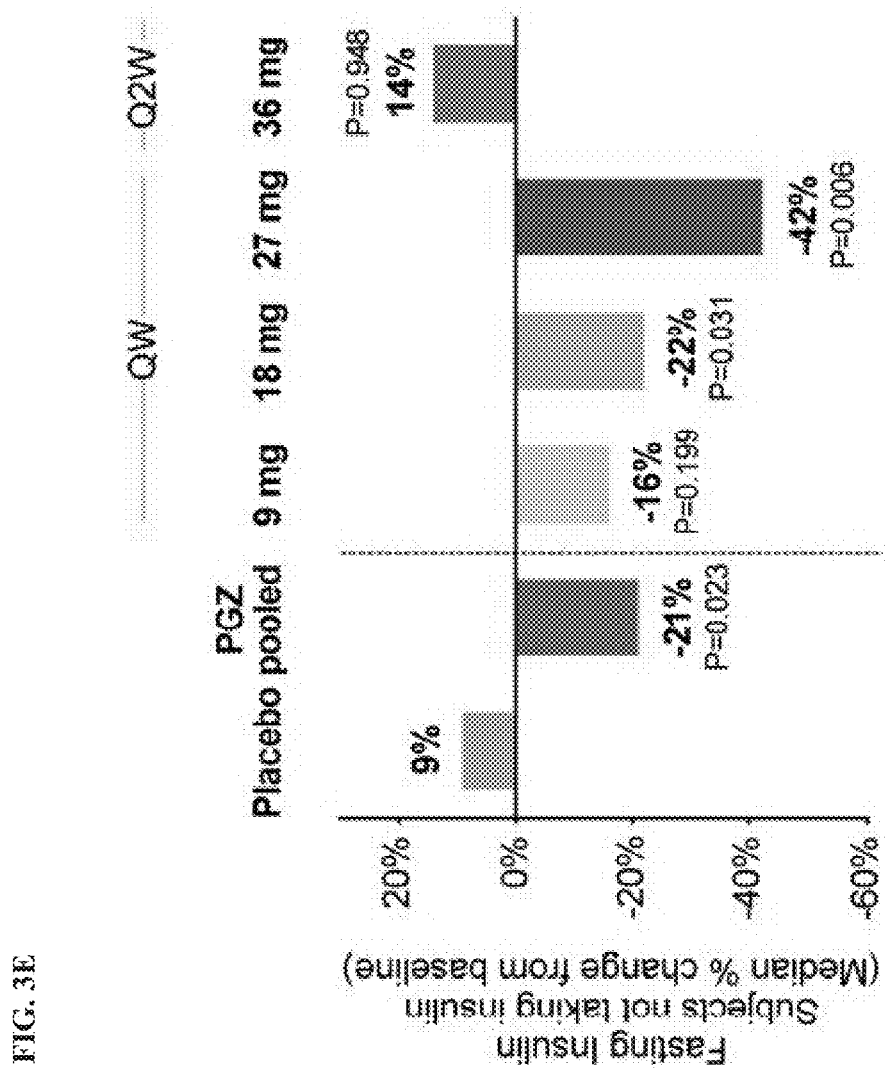

There was a robust increase in adiponectin across all doses of pegozafermin, with placebo-corrected values ranging from 50.6% to 87.6%, and a mean percent change in pooled pegozafermin doses of 62.8% (69.5% vs. 5.7% placebo; 95% CI: 30.3%, 95.3%; p<0.001) (FIG. 3D). Additionally, in patients not taking concomitant insulin, pegozafermin significantly lowered median insulin levels in both the 18 mg and 27 mg weekly dose groups (−21.5% [p=0.031] and −41.8% [p=0.006], respectively) compared with a 9.3% increase for placebo (FIG. 3E). Additional metabolic benefits observed after 8 weeks of treatment in patients randomized to the 27 mg weekly dose included improvements in fasting plasma glucose and HbA1c (Table 5).

TABLE 5

|  | Placebo (n = 17) | PGZ Pooled (n = 65) | PGZ 9 mg QW (n = 16) | PGZ 18 mg QW (n = 17) | PGZ 27 mg QW (n = 16) | PGZ 36 mg Q2W (n = 16) |
|---|---|---|---|---|---|---|
| Hemoglobin A1c* |  |  |  |  |  |  |
| Mean baseline (%) | 6.12 | 6.58 | 6.63 | 6.59 | 6.72 | 6.37 |
| Mean week 8 (%) | 6.01 | 6.52 | 6.64 | 6.58 | 6.53 | 6.32 |
| Absolute mean change from baseline (%) | −0.11 | −0.05 | 0.00 | 0.11 | −0.26 | −0.05 |
| Absolute median change from baseline (%)e | −0.05 | 0.00 | 0.10 | 0.10 | −0.25 | −0.08 |
| P-value |  | 0.556 | 0.105 | 0.075 | 0.692 | 0.732 |
| Fasting plasma glucose* |  |  |  |  |  |  |
| Mean baseline (mg/dL) | 121.83 | 144.97 | 158.52 | 139.29 | 143.40 | 139.04 |
| Mean week 8 (mg/dL) | 120.12 | 134.48 | 134.63 | 144.25 | 129.47 | 129.25 |
| % mean change from baseline | 0.98 | −4.21 | −8.26 | 3.85 | −9.44 | −3.33 |
| % median change from baseline | 0.30 | −3.92 | −5.59 | 0.15 | −12.78 | −1.13 |
| P-value |  | 0.809 | 0.700 | 0.446 | 0.344 | 0.908 |
| Body weight* |  |  |  |  |  |  |
| Mean baseline (kg) | 97.50 | 98.45 | 99.62 | 96.76 | 98.36 | 99.17 |
| Mean week 8 (kg) | 97.29 | 99.14 | 99.92 | 98.24 | 98.83 | 99.56 |
| % mean change from baseline | −0.16 | −0.14 | 0.07 | 0.20 | −1.33 | 0.41 |
| % median change from baseline | −0.21 | −0.15 | 0.46 | −0.10 | 0.11 | −0.16 |
| P-value |  | 0.973 | 0.839 | 0.624 | 0.191 | 0.565 |
| Aspartate transaminase* |  |  |  |  |  |  |
| Mean baseline (mg/dL) | 23.71 | 24.80 | 26.69 | 27.65 | 24.06 | 20.63 |
| Mean week 8 (mg/dL) | 23.65 | 19.65 | 20.06 | 19.25 | 20.53 | 18.81 |
| % mean change from baseline | 1.45 | −11.10 | −12.62 | −11.16 | −15.94 | −4.99 |
| % median change from baseline | 0.00 | −11.76 | −14.85 | −8.57 | −23.33 | −5.41 |
| P-value |  | 0.073 | 0.052 | 0.135 | 0.019 | 0.428 |

TABLE 5-continued

|  | Placebo (n = 17) | PGZ Pooled (n = 65) | PGZ 9 mg QW (n = 16) | PGZ 18 mg QW (n = 17) | PGZ 27 mg QW (n = 16) | PGZ 36 mg Q2W (n = 16) |
|---|---|---|---|---|---|---|
| Alanine transaminase* | | | | | | |
| Mean baseline (mg/dL) | 28.35 | 33.66 | 36.25 | 36.94 | 32.06 | 29.19 |
| Mean week 8 (mg/dL) | 28.71 | 28.98 | 29.81 | 32.81 | 24.60 | 28.44 |
| % mean change from baseline | 2.56 | −4.78 | −4.66 | −1.86 | −17.62 | 4.22 |
| % median change from baseline | −4.17 | −9.52 | −15.08 | −6.41 | −22.22 | 4.00 |
| P-value | | 0.343 | 0.242 | 0.482 | 0.027 | 0.857 |
| Gamma Glutamyl Transferase | | | | | | |
| Mean baseline (U/L) | 64.8 | 54.8 | 53.6 | 71.2 | 39.5 | 51.3 |
| Mean week 8 (U/L) | 73.4 | 48.7 | 41.5 | 68.0 | 28.2 | 49.1 |
| % mean change from baseline | 12.2 | −9.4 | −11.2 | −5.8 | −24.9 | 1.9 |
| % median change from baseline | 8.8 | −18.0 | −16.4 | −16.8 | −30.4 | −11.5 |
| Min, Max (% change) | −72, 100 | −66, 142 | −66, 68 | −55, 99 | −57, 49 | −32, 142 |
| Alkaline phosphatase& | | | | | | |
| Mean baseline (U/L) | 65.7 | 65.4 | 65.5 | 69.1 | 60 | 66.7 |
| Mean week 8 (U/L) | 67.8 | 63.1 | 67.8 | 63.7 | 54.1 | 67.3 |
| % mean change from baseline | 5.4 | −0.3 | 3.9 | −3.2 | −1.2 | 1.2 |
| % median change from baseline | 3.5 | −2.3 | 2.4 | −2.6 | −4.1 | −3.5 |
| Min, Max (% change) | −17, 57 | −23, 30 | −10, 30 | −23, 14 | −20, 30 | −15, 28 |

Safety

Treatment emergent adverse events (TEAEs) were reported in 41/67 (61.2%) of patients treated with pegozafermin versus 9/18 (50%) on placebo (Table 2). The most common TEAEs were related to gastrointestinal disturbances and injection site reactions, all of which were mild to moderate, with the majority transient in duration. In the pooled pegozafermin group, nausea, diarrhea and injection site reactions occurred at rates of 13.4%, 10.4% and 9%, respectively, compared with 0%, 5.6% and 0% for placebo. The percent of TEAEs was higher for nausea (27.8%) and diarrhea (22.2%) in the 27 mg weekly dose. No Grade 3 or higher TEAEs were reported. One serious TEAE of hypertension was reported in the 27 mg QW arm, deemed unrelated to treatment, which led to study discontinuation. There were 4 additional treatment emergent discontinuations in the 27 mg arm: 2 were considered unrelated and 2 were considered related (Table 2). No deaths or adverse events of transaminase elevation were reported.

TABLE 2

|  | Placebo (n = 18) | PGZ Pooled (n = 67) | PGZ 9 mg QW (n = 12) | PGZ 18 mg QW (n = 21) | PGZ 27 mg QW (n = 18) | PGZ 36 mg Q2W (n = 16) |
|---|---|---|---|---|---|---|
| Treatment-emergent adverse events (TEAEs) | 9 (50.0) | 41 (61.2) | 7 (58.3) | 13 (61.9) | 14 (77.8) | 7 (43.8) |
| Grade 1 (Mild) | 5 (27.8) | 22 (32.8) | 6 (50.0) | 7 (33.3) | 6 (33.3) | 3 (18.8) |
| Grade 2 (Moderate) | 4 (22.2) | 19 (28.4) | 1 (8.3) | 6 (28.6) | 8 (44.4) | 4 (25.0) |
| Grade >3 (Severe) | 0 | 0 | 0 | 0 | 0 | 0 |
| Serious TEAEs | 0 | 1 (1.5) | 0 | 0 | 1 (5.6) | 0 |
| Hypertension | 0 | 1 (1.5) | 0 | 0 | 1 (5.6) | 0 |
| TEAEs related to treatment | 2 (11.1) | 23 (34.3) | 5 (41.7) | 6 (28.6) | 7 (38.9) | 51 (31.3) |
| Serious TEAEs related to treatment | 0 | 0 | 0 | 0 | 0 | 0 |
| TEAEs leading to treatment discontinuation | 0 | 4 (6.0) | 0 | 0 | 4 (22.2) | 0 |
| Hypertention | 0 | 1 (1.5) | 0 | 0 | 1 (5.6) | 0 |
| Abdominal pain | 0 | 2 (3.0) | 0 | 0 | 2 (11.1) | 0 |
| Nausea | 0 | 2 (3.0) | 0 | 0 | 2 (11.1) | 0 |
| Vomiting | 0 | 1 (1.5) | 0 | 0 | 1 (5.6) | 0 |
| TEAEs reported by ≥5% in pooled PGZ groups | | | | | | |
| Nausea | 0 | 9 (13.4) | 1 (8.3) | 1 (4.8) | 5 (27.8) | 2 (12.5) |
| Diarrhea | 1 (5.6) | 7 (10.4) | 2 (16.7) | 1 (4.8) | 4 (22.2) | 0 |
| Injection site reaction | 0 | 6 (9.0) | 1 (8.3) | 2 (9.5) | 1 (5.6) | 2 (12.5) |
| COVID-19 | 3 (16.7) | 4 (6.0) | 0 | 3 (14.3) | 0 | 1 (6.3) |
| Injection site erythema | 0 | 4 (6.0) | 0 | 1 (4.8) | 2 (11.1) | 1 (6.3) |
| Injection site pruritus | 0 | 4 (6.0) | 1 (8.3) | 2 (9.5) | 1 (5.6) | 0 |
| Abdominal pain | 0 | 3 (4.5) | 0 | 0 | 2 (11.1) | 1 (6.3) |

Discussion

This placebo-controlled, randomized study demonstrated that treatment with the FGF21 analog pegozafermin resulted in a significant reduction in TG in patients with SHTG, with 80% of patients achieving TG≤500 mg/dL. Additionally, non-HDL cholesterol, apoB and apoC3 were significantly reduced, suggesting pegozafermin reduces production and improves clearance of TG-rich lipoproteins. Whereas levels of LDL cholesterol remained stable, there was a numerical increase in HDL cholesterol across all doses, most notably at the 27 mg dose. Despite the short 8-week duration of the trial, the 27 mg QW dose of pegozafermin improved various measures of insulin sensitivity, such as adiponectin. Previous data from a NASH population suggest, for the 27 mg QW dose, improvements continue to intensify over a longer treatment period; in particular, in NASH patients with a baseline HbA1c≥6.5%, an absolute reduction in HbA1c of 0.9 was achieved at week20.[22]

Another important finding of the present study was the prevalence of liver fat in this severe hypertriglyceridemia population: 100% of subjects with MRI-PDFF data had baseline hepatic steatosis as defined by >5% liver fat. This raises the question of whether patients with SHTG should be routinely screened for liver fat—something that will need to be tested in future randomized trials. To our knowledge, these are the first data to demonstrate a significant reduction in liver fat with a treatment targeting TG-rich lipoproteins in severe hypertriglyceridemia. Safety and tolerability remained consistent with previous data, with mild to moderate gastrointestinal disturbance being the most common TEAE.[21,22] There were no serious TEAEs related to the study drug.

Severe hypertriglyceridemia patients often have metabolic comorbidities associated with dyslipidemia and insulin resistance, such as obesity, metabolic syndrome, T2DM and non-alcoholic fatty liver disease. Data in patients with residual dyslipidemia on lipid-modifying therapy in the United States showed only 36.5% of such patients were at goal or near normal levels for TG, LDL-C and HDL-C[28] We demonstrate in this phase 2 trial that the FGF21 pathway improved lipids and markers of insulin sensitivity to potentially impact metabolic health. Furthermore, pegozafermin demonstrated that fat accumulation in the liver can be reversed in the relatively short period of eight weeks.

Limitations of this study included its power to assess clinical events such as pancreatitis, liver failure or cardiovascular endpoints. Further safety and tolerability data from a longer period of drug exposure at the target dose are necessary.

In conclusion, the FGF21 analog pegozafermin significantly reduced TG, non-HDL cholesterol, apoB, apoC3 and liver fat in patients with SHTG, with the potential to positively impact other aspects of metabolic dysregulation. If these findings are confirmed in an appropriately powered phase 3 trial, pegozafermin may be useful to treat SHTG and simultaneously address several other cardiometabolic risk factors.

REFERENCES

1. Wang G J, Gao C F, Wei D, Wang C, Ding S Q. Acute pancreatitis: etiology and common pathogenesis. World J Gastroenterol 2009; 15(12):1427-30. DOI: 10.3748/wjg.15.1427.
2. Anderson F, Thomson S R, Clarke D L, Buccimazza I. Dyslipidaemic pancreatitis clinical assessment and analysis of disease severity and outcomes. Pancreatology 2009; 9(3):252-7. DOI: 10.1159/000212091.
3. Yuan G, Al-Shall K Z, Hegele R A. Hypertriglyceridemia: its etiology, effects and treatment. CMAJ 2007; 176(8): 1113-20. DOI: 10.1503/cmaj.060963.
4. Ganda O P, Bhatt D L, Mason R P, Miller M, Boden W E. Unmet need for adjunctive dyslipidemia therapy in hypertriglyceridemia management. J Am Coll Cardiol 2018; 72(3):330-343. DOI: 10.1016/j.jacc.2018.04.061.
5. Toth P P, Granowitz C, Hull M, Liassou D, Anderson A, Philip S. High triglycerides are associated with increased cardiovascular events, medical costs, and resource use: a real-world administrative claims analysis of statin-treated patients with high residual cardiovascular risk. J Am Heart Assoc 2018; 7(15):e008740. DOI: 10.1161/JAHA.118.008740.
6. Klempfner R, Erez A, Sagit B Z, et al. Elevated triglyceride level is independently associated with increased all-cause mortality in patients with established coronary heart disease: twenty-two-year follow-up of the Bezafibrate Infarction Prevention Study and Registry. Circ Cardiovasc Qual Outcomes 2016; 9(2):100-8. DOI: 10.1161/CIRCOUTCOMES.115.002104.
7. Nichols G A, Philip S, Reynolds K, Granowitz C B, Fazio S. Increased cardiovascular risk in hypertriglyceridemic patients with statin-controlled LDL cholesterol. J Chin Endocrinol Metab 2018; 103(8):3019-3027. DOI: 10.1210/jc.2018-00470.
8. Libby P. Triglycerides on the rise: should we swap seats on the seesaw? Eur Heart J 2015; 36(13):774-6. DOI: 10.1093/eurheartj/ehu500.
9. Bhatt D L, Steg P G, Miller M, et al. Cardiovascular Risk Reduction with Icosapent Ethyl for Hypertriglyceridemia. N Engl J Med 2019; 380(1):11-22. DOI:
10. Nichols G A, Philip S, Reynolds K, Granowitz C B, Fazio S. Increased residual cardiovascular risk in patients with diabetes and high versus normal triglycerides despite statin-controlled LDL cholesterol. Diabetes Obes Metab 2019; 21(2):366-371. DOI:
11. Virani S S, Morris P B, Agarwala A, et al. 2021 ACC expert consensus decision pathway on the management of ASCVD risk reduction in patients with persistent hypertriglyceridemia: a report of the American College of Cardiology Solution Set Oversight Committee. J Am Coll Cardiol 2021; 78(9):960-993. DOI: 10.1016/j.jacc.2021.06.011.
12. American College of Cardiology. Hypertriglyceridemia management according to the 2018 AHA/ACC guideline. August 2022 (https://www.acc.org/latest-in-cardiology/articles/2019/01/11/07/39/hypertriglyceridemia-management-according-to-the-2018-aha-acc-guideline).
13. Rosenson R S, Eckel R H. Hypertriglyceridemia in adults: management. August 2022 (https://www.uptodate.com/contents/hypertriglyceridemia-in-adults-management).
14. Xing J, Guan X, Zhang Q, Chen S, Wu S, Sun X. Triglycerides mediate body mass index and nonalcoholic fatty liver disease: a population-based study. Obes Facts 2021; 14(2):190-196. DOI: 10.1159/000514848.
15. Rashid N, Sharma P P, Scott R D, Lin K J, Toth P P. Severe hypertriglyceridemia and factors associated with acute pancreatitis in an integrated health care system. J Clin Lipidol 2016; 10(4):880-890. DOI: 10.1016/j.jacl.2016.02.019.
16. Pejic R N, Lee D T. Hypertriglyceridemia. J Am Board Fam Med 2006; 19(3):310-6. DOI: 10.3122/jabfm.19.3.310.

17. Lin X, Liu Y B, Hu H. Metabolic role of fibroblast growth factor 21 in liver, adipose and nervous system tissues. Biomedical reports 2017; 6(5):495-502. DOI:
18. Tillman E J, Rolph T. FGF21: an emerging therapeutic target for non-alcoholic steatohepatitis and related metabolic diseases. Front Endocrinol (Lausanne) 2020; 11:601290. DOI: 10.3389/fendo.2020.601290.
19. Kliewer S A, Mangelsdorf D J. A dozen years of discovery: insights into the physiology and pharmacology of FGF21. Cell Metab 2019; 29(2):246-253. DOI: 10.1016/j.cmet.2019.01.004.
20. Stojsavljevic-Shapeski S, Duvnjak M, Virovic-Jukic L, Hrabar D, Smircic Duvnjak L. New drugs on the block-emerging treatments for nonalcoholic steatohepatitis. J Clin Transl Hepatol 2021; 9(1):51-59. DOI: 10.14218/JCTH.2020.00057.
21. Frias J P, Lawitz E J, Ortiz-LaSanta G, et al. BIO89-100 demonstrated robust reductions in liver fat and liver fat volume (LFV) by MRI-PDFF, favorable tolerability and potential for weekly (QW) or every 2 weeks (Q2W) dosing in a phase 1b/2a placebo-controlled, double-blind, multiple ascending dose study in NASH. J Endocr Soc 2021; 5(Supplement_1):A5-A6. DOI: 10.1210/jendso/bvab048.010.
22. Alkhouri N, Loomba R, Frias J P, et al. Pegozafermin led to significant metabolic benefits, in addition to robust beneficial effects on the liver, in an open-label cohort of a phase 1b/2a study in subjects with non-alcoholic steatohepatitis (NASH). J Hepatol 2022; 77:5732. DOI: 10.1016/S0168-8278(22)01785-8.
23. Gaich G, Chien J Y, Fu H, et al. The effects of LY2405319, an FGF21 analog, in obese human subjects with type 2 diabetes. Cell Metab 2013; 18(3):333-40. DOI: 10.1016/j.cmet.2013.08.005.
24. Talukdar S, Zhou Y, Li D, et al. A long-acting FGF21 molecule, PF-05231023, decreases body weight and improves lipid profile in non-human primates and type 2 diabetic subjects. Cell Metab 2016; 23(3):427-40. DOI: 10.1016/j.cmet.2016.02.001.
25. Charles E D, Neuschwander-Tetri B A, Pablo Frias J, et al. Pegbelfermin (BMS-986036), pEGylated FGF21, in patients with obesity and type 2 diabetes: results from a randomized phase 2 study. Obesity (Silver Spring) 2019; 27(1):41-49. DOI: 10.1002/oby.22344.
26. Kaufman A, Abuqayyas L, Denney W S, Tillman E J, Rolph T. AKR-001, an Fc-FGF21 analog, showed sustained pharmacodynamic effects on insulin sensitivity and lipid metabolism in type 2 diabetes patients. Cell Rep Med 2020; 1(4):100057. DOI:
27. Harrison S A, Ruane P J, Freilich B L, et al. Efruxifermin in non-alcoholic steatohepatitis: a randomized, double-blind, placebo-controlled, phase 2a trial. Nat Med 2021; 27(7):1262-1271. DOI: 10.1038/s41591-021-01425-3.
28. Wong N D, Chuang J, Wong K, Pham A, Neff D, Marrett E. Residual dyslipidemia among United States adults treated with lipid modifying therapy (data from National Health and Nutrition Examination Survey 2009-2010). Am J Cardiol 2013; 112(3):373-9. DOI: 10.1016/j.amjcard.2013.03.041.

Example 2

Pegozafermin Provides Beneficial Lipid Effects in Subjects with Severe Hypertriglyceridemia (SHTG) Regardless of Background Lipid Modifying Therapy Status: An Analysis of the Phase 2 ENTRIGUE Study Background:
Fibroblast growth factor 21 (FGF21) is an endogenous stress hormone that regulates glucose and lipid metabolism, and energy expenditure. Pegozafermin (PGZ) is a glycoPEGylated analog of human FGF21 being developed for severe hypertriglyceridemia (SHTG), which was shown to significantly improve lipid profiles in patients with SHTG. Most patients with SHTG are treated with lipid-modifying therapy (LMT). This analysis evaluated the lipid effects of PGZ among subjects based on their background LMT status.

Methods:
ENTRIGUE was a Phase 2 double-blind, randomized, 5-arm trial. PGZ was administered at 4 different doses either once weekly (9 mg, 18 mg, and 27 mg) or once every two weeks (36 mg) versus matching placebo for 8 weeks in patients with fasting triglycerides (TG)≥500 mg/dL and ≤2000 mg/dL. Subjects could be on background LMT, including statins, prescription fish oil, fibrates, or others. The primary endpoint was percent change in TG from baseline.

Results:
Out of 85 subjects randomized and treated with placebo (n=18) or PGZ (n=67), 55% were on background LMT: 45% statin (55% of which were high intensity); 14% prescription fish oil; 7% fibrates. PGZ significantly reduced TG with a placebo-corrected median reduction of 42.6% in subjects on background LMT (95% Confidence Interval −56.29, −22.99; p=0.001). Overall, 79.7% of subjects treated with PGZ reduced their TG level to <500 mg/dL, compared with 29.4% for placebo (85.3% PGZ vs 45.5% placebo in subjects on LMT). Treatment with PGZ significantly reduced non-HDL cholesterol and ApoB, with a placebo-corrected mean reduction of 17.9% (p=0.007) and 11.8% (p=0.019) respectively. These decreases were more robust in subjects on background LMT with placebo-corrected reductions for non-HDL-C and ApoB of 21.7% and 16.8% respectively. LDL-C was not significantly changed in the overall population (LS mean difference of 1.7%, p=0.87). However, PGZ reduced LDL-C in subjects on background LMT (LS mean reduction of 9.0%).

Conclusion:
PGZ significantly reduced TG and atherogenic lipids in patients with SHTG. This analysis demonstrated that PGZ reduced TG when added to background LMT. A phase 3 program to confirm these findings is being planned.

Figure 7A:
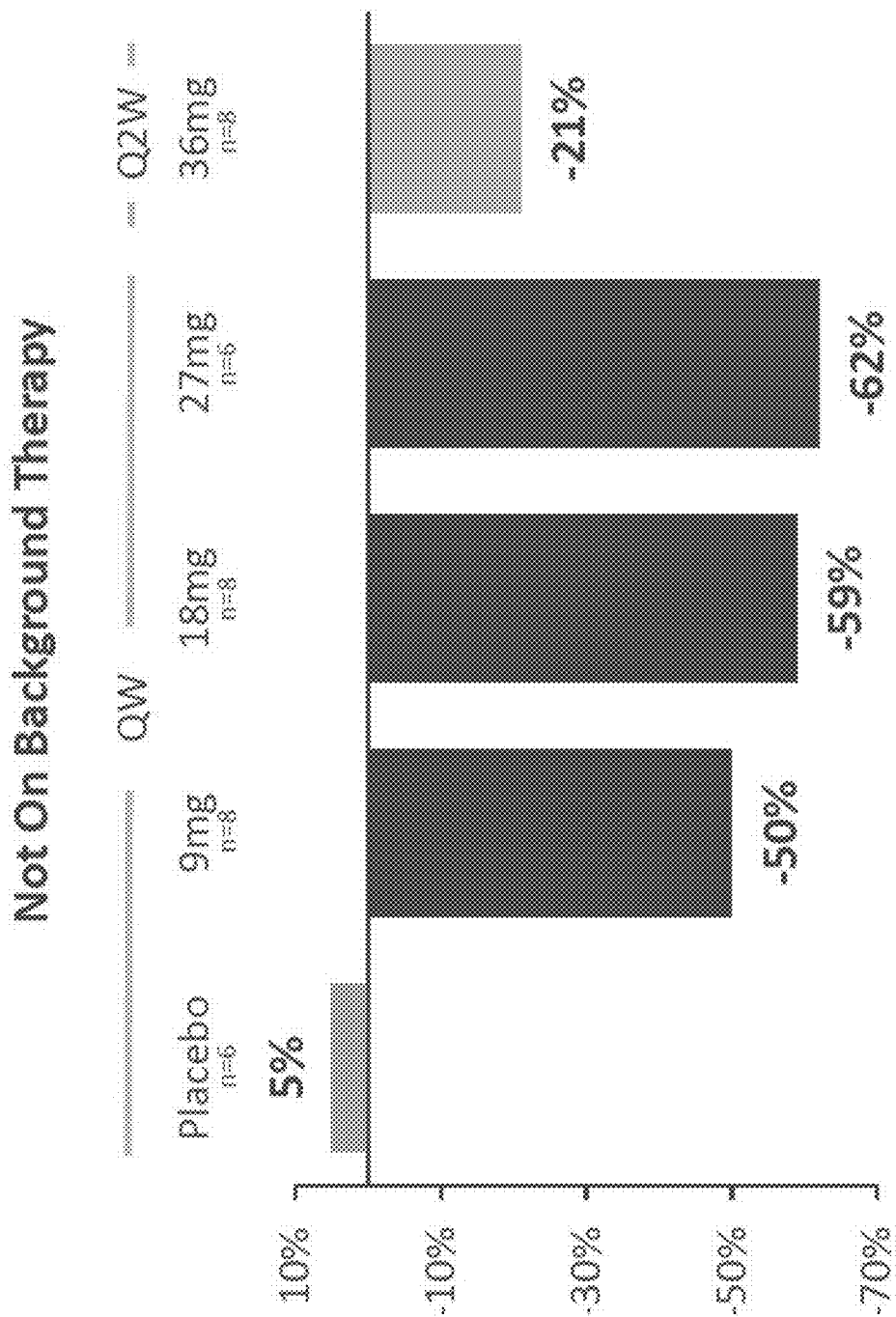
FIG. 7A is a graph showing the median percent change in triglycerides from baseline at week 8 among subjects not on background therapy.
Figure 7B:
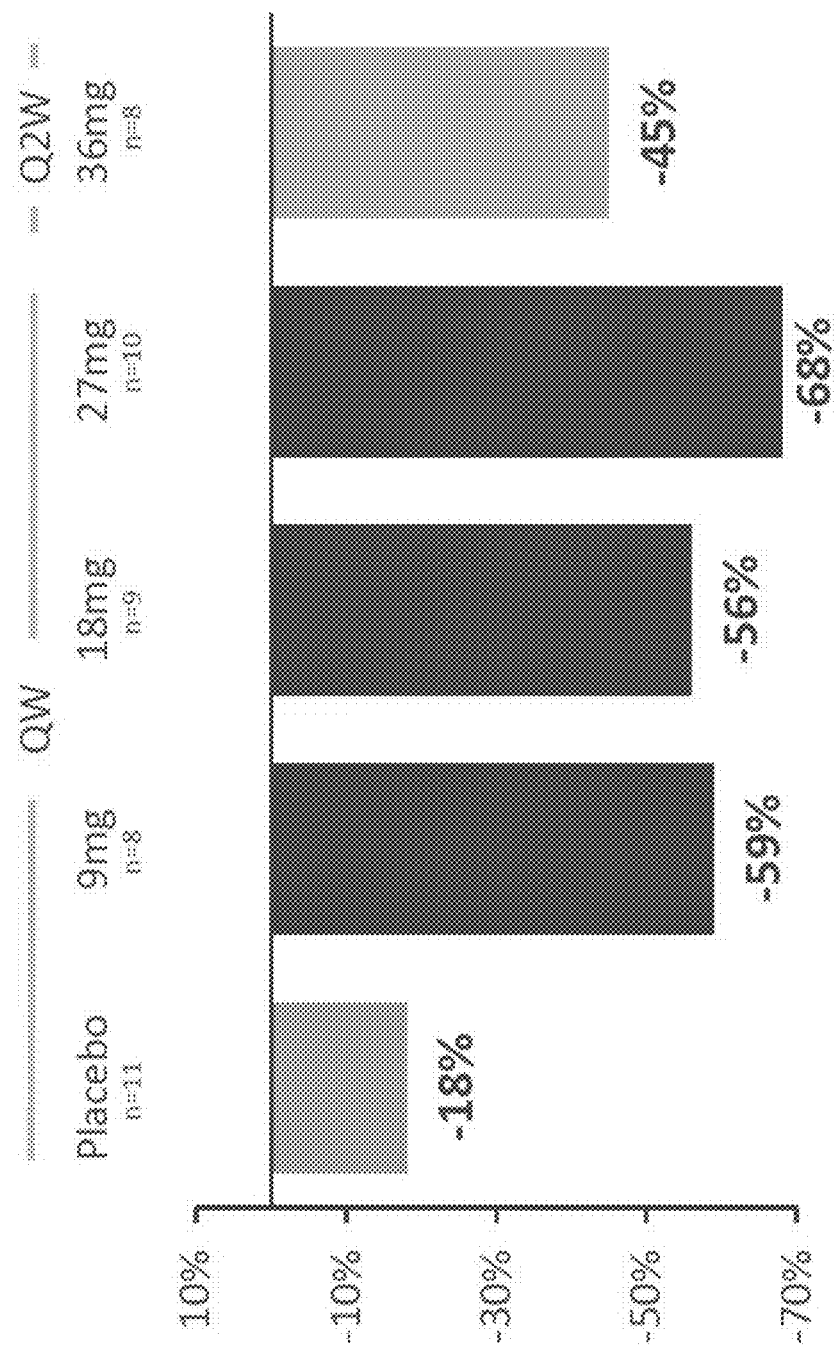
FIG. 7B is a graph showing the median percent change in triglycerides from baseline at week 8 among subjects on background therapy. Pegozafermin led to significant reductions in triglycerides among subjects on background therapy. Background therapy defined as concomitant lipid modifying therapy (LMT).

FIGS. 7A-7B show the median change in triglycerides from baseline at week 8. Pegozafermin shows significant decrease in triglycerides on top of background therapy.

Figure 8:
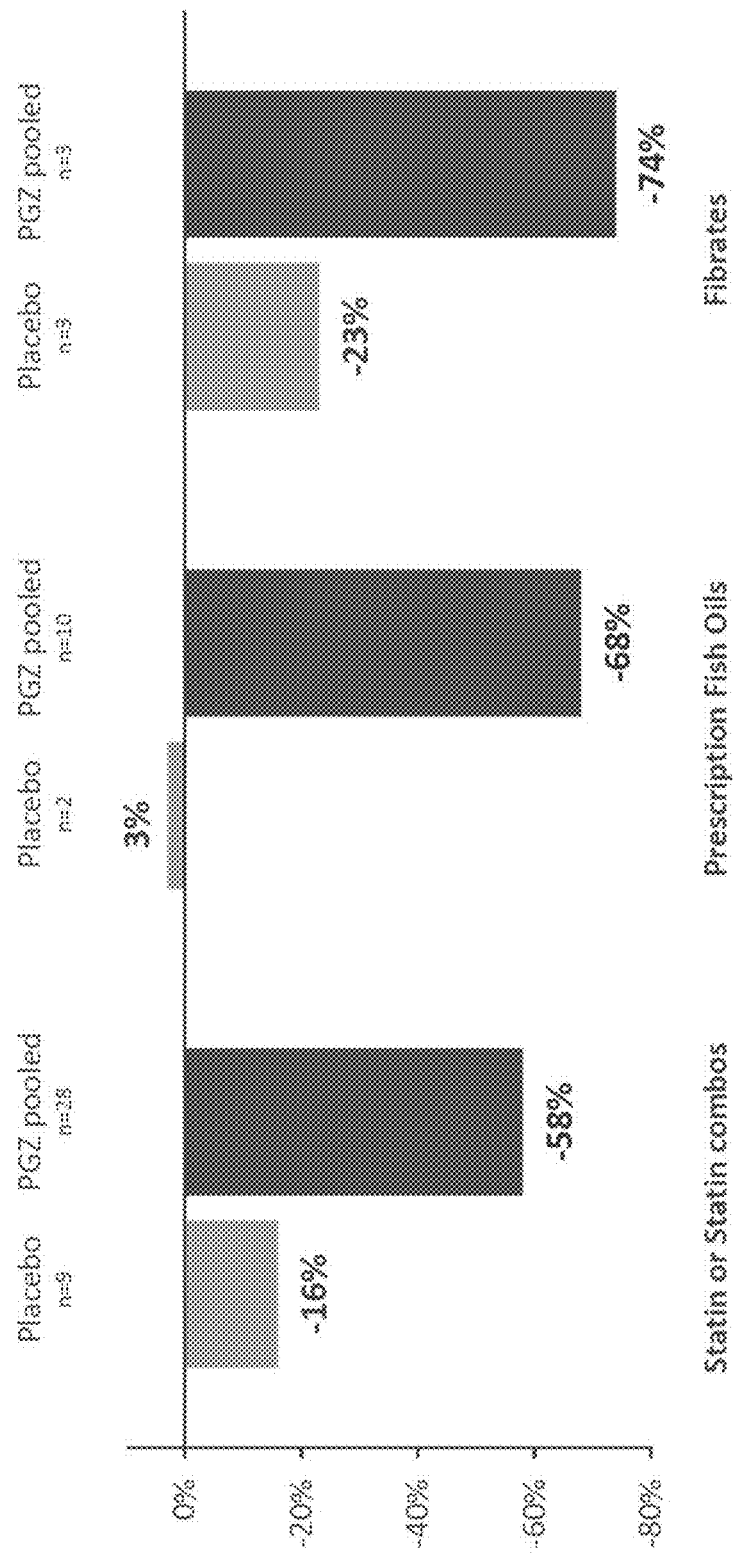
FIG. 8 is a graph showing the median percent change in triglycerides from baseline at week 8 among subjects on statins, prescription fish oils and fibrate. Pegozafermin led to significant reductions in triglycerides among subjects on statins, prescription fish oils and fibrates.

FIG. 8 shows the median change in triglycerides from baseline at week 8. Pegozafermin shows significant decrease in triglycerides on top of statins, prescription fish oils and fibrates.

Figure 9A:
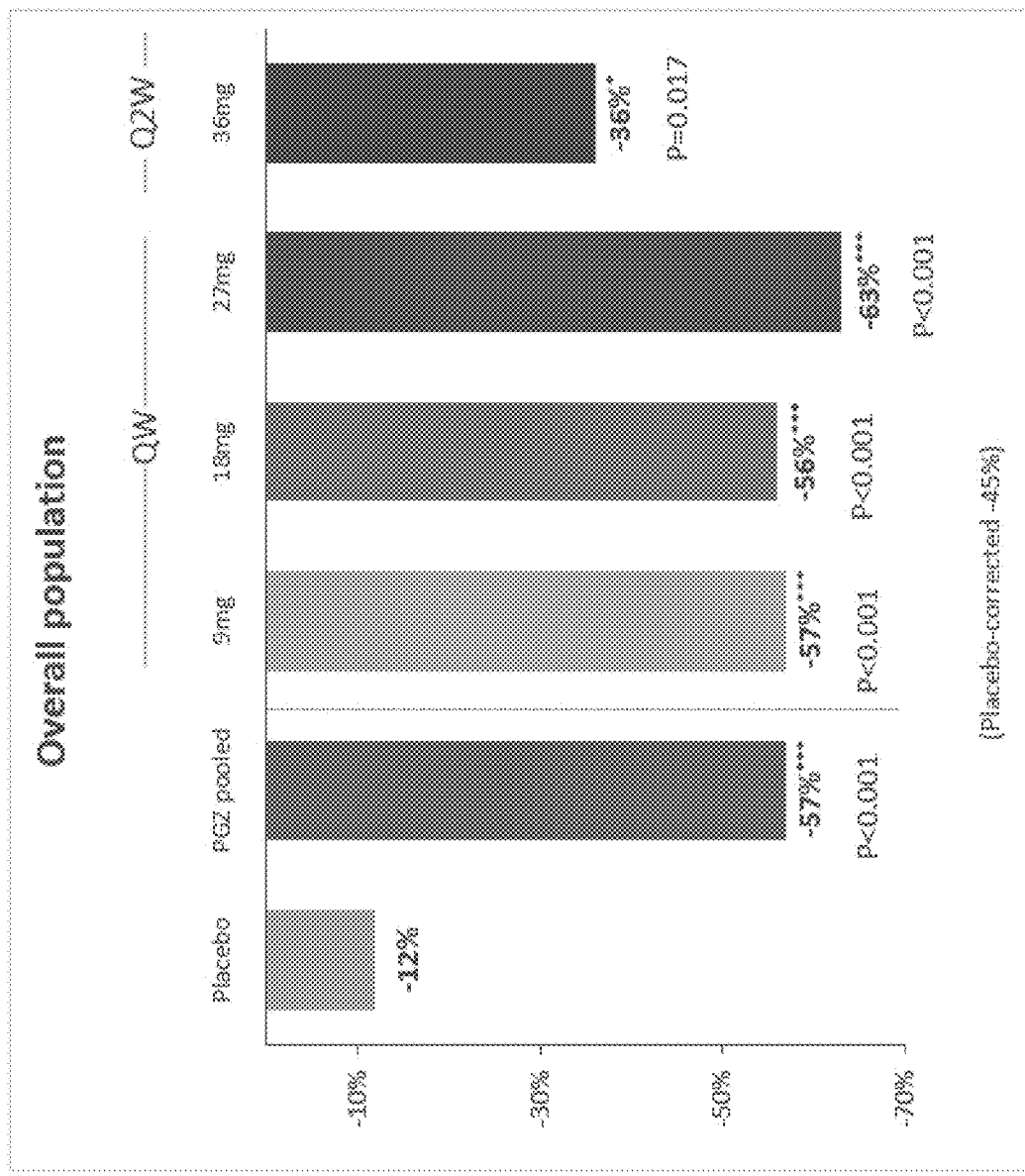
FIG. 9A is a graph showing percent change in triglycerides from baseline among the overall population. p value vs placebo for change from baseline based on van Eltren Test for pooled pegozafermin and Wilcoxon Rank-Sum Test for individual pegozafermin groups; Full Analysis Set; *p<0.05; ***p<0.001 versus placebo. (QW: Every week; Q2W: Every 2 weeks)
Figure 9B:
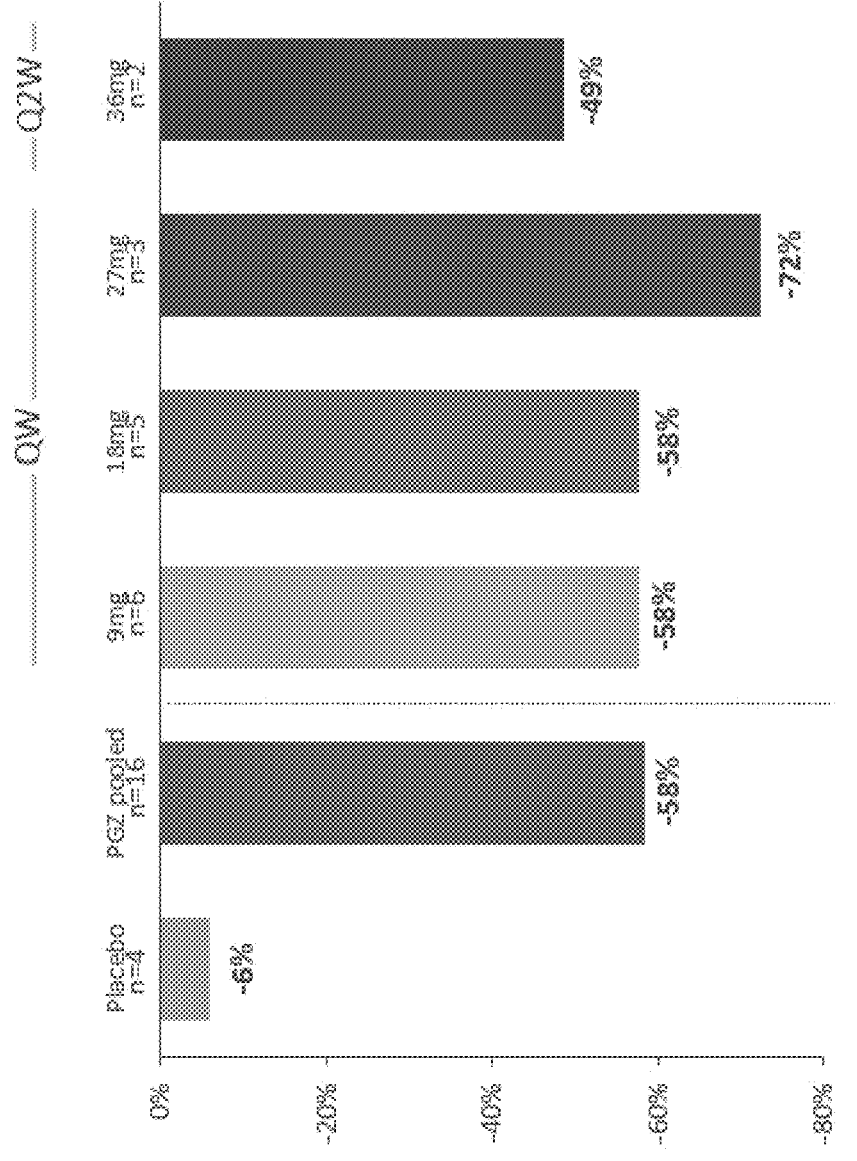
FIG. 9B is a graph showing percent change in triglycerides from baseline among subjects on background high intensity statins. High intensity statins are defined as daily doses of atorvastatin 40-80 mg or rosuvastatin 20-40 mg. Pegozafermin led to reductions in triglycerides among subjects on background high intensity statins. p value vs placebo for change from baseline based on van Eltren Test for pooled pegozafermin and Wilcoxon Rank-Sum Test for individual pegozafermin groups; Full Analysis Set; *p<0.05; ***p<0.001 versus placebo. (QW: Every week; Q2W: Every 2 weeks)

FIGS. 9A-9B show that treatment with pegozafermin led to reductions in triglycerides among subjects on background high intensity statins.

Figure 10:
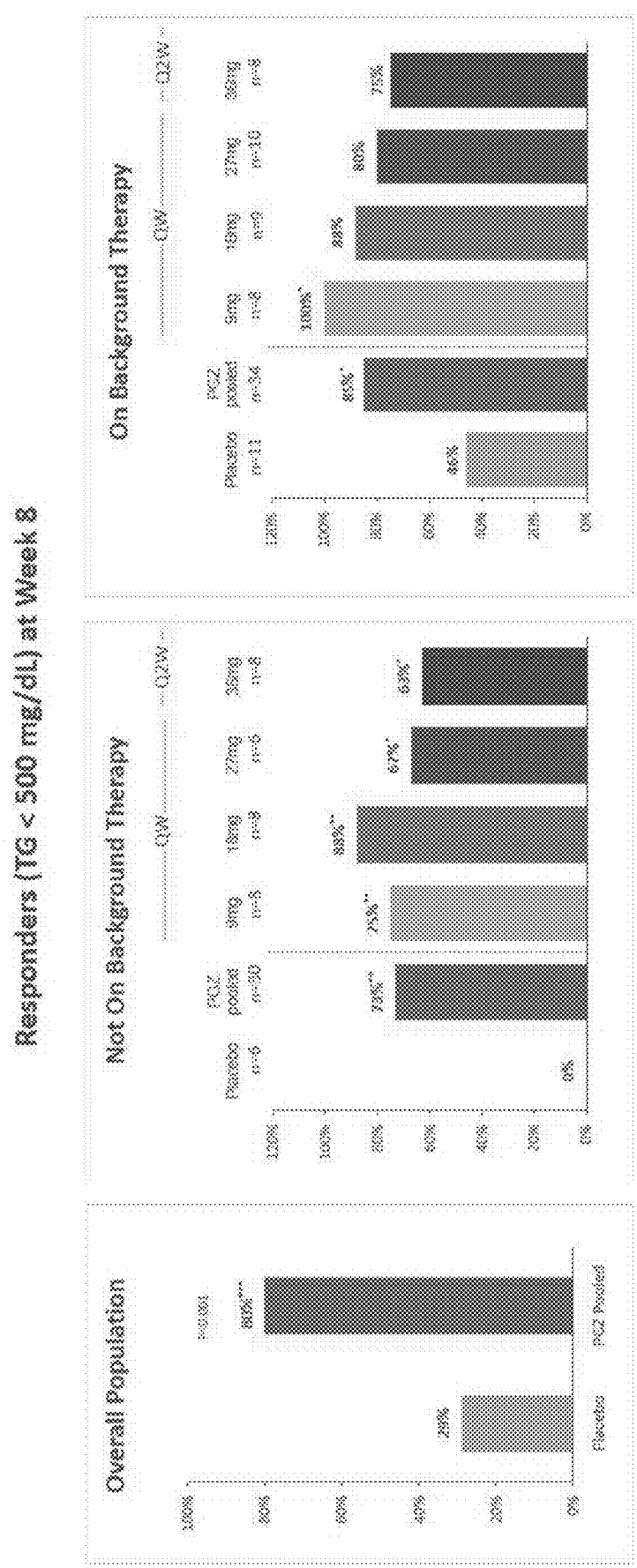
FIG. 10 are graphs showing that pegozafermin treated patients reach initial treatment goal irrespective of background therapy (p value vs placebo for change from baseline based on Cochran Mantel-Haenszel Test for pooled pegozafermin and Wilcoxon Rank-Sum Test for individual pegozafermin groups; Full Analysis Set; *p<0.05; p<0.01; *p<0.001 versus placebo)

FIG. 10 show that patients treated with pegozafermin reach initial treatment goal irrespective of background therapy.

Figure 11:
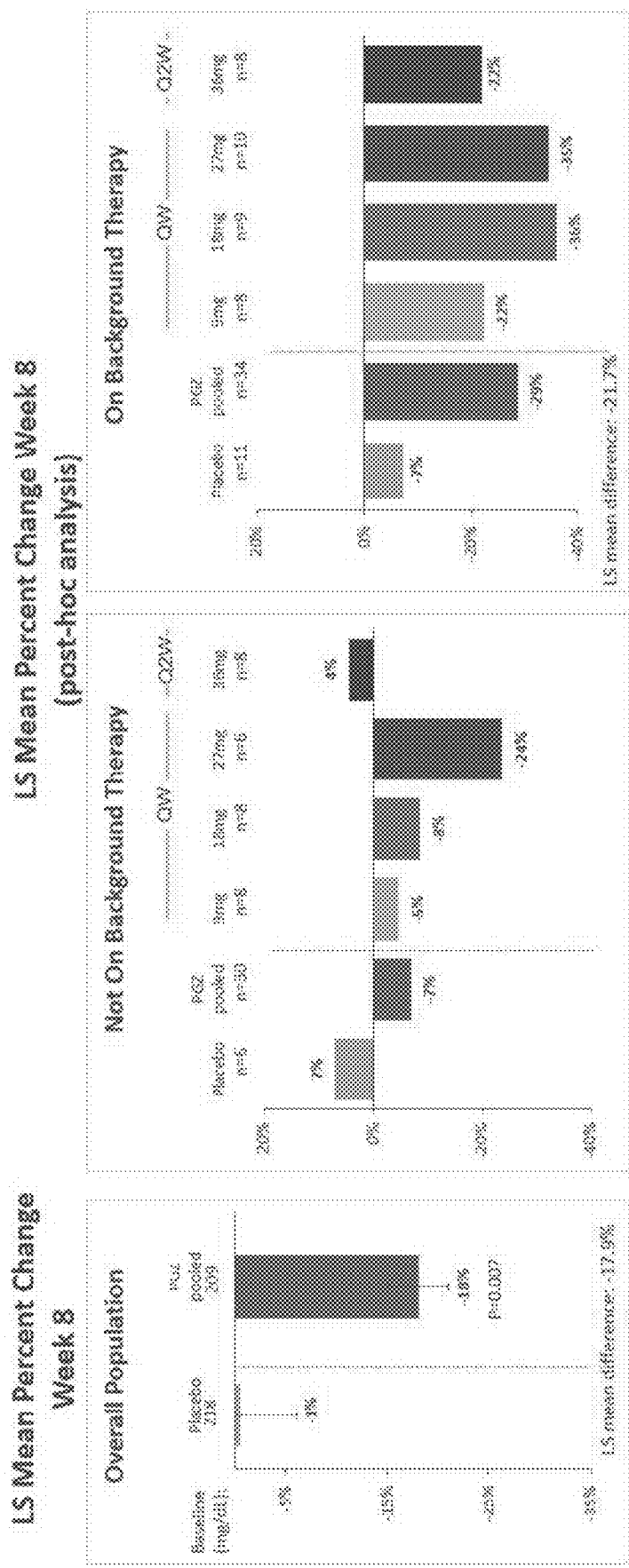
FIG. 11 are graphs showing that pegozafermin treatment led to improvements in non-HDL Cholesterol irrespective of background Therapy. Results are consistent with data from patients on background therapy of statins or statin combos, prescription omega-3s, and fibrates. Least squares means data based on MMRM analysis. Post-hoc analysis; Full Analysis Set.

FIG. 11 shows that pegozafermin treatment led to improvements in non-HDL cholesterol irrespective of background therapy.

Figure 12:
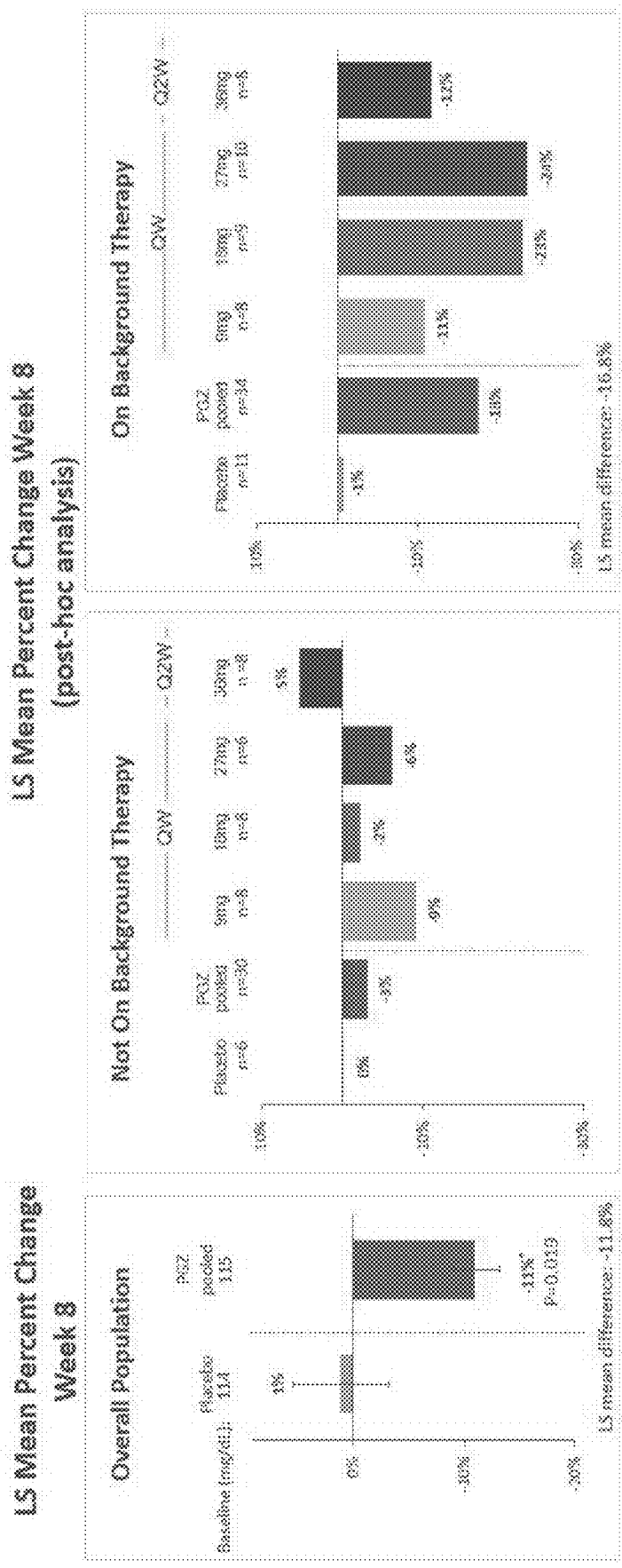
FIG. 12 are graphs showing that pegozafermin treatment led to improvements in Apolipoprotein B irrespective of background therapy. Results are consistent with data from patients on background therapy of statins or statin combos, prescription omega-3s, and fibrates. Least squares means data based on MMRM analysis. Post-hoc analysis; Full Analysis Set.

FIG. 12 shows that pegozafermin treatment led to improvements in Apolipoprotein B irrespective of background therapy.

Figure 13:
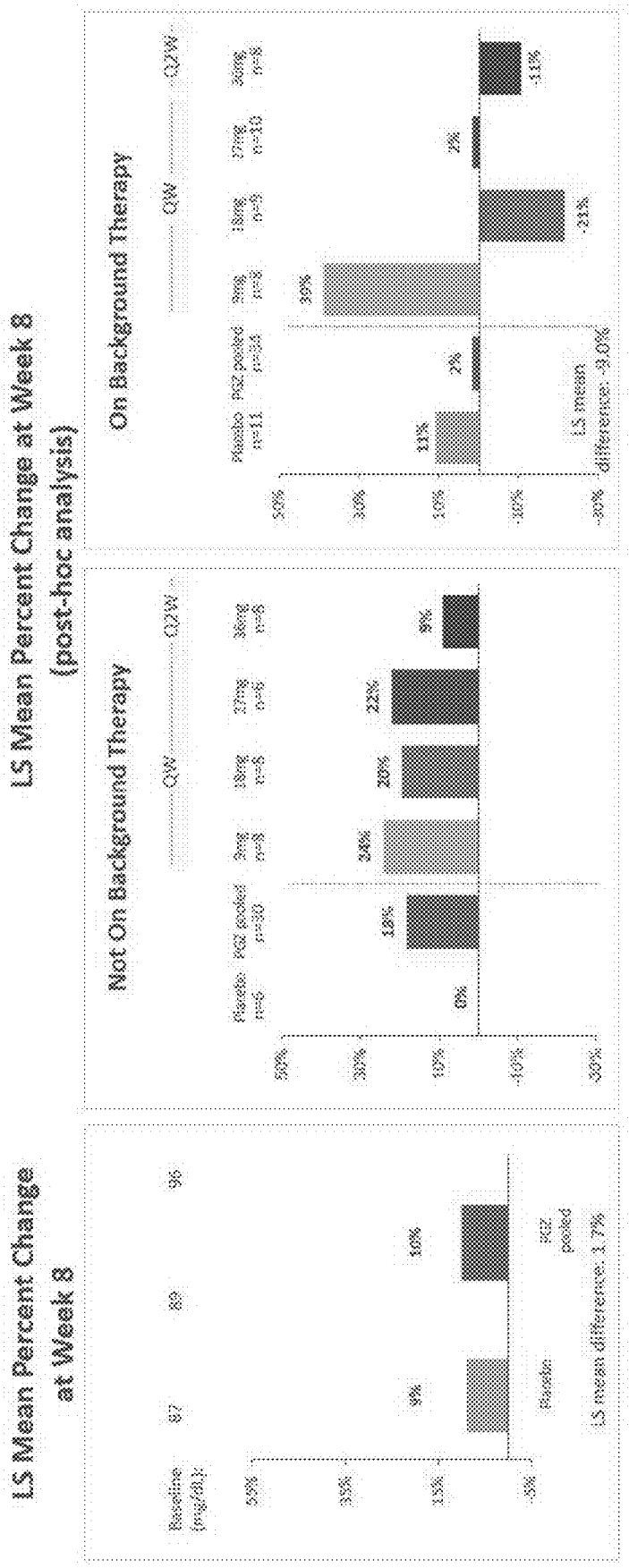
FIG. 13 are graphs showing that there are no significant changes in LDL Cholesterol irrespective of background therapy. Results are consistent with data from patients on background therapy of statins or statin combos, prescription omega-3s, and fibrates. Least squares means data based on MMRM analysis. Post-hoc analysis; Full Analysis Set.

FIG. 13 shows no significant changes in LDL cholesterol irrespective of background therapy.

Figure 14:
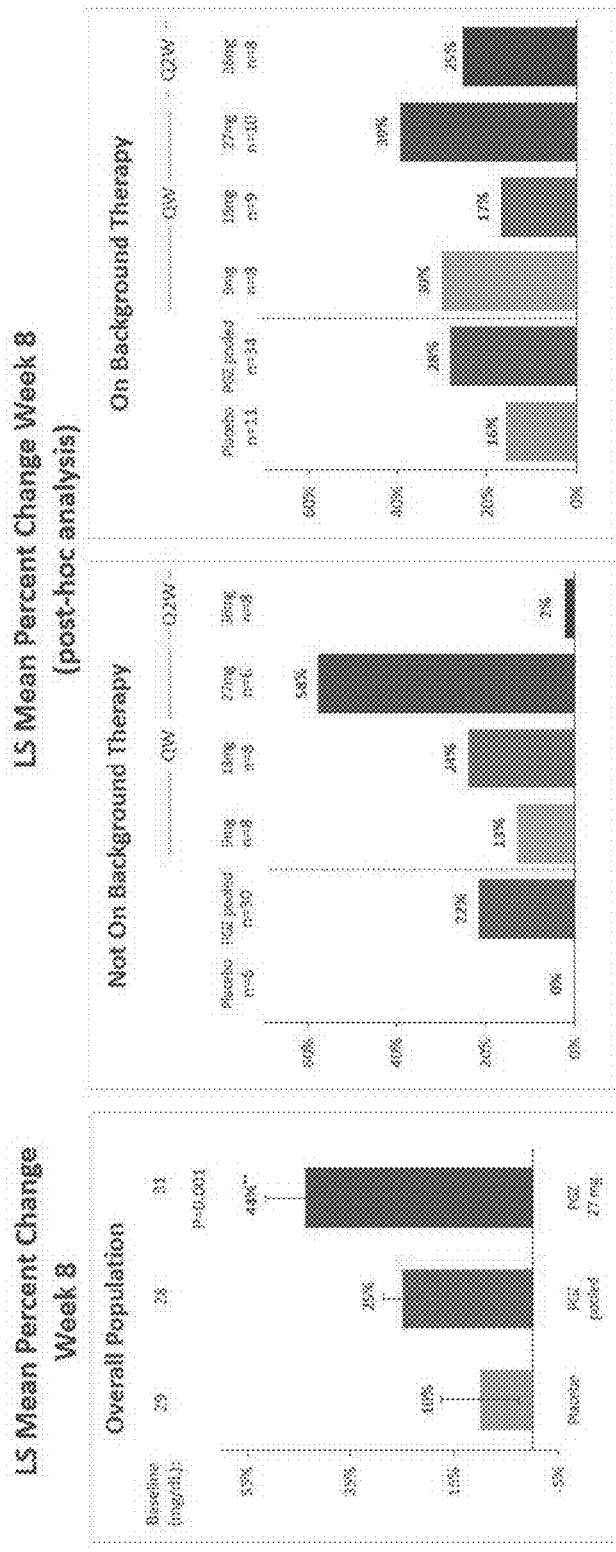
FIG. 14 are graphs showing that pegozafermin treatment led to improvements in HDL Cholesterol irrespective of background therapy. Results are consistent with data from patients on background therapy of statins or statin combos, prescription omega-3s, and fibrates. Least squares means data based on MMRM analysis. Post-hoc analysis; Full Analysis Set.

FIG. 14 shows that pegozafermin treatment led to improvements in HDL cholesterol irrespective of background therapy.

Example 3

The FGF21 Analog Pegozafermin in Severe Hypertriglyceridemia: A Randomized Phase 2 Trial Summary:

Pegozafermin, a long-acting glycopegylated analog of human fibroblast growth factor 21, is in development for treatment of severe hypertriglyceridemia and non-alcoholic steatohepatitis. Here, we report the results of a phase 2, double-blind, randomized, 5-arm trial testing pegozafermin at 4 different doses (n=67; 52 male) versus placebo (n=18; 12 male) for 8 weeks in patients with severe hypertriglyceridemia (triglycerides ≥500 mg/dL and ≤2000 mg/dL). Treated patients showed a significant reduction in median triglycerides for the pooled pegozafermin group versus placebo (57.3% versus 11.9%, difference vs placebo −43.7%, 95% confidence interval [CI]: −57.1%, −30.3%; p<0.001), meeting the primary endpoint of the trial. Reductions in median triglycerides ranged from 36.4% to 63.4% across all treatment arms and were consistent regardless of background lipid-lowering therapy. Results for secondary endpoints included significant decreases in mean ApoB and non-HDL-C concentrations (−10.5% and −18.3% for pooled doses compared to 1.1% and −0.6% for placebo (95% CI: −21.5%, −2.0%; p=0.019 and 95% CI: −30.7%, −5.1%; p=0.007, respectively), as well as a significant decrease in liver fat fraction for pooled treatment (n=17) versus placebo (n=6) [−42.2% pooled pegozafermin, −8.3% placebo; 95% CI: −60.9%, −8.7%; p=0.012], as assessed in a magnetic resonance imaging sub-study. All p-values are based on comparison to the placebo. No serious adverse events were observed to be related to the study drug.

Introduction

Severe hypertriglyceridemia (SHTG; ≥500 mg/dL) increases risk for both acute pancreatitis and cardiovascular disease[1-10]. Although lifestyle modification strategies are often recommended as first-line treatment, triglyceride (TG) levels often remain elevated and require pharmacologic treatment in almost all patients[11-13]. Current therapies for SHTG rarely reduce TGs to desired levels, highlighting the need for new therapeutic options. Moreover, as SHTG is commonly associated with obesity, metabolic syndrome, insulin resistance, type 2 diabetes mellitus (T2DM), and non-alcoholic fatty liver disease (NAFLD)[12,14-16], an ideal therapy should not only lower TG levels, but also provide benefit for other metabolic comorbidities.

Fibroblast growth factor 21 (FGF21) is an endogenous stress hormone that regulates lipid and glucose metabolism and energy expenditure. Preclinical data suggest that in the liver, FGF21 reduces fat via increased adenosine monophosphate-activated protein kinase (AMPK) signaling, which stimulates fatty acid oxidation and decreases de novo lipogenesis (DNL), to mitigate new TG accumulation, and promotes TG secretion in the form of very-low-density lipoprotein (VLDL), to reduce existing fat stores. In adipose tissue, FGF21 improves insulin sensitivity and accelerates TG-rich lipoprotein turnover (e.g., VLDL metabolism) as a result of activating brown adipose tissue and browning of white adipose tissue by inducing the expression of uncoupling protein1[17-22]. Importantly, FGF21 increases low-density lipoprotein receptor (LDLR) expression which could accelerate uptake of the generated VLDL remnants via the ApoE-LDLR pathway[22].

Pegozafermin is a glycopegylated recombinant analog of human FGF21 designed to have a longer half-life than native FGF21 while recapitulating the receptor activity profile of the native hormone. It is being developed for treatment of SHTG and non-alcoholic steatohepatitis (NASH). Pegozafermin has previously demonstrated beneficial effects on serum lipids (triglycerides [TG], low-density lipoprotein cholesterol [LDL-C], non-high-density lipoprotein cholesterol [non-HDL-C], and high-density lipoprotein cholesterol [HDL-C]), insulin resistance, HbA1c, body weight, and liver fat in patients with NASH.[23-24] Though previous clinical trials with pegozafermin and other FGF21 analogs have consistently demonstrated improvements in lipids in both healthy volunteers and patients with NASH or diabetes, FGF21 analogs have not been assessed in SHTG [23,25-29]. To our knowledge, the ENTRIGUE trial was the first clinical trial to investigate an FGF21 analog as a novel therapeutic agent for the treatment of SHTG.

Methods

Trial Design

The ENTRIGUE trial was a randomized, double-blind, placebo-controlled, dose-ranging, phase 2 trial designed to assess the efficacy, safety, and tolerability of pegozafermin administered subcutaneously once-weekly (QW) or every 2 weeks (Q2W) in participants with SHTG. Participants with screening fasting TG≥500 mg/dL (5.6 mmol/L) and ≤2000 mg/dL (22.6 mmol/L) were eligible to enroll regardless of background lipid-modifying therapy of statins, prescription omega-3 fatty acids and fibrates (fibrate expansion cohort only). Sex of participants, which was determined by self-report, was not considered in the study design.

Participants were enrolled into one of two cohorts: 1) main study cohort (could not be on concurrent fibrate therapy); or 2) fibrate expansion cohort. The fibrate expansion cohort was initiated as a protocol amendment (v2.0) after the start of the study to evaluate pegozafermin in subjects on stable fibrate therapy, as these medications are commonly used to treat SHTG. The main study cohort was randomized 1:1:1:1:1 to one of four doses of pegozafermin (9 mg QW, 18 mg QW, 27 mg QW, or 36 mg Q2W) or placebo, and the fibrate cohort was randomized 1:1 to either pegozafermin 27 mg QW or placebo QW for 8 weeks (FIG. 4). All participants were stratified by TG level (<750 mg/dL or ≥750 mg/dL [8.5 mmol/L]), with additional stratification in the main cohort by whether they were taking background therapy. An MRI-PDFF sub-study was initiated at sites able to perform MRI-PDFF imaging as participants in the fibrate expansion cohort were required to have MRI-PDF≥6.0% at enrollment. Twenty-four subjects (6 from the fibrate expansion cohort) received baseline MRI-PDFF measurements, of whom 23 completed a follow-up scan at the end of the study period. After completing the 8-week treatment period, all participants underwent a 4-week safety follow-up period.

Participants were required to fast for 12-14 hours and abstain from alcohol for 48 hours prior to each lipid assessment throughout the study. Following a lifestyle stabilization period (4 weeks if on stable approved lipid-modifying therapy; up to 6 weeks if washing out ineligible lipid-modifying therapy), an ~2-week qualification period occurred consisting of two fasting TG assessments at least one week apart. If mean TG levels from these two laboratory evaluations were not within the inclusion range, an additional third assessment was collected at least one week apart from the previous assessment. The mean TG value from the last two assessments served as TG qualification for the study and was the basis for participant TG stratification at randomization. Exclusion criteria included uncontrolled or recent diagnosis of hypertension, uncontrolled or recent diagnosis of T2DM within 6 months of screening, HbA1c≥9.5%, BMI>45 kg/m$^2$, or cardiovascular or cerebrovascular disease.

Study Outcomes

The study objectives and endpoints were similar for the main study and fibrate cohorts. Given the small number of patients enrolled in the fibrate cohort (n=6), data were pooled and presented for both cohorts. The primary efficacy endpoint was percentage change in serum TG from baseline to week 8. Secondary efficacy endpoints included select serum lipids and lipoproteins, metabolic markers, and change in liver fat content as assessed by MRI-PDFF. Safety endpoints included overall safety and tolerability assessments, liver function markers, and immunogenicity.

Baseline TG level was defined as the average of randomization day assessment collected pre-dose and the preceding two lipid-qualifying assessments collected during the TG qualifying period. The TG value at week 8 was defined as the average of TG values at week 7 and week 8. In case of missing TG values at week 7 or 8, the non-missing result was used as the week 8TG value. Responder analysis of TG reduction at various threshold levels was performed and proportion of participants with TG normalization (<150 mg/dL) was also analyzed.

Statistical Analysis

The study was designed to have at least 86% power to detect a 45% difference in TG between each of the pegozafermin arms and placebo groups, assuming 50% reduction in pegozafermin dose groups and 5% reduction in the placebo group. Both pooled pegozafermin from all dose groups and individual pegozafermin dose groups were compared with placebo. All analyses were performed at a two-sided alpha level of 0.05, without adjustment for multiplicity, and confidence intervals (CI) were two-sided (95%). Summary descriptive statistics were used to present demographics and baseline characteristics, safety endpoints, and pharmacodynamic parameters.

Efficacy analyses were conducted with the full analysis set, which included patients with at least one post-baseline TG level. Normality test was performed and if normality was severely violated then non-parametric tests were performed. A pre-specified QQ plot suggested the distribution of TG data was highly skewed and deviated from the normality assumption required for MMRM method. Therefore, the primary efficacy analysis was performed using a non-parametric van Elteren test, stratified by baseline TG level and background lipid therapy, to test the treatment difference using pooled data. The location shift estimate and Hodges-Lehmann 2-tailed 95% CI are presented. Comparison between the individual pegozafermin dose group and placebo used the unstratified Wilcoxon rank-sum test due to low sample size. If the number of participants within any subgroup was too low for meaningful comparison (n<6), only descriptive analysis was performed. Placebo-corrected change was defined as the difference in the change from baseline in a pegozafermin dose group and the change from baseline in the placebo group. Each week-8 value was defined as the average of the week-7 value, the week-8 value and any early termination values that fell within the analysis window.

Secondary efficacy endpoints were analyzed by mixed model repeated measurements. If the mixed model assumption was severely violated, non-parametric methods were used for the analysis. The proportion of participants with TG<500 mg/dL at week 8 was analyzed using stratified the Cochran Mantel Haenszel (CMH) method using patients with both baseline and week 8TG results. Unstratified chi-square test was performed for comparisons between placebo and the individual pegozafermin dose group. Statistical analysis was performed using SAS®, version 9.4 or later.

Results

Patient Characteristics 489 patients underwent screening, with 85 patients (17.4%) randomized and treated. Among the patients treated with pegozafermin, the distribution was as follows: placebo, n=18; 9 mg QW, n=16; 18 mg QW, n=17; 27 mg QW, n=18; and 36 mg Q2W, n=16. Post-baseline TG levels were available for the 82 patients in the full analysis set. The baseline characteristics of the patients, shown in Table below, were reasonably balanced across groups, with a mean age of 53.7 years, 75.3% male, mean BMI 33.1 kg/m$^2$, 50.6% with T2DM, 55.3% on background lipid-lowering therapy (including statins, prescription omega-3 fatty acids, fibrates [fibrate cohort], bempedoic acid, and ezetimibe) and a median baseline TG level of 622.0 mg/dL. Other baseline lipids were at typical mean levels for this population: LDL-C, 89.1 mg/dL; HDL-C, 28.4 mg/dL; and non-HDL-C, 211.5 mg/dL. At clinical sites with MRI capability, a subset of patients (n=24) underwent baseline proton density fat-fraction (PDFF) evaluation to measure hepatic steatosis. All patients assessed by MRI-PDFF had evidence of fatty liver (>5% hepatic fat) at baseline, with an overall mean value of 20.1% (see Table below).

TABLE 6

Demographics and Baseline Characteristics.

| Characteristic, mean or % | Placebo (n = 18) | PGZ Pooled (n = 67) | PGZ 9 mg QW (n = 16) | PGZ 18 mg QW (n = 17) | PGZ 27 mg QW (n = 18) | PGZ 36 mg Q2W (n = 16) | Total (n = 85) |
|---|---|---|---|---|---|---|---|
| Age, years | 57.5 | 52.7 | 54.6 | 49.2 | 53.9 | 53.1 | 53.7 |
| Male, % | 66.7 | 77.6 | 68.8 | 82.4 | 72.2 | 87.5 | 75.3 |
| White, % | 94.4 | 95.5 | 93.8 | 100 | 100 | 87.5 | 95.3 |
| BMI, kg/m$^2$ | 33.1 | 33.1 | 32.9 | 32.3 | 34.2 | 32.9 | 33.1 |
| Type 2 diabetes, n (%) | 11 (61.1) | 32 (47.8) | 9 (56.3) | 6 (35.3) | 10 (55.6) | 7 (43.8) | 43 (50.6) |

TABLE 6-continued

Demographics and Baseline Characteristics.

| Characteristic, mean or % | Placebo (n = 18) | PGZ Pooled (n = 67) | PGZ 9 mg QW (n = 16) | PGZ 18 mg QW (n = 17) | PGZ 27 mg QW (n = 18) | PGZ 36 mg Q2W (n = 16) | Total (n = 85) |
|---|---|---|---|---|---|---|---|
| Hypertension, n (%) | 13 (72.2) | 39 (58.2) | 11 (68.8) | 7 (41.2) | 11 (61.1) | 10 (62.5) | 52 (61.2) |
| Triglyceride, mg/dL (median) | 574.8 | 631.3 | 593.3 | 633.3 | 645.3 | 688.5 | 622.0 |
| Triglyceride <750 mg/dL at screening, % | 66.7 | 59.7 | 62.5 | 58.8 | 61.1 | 56.3 | 61.2 |
| Triglyceride >750 mg/dL at screening, % | 33.3 | 40.3 | 37.5 | 41.2 | 38.9 | 43.8 | 38.8 |
| non–HDL cholesterol, mg/dL | 219.6 | 209.3 | 216.2 | 203.2 | 203.4 | 215.4 | 211.5 |
| HDL cholesterol, mg/dL | 28.3 | 28.4 | 30.7 | 27.3 | 30.6 | 24.8 | 28.4 |
| LDL cholesterol, mg/dL | 87.9 | 89.4 | 91.6 | 88.3 | 97.3 | 79.5 | 89.1 |
| VLDL cholesterol, mg/dL | 133.2 | 117.8 | 123.2 | 115.0 | 104.7 | 130.1 | 120.9 |
| VLDL triglyceride, mg/dL | 610.2 | 633.6 | 588.0 | 574.2 | 590.0 | 791.4 | 628.9 |
| Total cholesterol, mg/dL | 247.9 | 237.6 | 246.9 | 230.5 | 234.0 | 240.1 | 239.8 |
| Apolipoprotein B, mg/dL | 116.3 | 115.3 | 120.1 | 115.3 | 119.3 | 105.9 | 115.5 |
| Apolipoprotein C3, mg/dL | 29.7 | 29.5 | 29.4 | 28.0 | 30.7 | 30.0 | 29.6 |
| Apolipoprotein A1, mg/dL | 138.8 | 137.1 | 143.3 | 137.7 | 141.0 | 125.9 | 137.5 |
| Lipoprotein (a), nmol/L | 42.5 | 45.4 | 48.2 | 21.1 | 55.1 | 58.3 | 44.8 |
| Free fatty acids, mmol/L | 0.6 | 0.5 | 0.5 | 0.6 | 0.6 | 0.5 | 0.5 |
| HbA1c, % | 6.28 | 6.55 | 6.63 | 6.59 | 6.61 | 6.37 | 6.50 |
| HbA1c ≥6.5%, n (%) | 7 (38.9) | 30 (44.8) | 9 (56.3) | 6 (35.3) | 9 (50.0) | 6 (37.5) | 37 (43.5) |
| High-sensitivity C-reactive protein, mg/L | 4.6 | 4.5 | 5.9 | 3.6 | 3.2 | 5.7 | 4.6 |
| Adiponectin (μg/mL) | 4.0 | 3.3 | 3.3 | 2.4 | 4.9 | 2.5 | 3.5 |
| Fasting plasma glucose, mg/dL | 124.4 | 148.7 | 158.5 | 139.3 | 157.5 | 139.0 | 143.6 |
| ALT, U/L | 29.1 | 33.9 | 36.3 | 36.9 | 33.0 | 29.2 | 32.8 |
| AST, U/L | 24.2 | 24.7 | 26.7 | 27.6 | 23.7 | 20.6 | 24.6 |
| Background lipid-modifying therapy, n (%) | | | | | | | |
| Any | 11 (61.1) | 36 (53.7) | 8 (50.0) | 9 (52.9) | 11 (61.1) | 8 (50.0) | 47 (55.3) |
| Statins | 9 (50.0) | 29 (43.3) | 6 (37.5) | 9 (52.9) | 7 (38.9) | 7 (43.8) | 38 (44.7) |
| High intensity statins | 4 (22.2) | 17 (25.4) | 6 (37.5) | 5 (29.4) | 4 (22.2) | 2 (12.5) | 21 (24.7) |
| Prescription fish oils | 2 (11.1) | 10 (14.9) | 1 (6.3) | 2 (11.8) | 4 (22.2) | 3 (18.8) | 12 (14.1) |
| Fibrates | 3 (16.7) | 3 (4.5) | 0 | 0 | 3 (16.7) | 0 | 6 (7.1) |
| Ezetimibe | 1 (5.6) | 8 (11.9) | 2 (12.5) | 2 (11.8) | 2 (11.1) | 2 (12.5) | 9 (10.6) |
| Bempedoic acid | 0 | 1 (1.5) | 0 | 1 (5.9) | 0 | 0 | 1 (1.2) |
| Liver fat fraction by MRI-PDFF, % | 16.5 (n = 24) | 21.3 (n = 6) | 19.8 (n = 18) | 18.0 (n = 3) | 22.4 (n = 5) | 25.5 (n = 7) | 20.1 (n = 24) |

ALT, alanine aminotransferase;
AST, aspartate aminotransferase;
BMI, body mass index; HbA1c, glycated hemoglobin;
HDL, high density lipoprotein;
LDL; low density lipoprotein;
MRI-PDFF, magnetic resonance imagining proton density fat fraction;
PGZ, pegozafermin;
QW, once weekly;
Q2W, once every 2 weeks;
VLDL, very low density lipoprotein.

Figure 15:
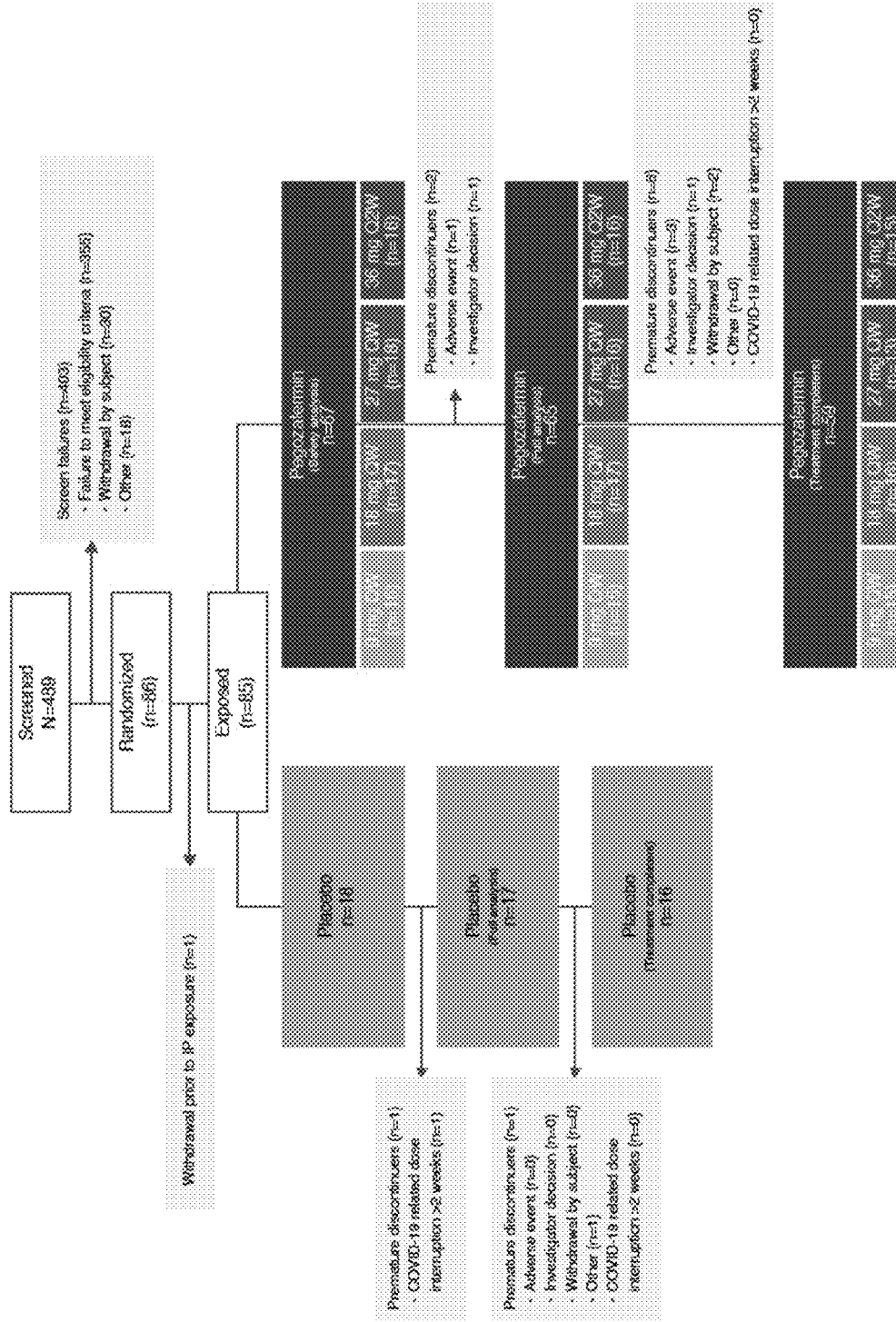
FIG. 15 is a patient flow diagram. QW, once-weekly; Q2W, once every 2 weeks.

Patient disposition and population analysis sets are presented in FIG. 15 and Table 3.

Efficacy Endpoints

Effect on Triglyceride Levels (Primary Endpoint)

Figure 16A:
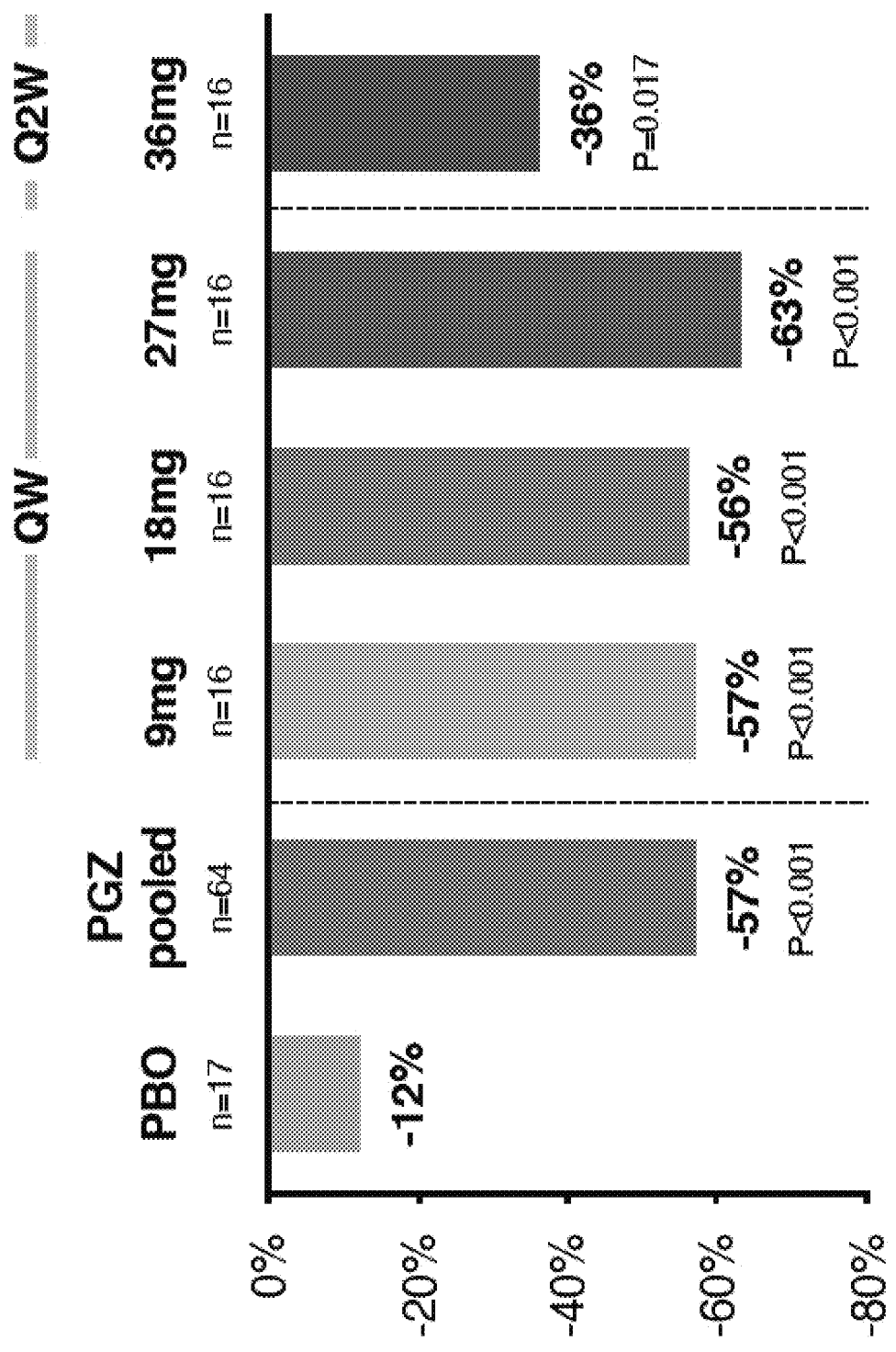
FIGS. 16A-16F are graphs showing the effect of pegozafermin on serum triglycerides.
Figure 16B:
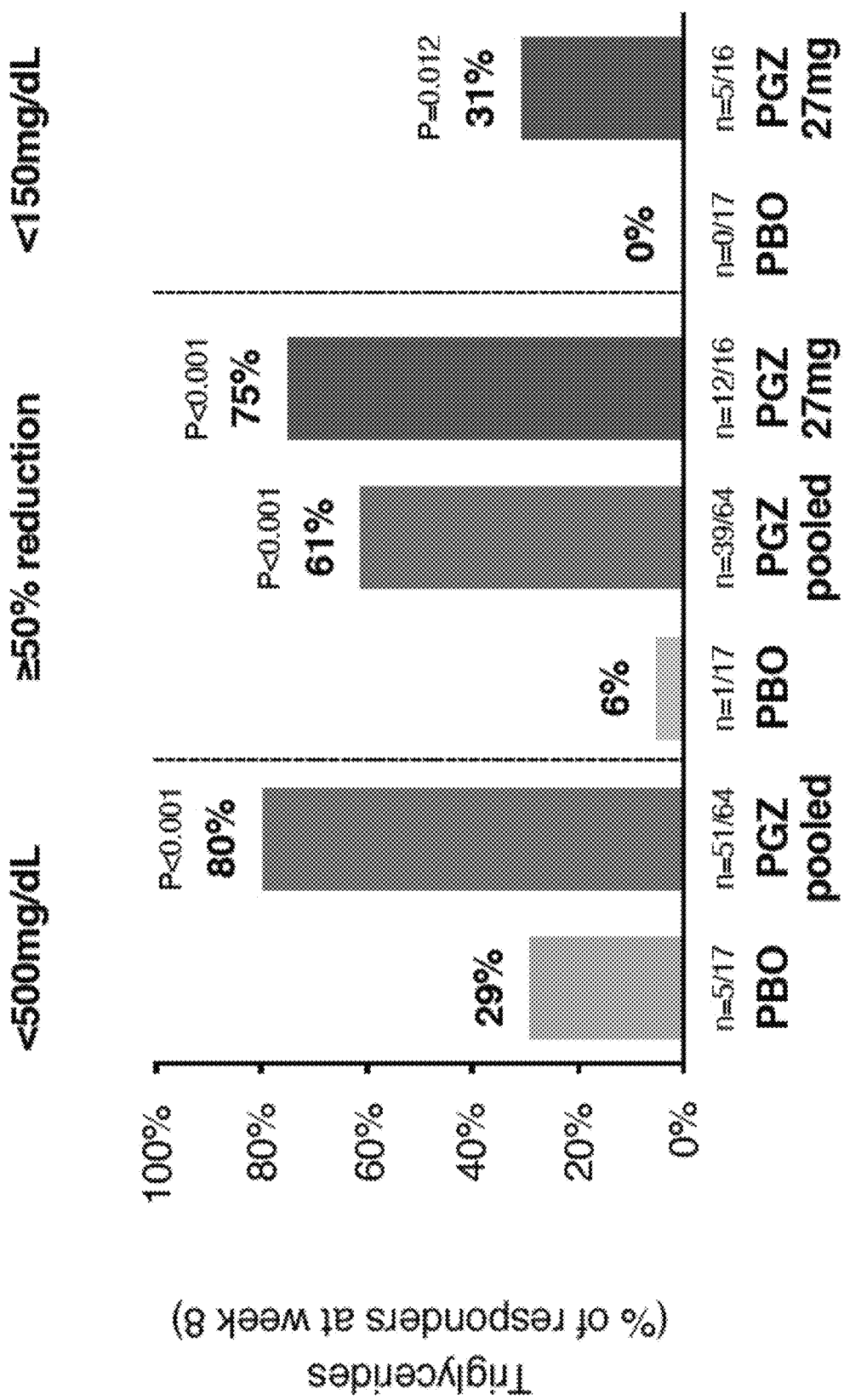
Figure 16C:
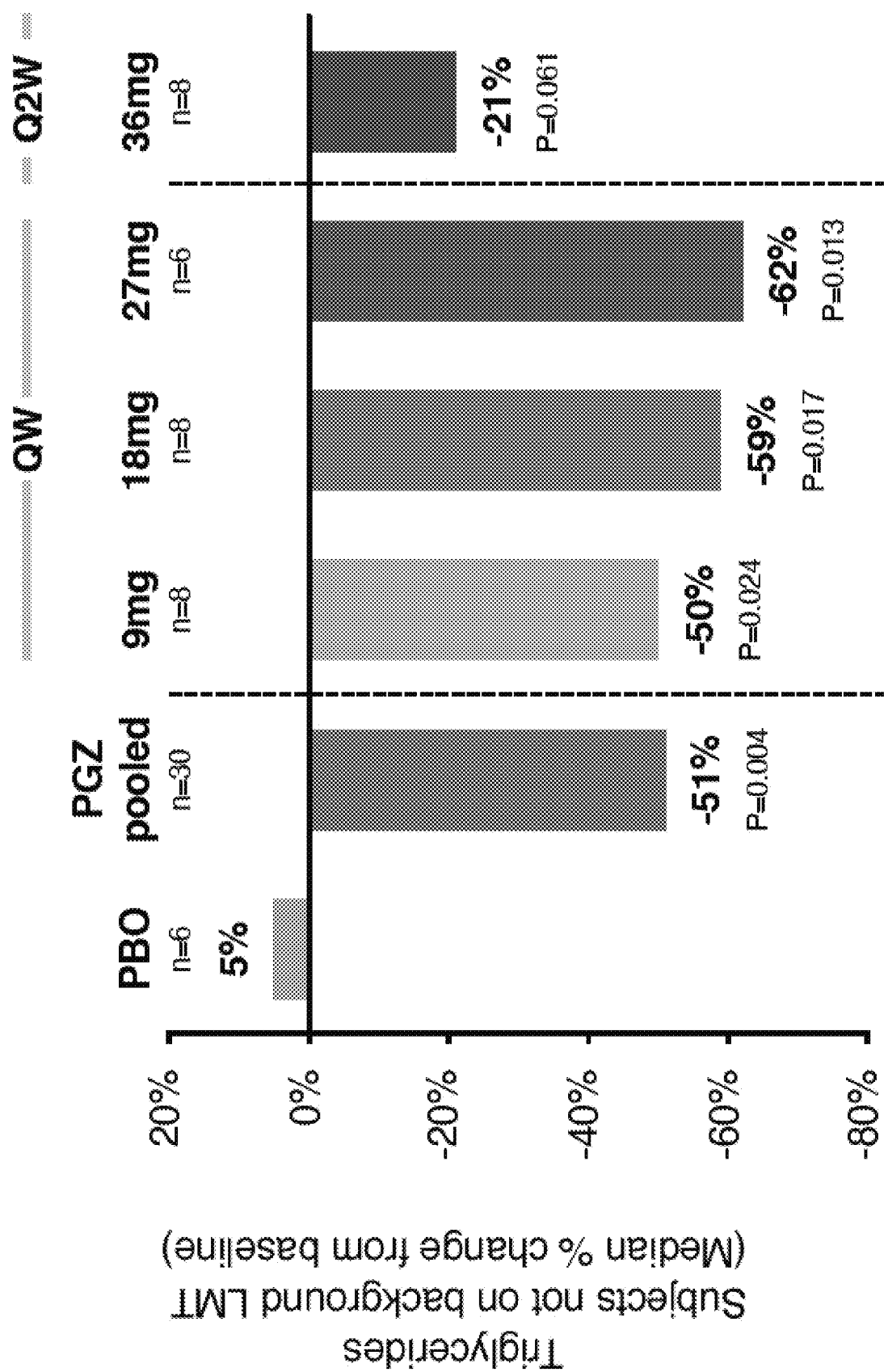
Figure 16D:
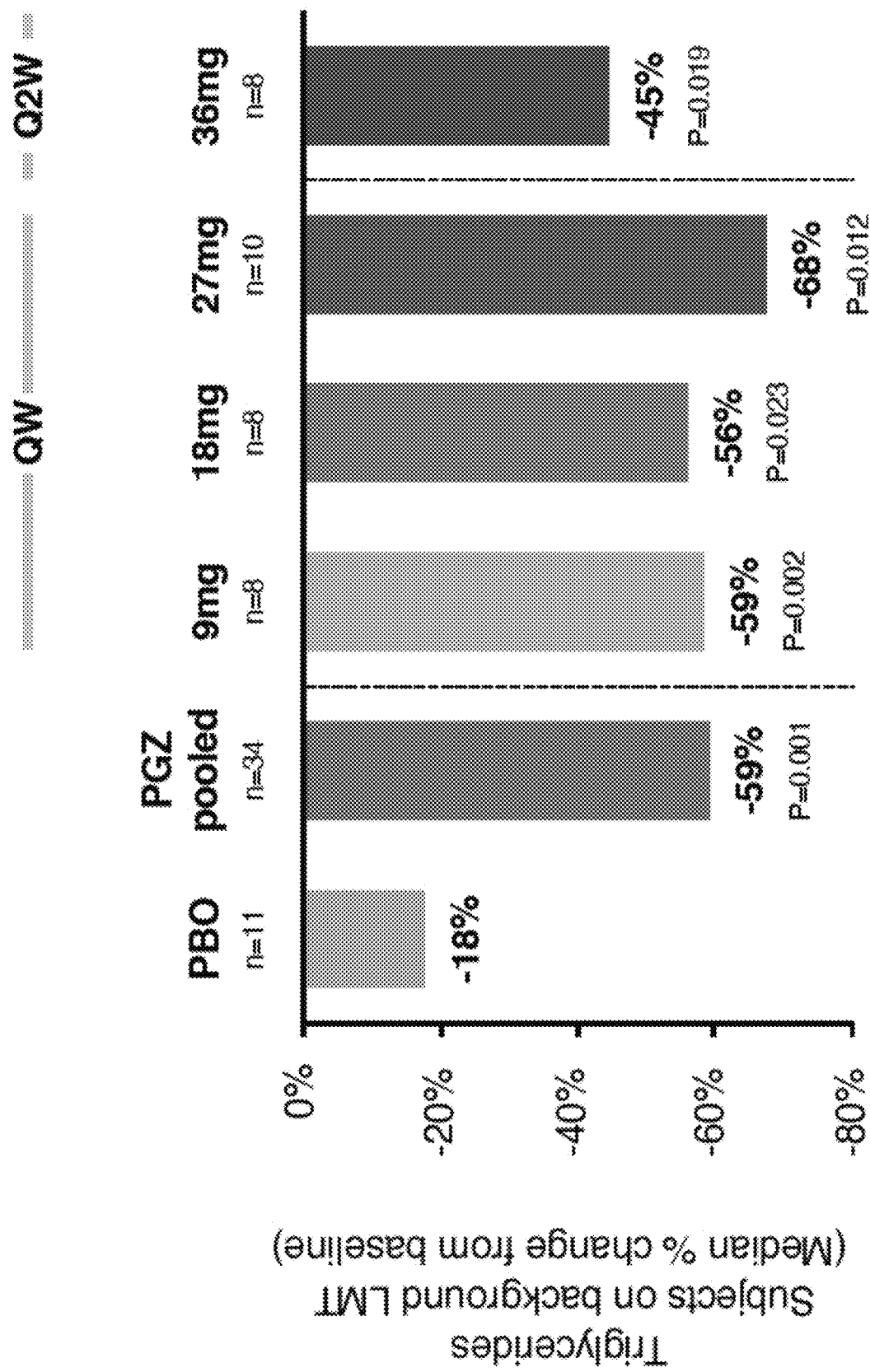
Figure 16E:
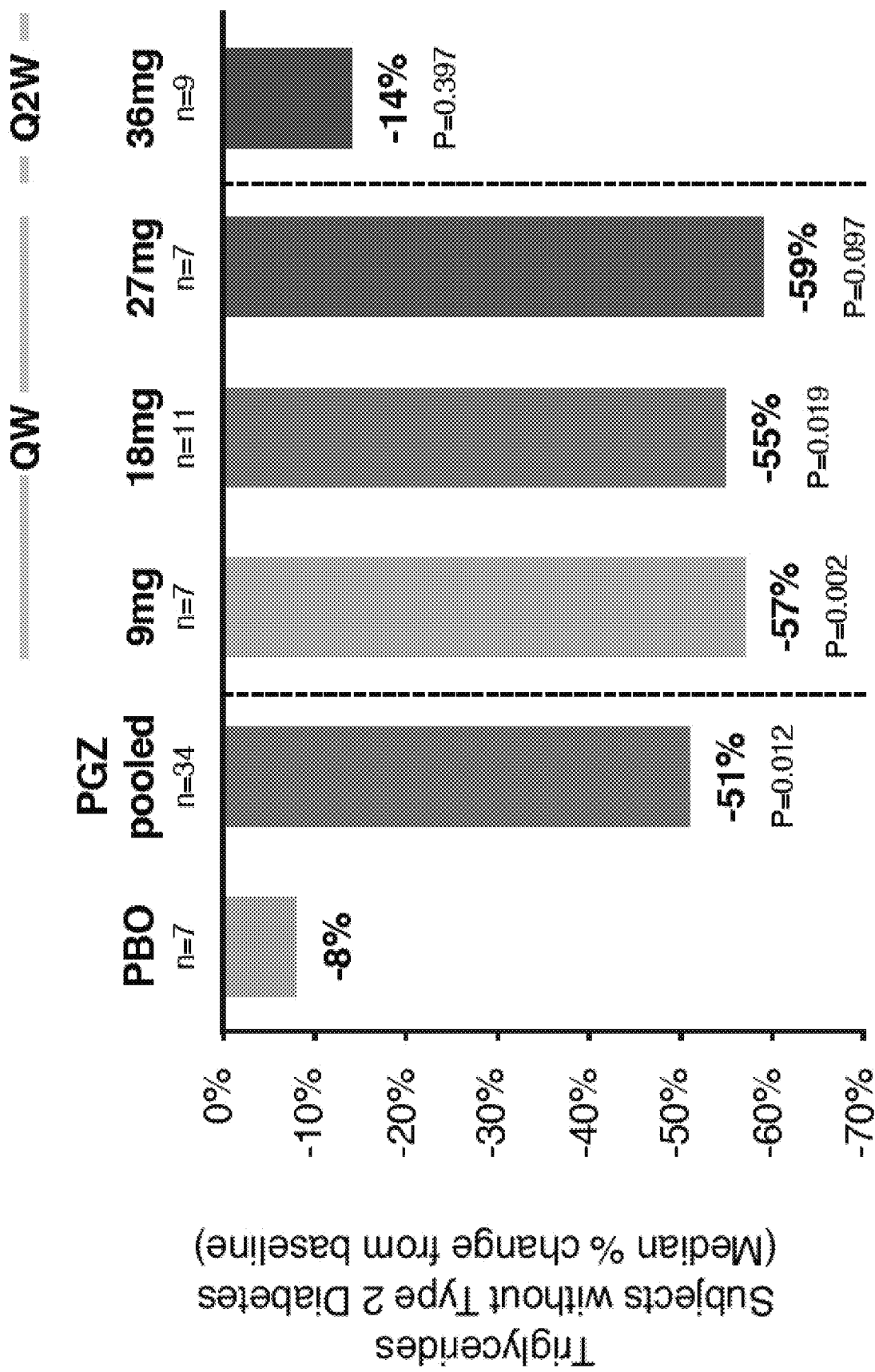
Figure 16F:
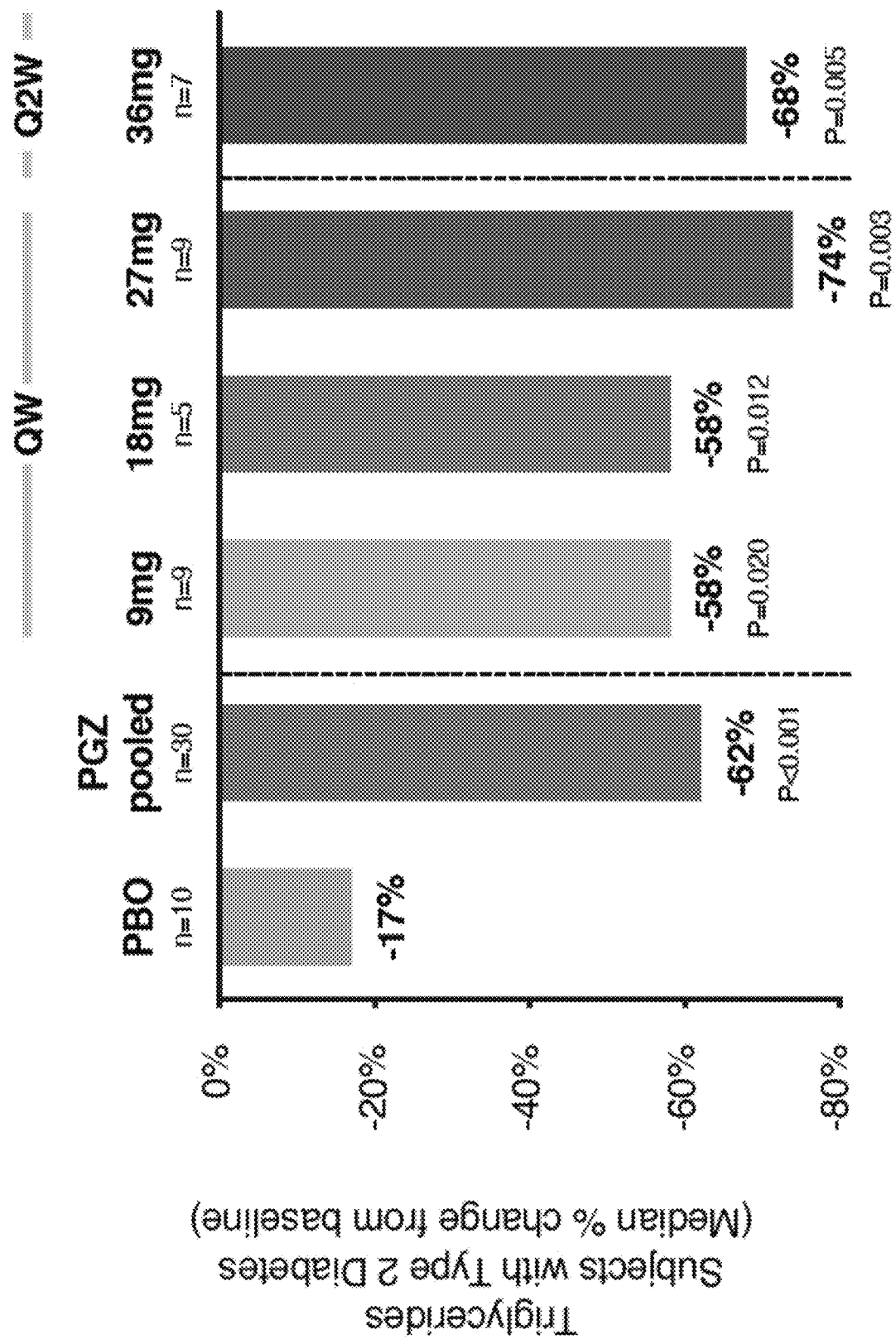

Pegozafermin significantly reduced TG after 8 weeks of therapy across all dose groups, with placebo-corrected changes from baseline ranging from −29.0% to −52.9%. Pooled pegozafermin data showed a placebo-corrected median percent change in TG levels of −43.7% (−57.3% vs. −11.9% placebo; 95% CI−57.1%, −30.3%; p<0.001) (FIG. 16A). A total of 79.7% of patients treated with pegozafermin achieved a target TG level of <500 mg/dL, compared with 29.4% of patients on placebo (52.1% placebo-corrected, 95% CI: 29.4%, 74.7%; p<0.001) (FIG. 16B). Furthermore, 60.9% of all patients treated with pegozafermin had reductions of ≥50% from baseline, compared with 5.9% of patients on placebo (53.1% placebo-corrected, 95% CI: 36.7%, 69.5%; p<0.001), while at the highest QW dose (27 mg), 75.0% of patients saw a TG reduction of ≥50% from baseline (69.1% placebo-corrected, 95% CI: 45.1%, 93.1%; p<0.001) and 31.3% were able to normalize their TG to <150 mg/dL compared with 0% in the placebo patients (31.3% placebo-corrected, 95% CI: 8.5%, 54.0%; p=0.012) (FIG. 16B). TG reduction was comparable across all prespecified groups (FIG. 6B) and remained consistent irrespective of background lipid-lowering therapy or T2DM status (FIGS. 16C-16F).

Effects on Overall Lipid Profile

Figure 17A:
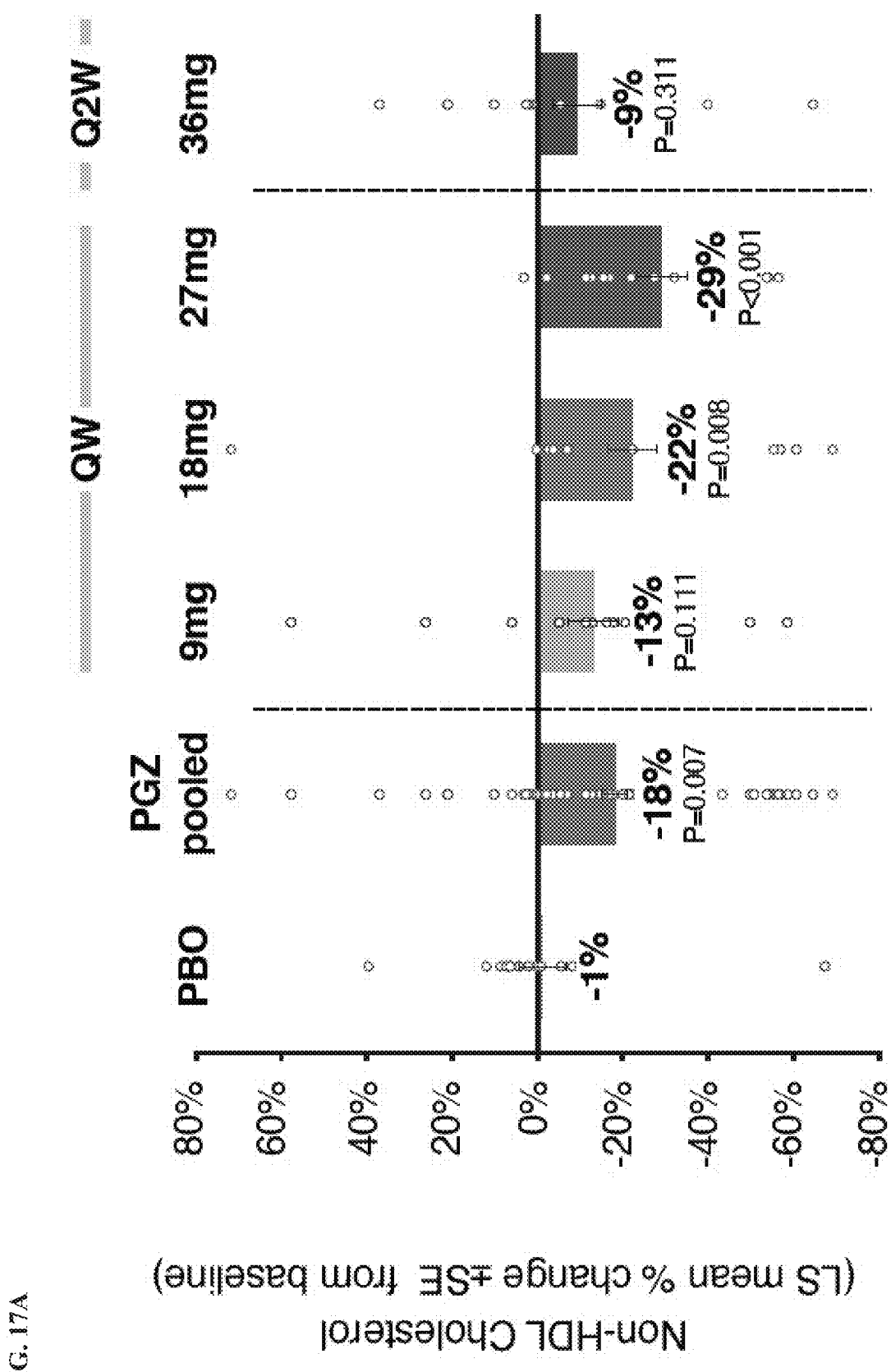
FIGS. 17A-17E are graphs showing the effect of pegozafermin on serum lipids. Least square (LS) mean (+/−SE) or median (apoC3) percent change in non-HDL-C (FIG. 17A), apolipoprotein B (FIG. 17B), apolipoprotein C3 (FIG. 17C), LDL cholesterol (FIG. 17D), and HDL cholesterol (FIG. 17E) from baseline to week 8. Data are based on full analysis set population (defined as all randomized subjects who received at least one dose of study treatment, had baseline and at least one post-baseline TG) and analyzed via MMRM. N represents independent subjects examine at baseline and 2 post-baseline timepoints for lipid related graphs. All p-values are two sided and based on comparison to the placebo arm.QW, once-weekly; Q2W, once-every two weeks; PBO, placebo; PGZ, pegozafermin.
Figure 17B:
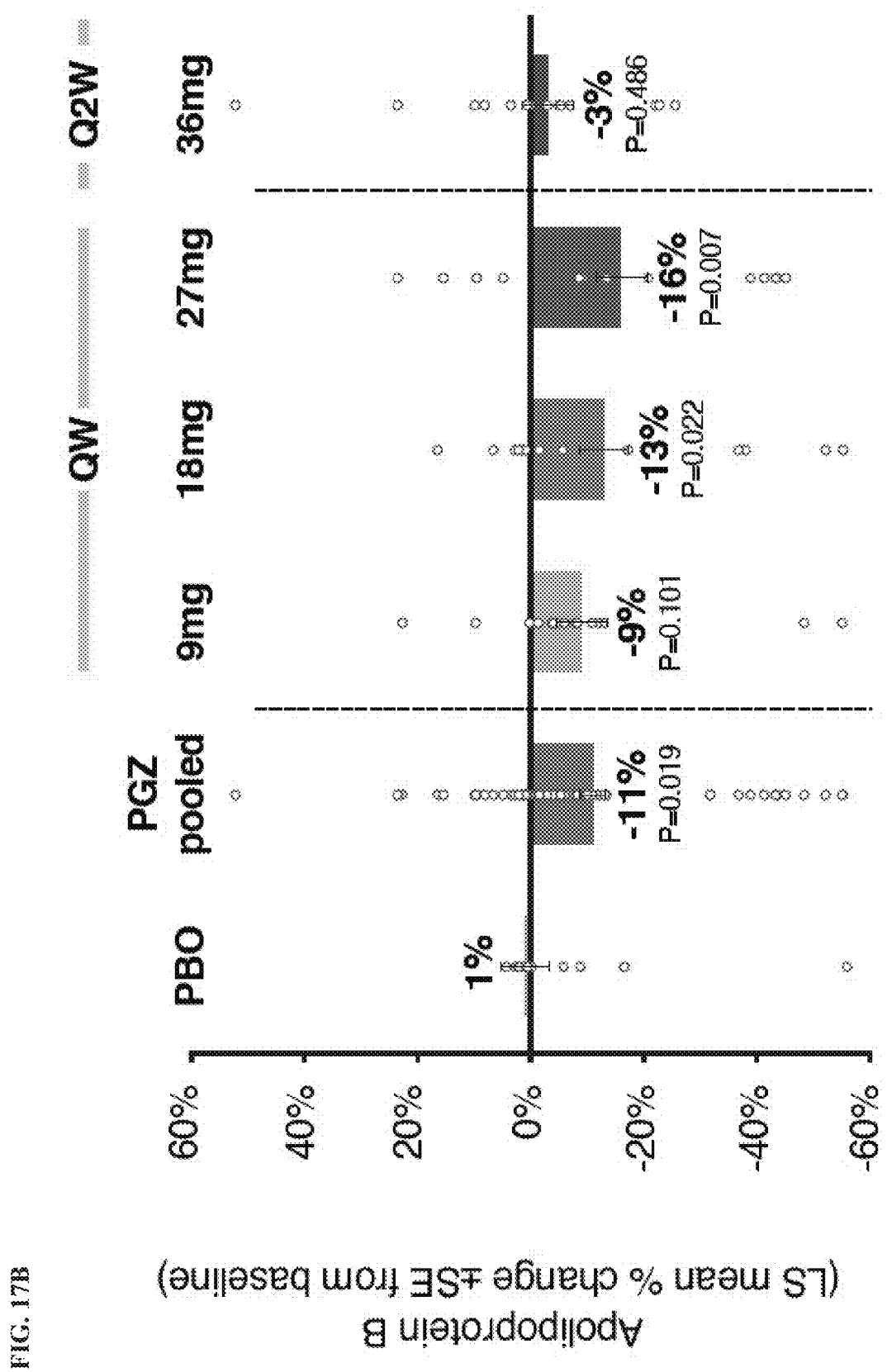
Figure 17C:
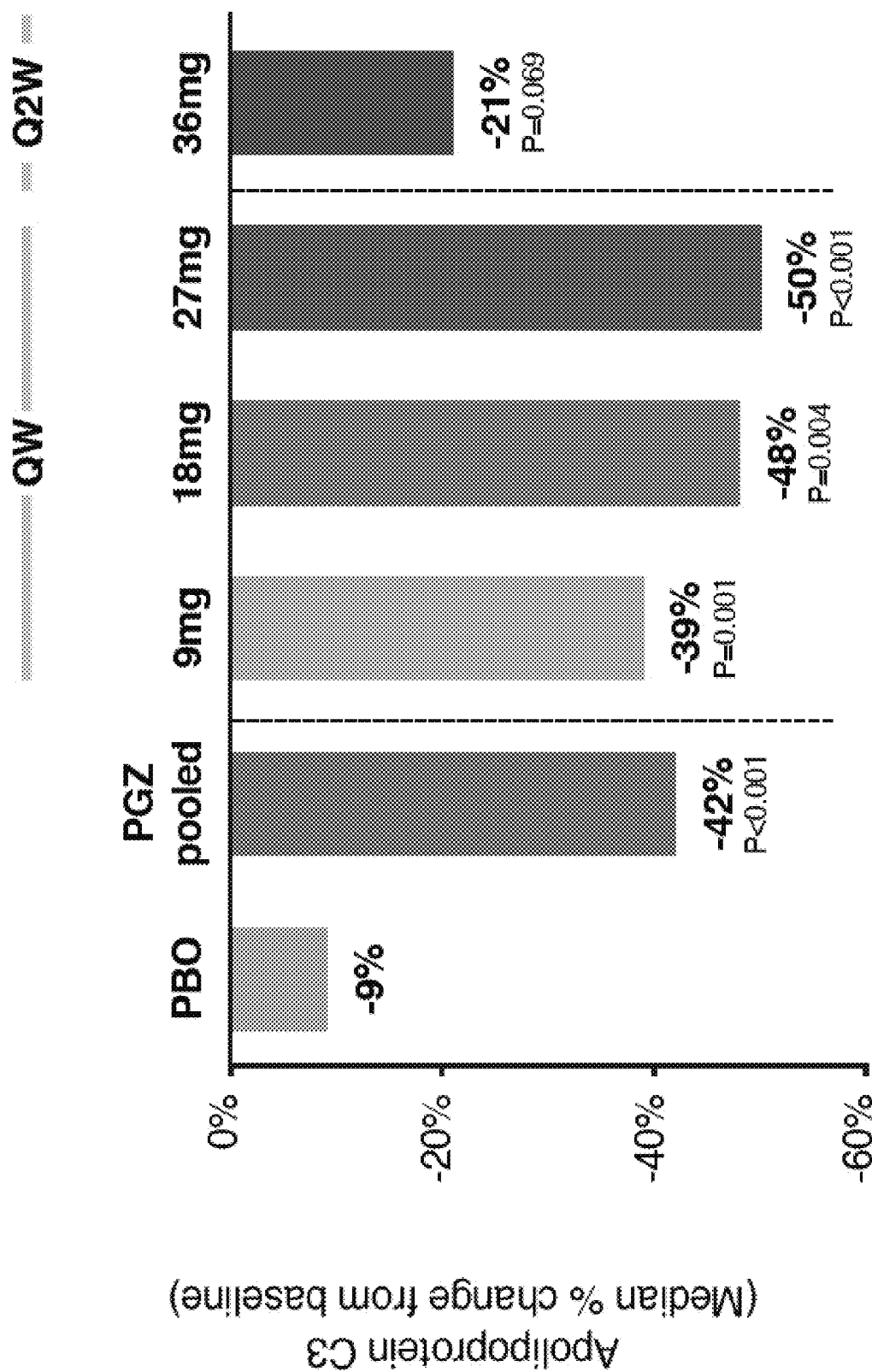
Figure 17D:
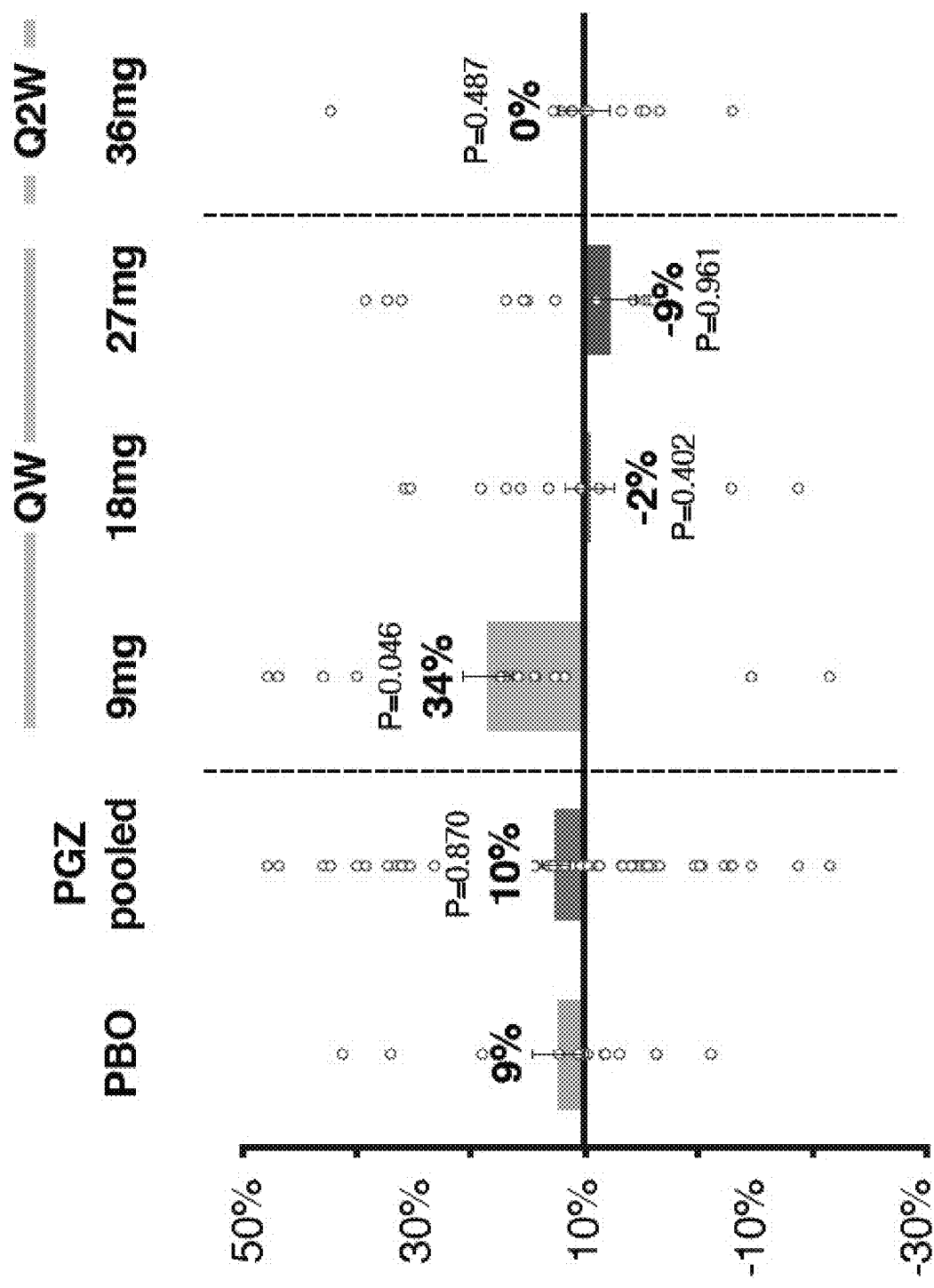
Figure 17E:
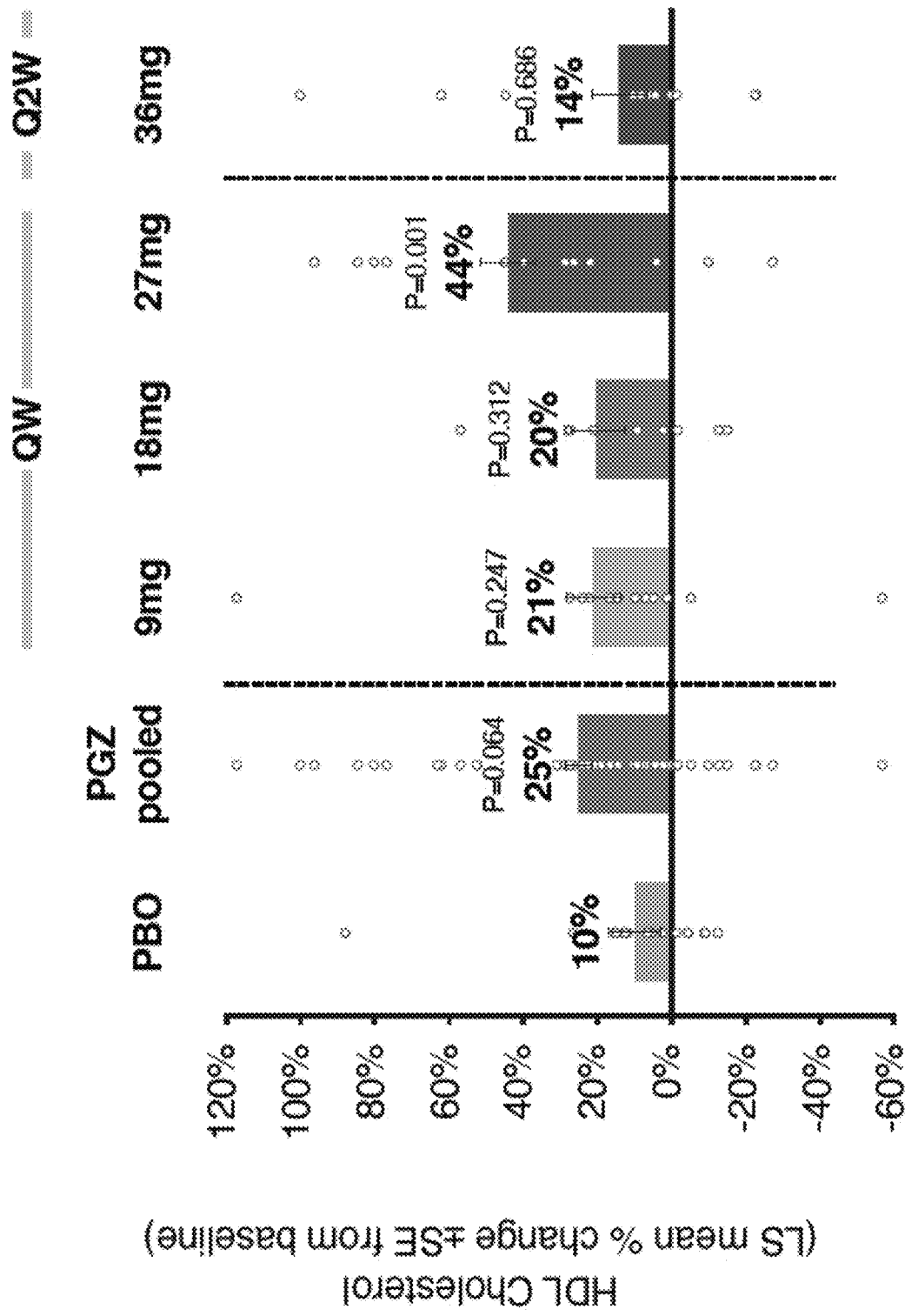

Treatment with pegozafermin resulted in improvements in non-HDL-C and apolipoprotein B (ApoB), with Least Squares (LS) mean percent changes from baseline for pooled pegozafermin of −18.3% versus −0.6% for placebo (−17.9% placebo-corrected, 95% CI: −30.7%, −5.1%; p=0.007) and −10.5% versus 1.1% for placebo (−11.8% placebo-corrected, 95% CI: −21.5%,—2.0%; p=0.019), respectively (FIGS. 17A-17B). Treatment with pegozafermin also led to a significant reduction in ApoC3 (median percent change −41.9% vs. −8.9% placebo [−32.0% placebo-corrected, 95% CI: −44.7%, −18.0%; p<0.001]) (FIG. 17C). Although minimal changes in LDL-C were detected in pooled pegozafermin (FIG. 17D), LS mean percent change in HDL-C levels from baseline in pegozafermin subjects receiving the 27 mg weekly dose significantly increased (44.5% vs. 9.7% for placebo [34.8% placebo-corrected, 95% CI: 14.5%, 55.1%; p=0.001]) (FIG. 17E). Treatment with pegozafermin 27 mg weekly also resulted in a 73% decrease in ApoB48, suggesting improved clearance of plasma chylomicrons and their remnants, in addition to reductions in ApoB100 particles. Additional lipid data are shown below.

TABLE 7

| | Placebo (n = 17) | PGZ Pooled (n = 65) | PGZ 9 mg QW (n = 16) | PGZ 18 mg QW (n = 17) | PGZ 27 mg QW (n = 16) | PGZ 36 mg Q2W (n = 16) |
|---|---|---|---|---|---|---|
| Total cholesterol | | | | | | |
| Mean baseline (mg/dL) | 247.04 | 237.47 | 246.89 | 230.46 | 232.84 | 240.13 |
| Mean week 8 (mg/dL) | 235.53 | 199.84 | 211.25 | 184.13 | 186.87 | 216.31 |
| % Mean change from baseline | −2.10 | −13.43 | −10.43 | −17.21 | −19.66 | −6.83 |
| LDL particle size | | | | | | |
| Mean baseline (nm) | 19.79 | 19.79 | 19.87 | 19.69 | 19.86 | 19.73 |
| Mean week 8 (nm) | 19.59 | 20.06 | 20.07 | 19.79 | 20.55 | 19.81 |
| % Mean change from baseline | −1.18 | 1.40 | 1.27 | 0.45 | 3.52 | 0.40 |
| LDL particle number | | | | | | |
| Mean baseline (nmol/L) | 1533.16 | 1653.29 | 1656.31 | 1675.73 | 1789.67 | 1501.38 |
| Mean week 8 (nmol/L) | 1515.94 | 1605.57 | 1650.73 | 1522.87 | 1764.13 | 1492.13 |
| % Mean change from baseline | 5.49 | 4.54 | 13.04 | −8.40 | 1.38 | 9.83 |
| TRL-C | | | | | | |
| Mean baseline (mg/dL) | 109.0 | 104.2 | 101.7 | 109.2 | 95.5 | 109.6 |
| Mean week 8 (mg/dL) | 107.1 | 67.7 | 63.0 | 61.8 | 47.5 | 96.8 |
| % Mean change from baseline | 7.1 | −29.2 | −38.2 | −31.6 | −45.3 | −6.4 |
| VLDL cholesterol | | | | | | |
| Median baseline (mg/dL) | 107.25 | 96.0 | 103.50 | 96.0 | 93.75 | 100.75 |
| Median week 8 (mg/dL) | 97.0 | 54.0 | 54.00 | 45.0 | 34.0 | 87.0 |
| % Median change from baseline | −0.41 | −47.96 | −47.86 | −57.40 | −57.98 | −16.67 |
| VLDL triglycerides | | | | | | |
| Median baseline (mg/dL) | 433.25 | 538.0 | 514.0 | 514.5 | 581.0 | 556.75 |
| Median week 8 (mg/dL) | 424.5 | 219.0 | 204.50 | 191.50 | 156.0 | 486.50 |
| % Median change from baseline | −0.85 | −58.50 | −60.35 | −63.51 | −67.83 | −26.03 |
| Lipoprotein (a) | | | | | | |
| Median baseline (nmol/L) | 19.50 | 12.50 | 13.75 | 7.0 | 12.33 | 28.50 |
| Median week 8 (nmol/L) | 14.0 | 17.0 | 20.0 | 9.0 | 23.0 | 42.0 |
| % Median change from baseline | −1.09 | 39.49 | 50.21 | 23.44 | 27.87 | 43.17 |
| Apoliporotein B48 | | | | | | |
| Median baseline (mg/dL) | 2.60 | 3.76 | 3.02 | 4.07 | 4.90 | 3.61 |
| Median week 8 (mg/dL) | 2.05 | 1.69 | 1.63 | 1.79 | 1.36 | 2.85 |
| % Median change from baseline | −6.57 | −58.20 | −57.85 | −65.43 | −72.52 | −10.62 |
| Free fatty acids | | | | | | |
| Median baseline (mmol/L) | 0.58 | 0.55 | 0.46 | 0.55 | 0.57 | 0.56 |
| Median week 8 (mmol/L) | 0.51 | 0.54 | 0.63 | 0.56 | 0.49 | 0.54 |
| % Median change from baseline | −17.45 | −3.97 | 12.93 | −5.43 | −8.83 | −2.87 |

LDL, low-density lipoprotein;
PGZ, pegozafermin;
QW, once-weekly;
Q2W, once every 2 weeks;
VLDL, very-low-density lipoprotein.

Hepatic and Metabolic Effects

Figure 18A:
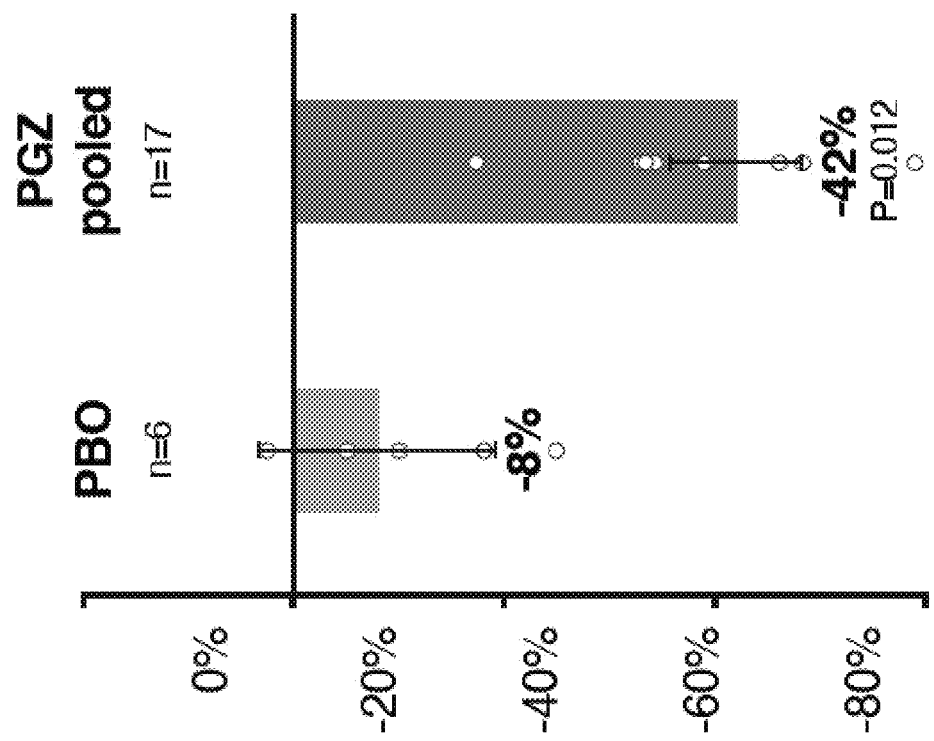
FIGS. 18A-18C show the effect of pegozafermin on hepatic steatosis.
Figure 18B:
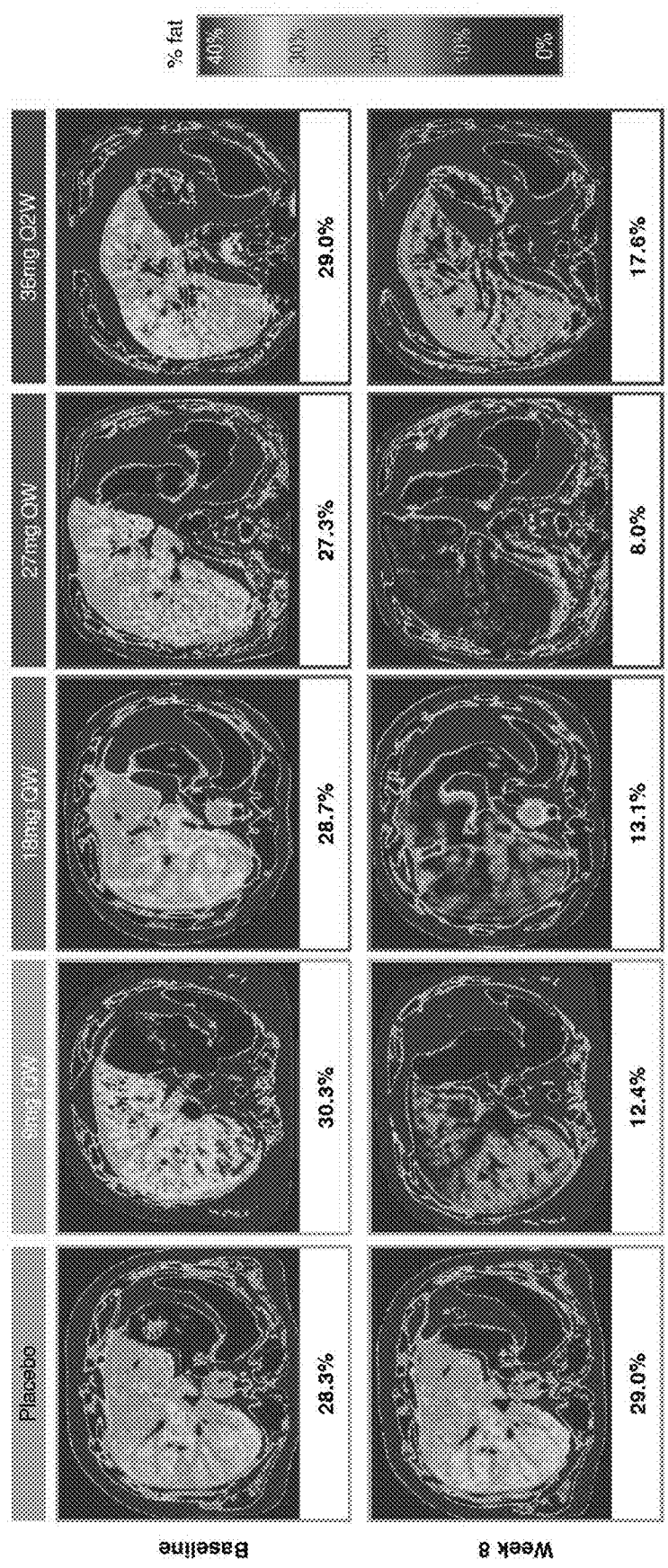
Figure 18C:
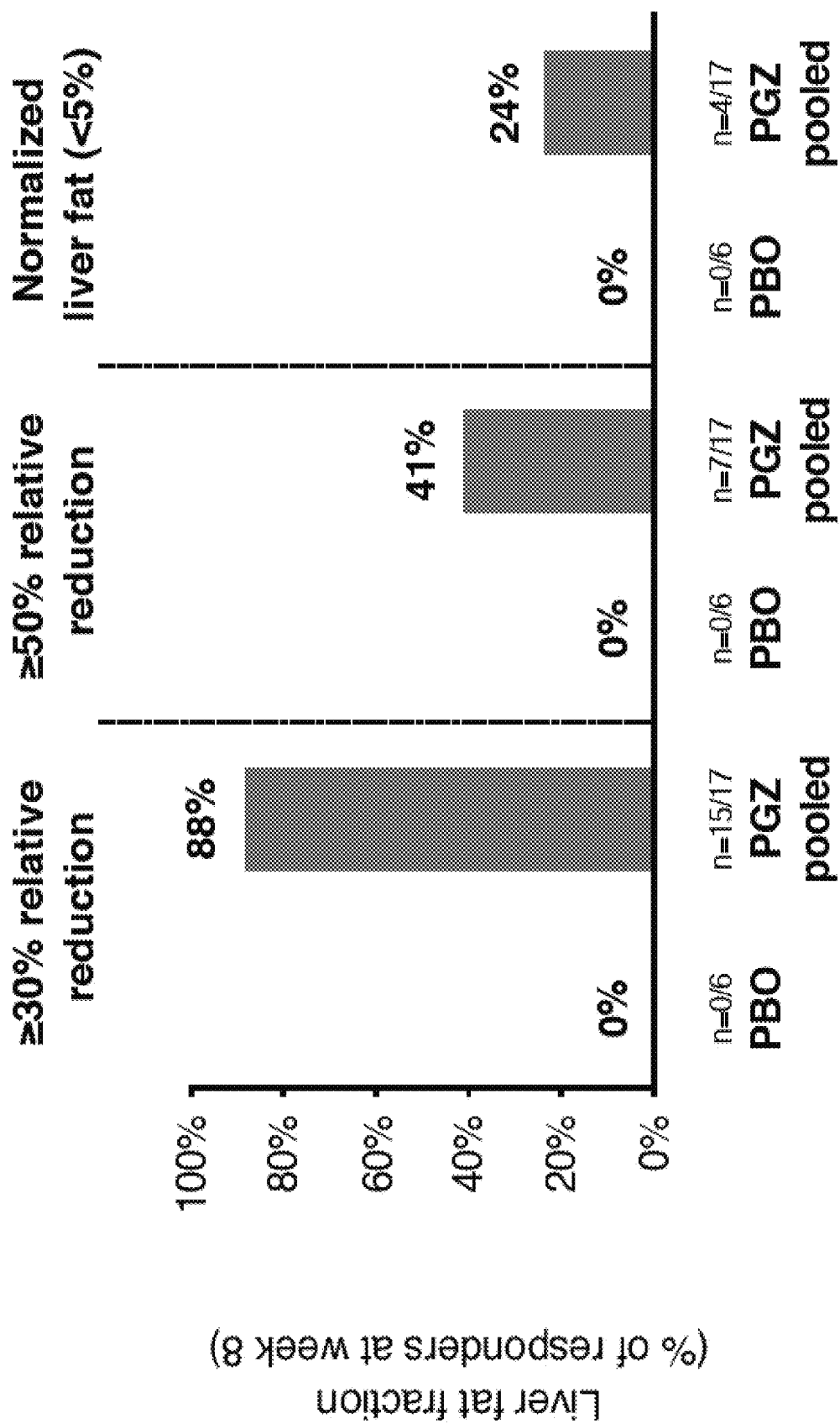
Figure 19:
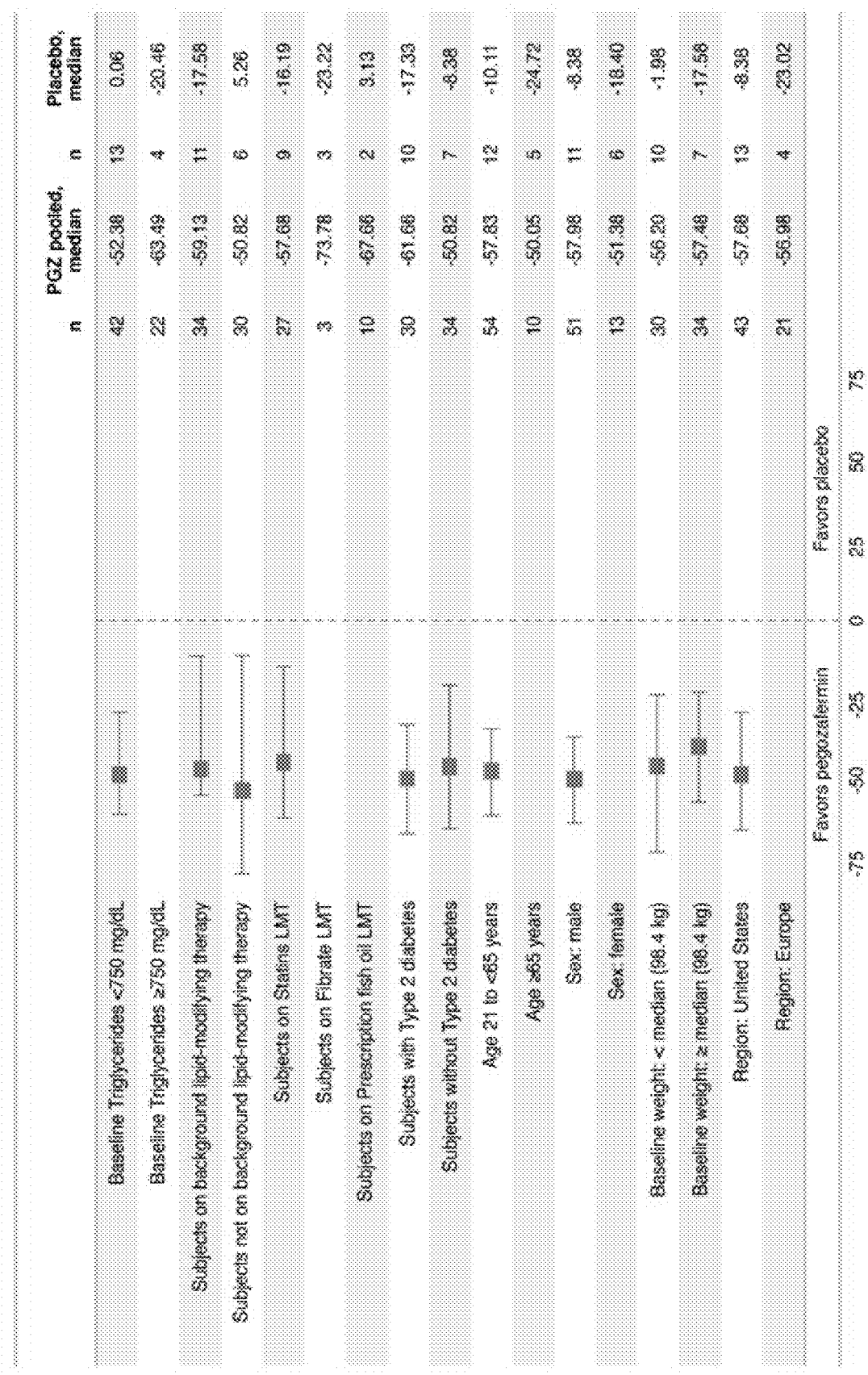
FIG. 19 is a graph showing that triglycerides reduction was comparable across all prespecified groups.

Patients treated with pegozafermin for 8 weeks had significant reductions in liver steatosis compared with placebo (LS mean percent change −42.2% vs. −8.3%; 95% CI: −60.9%, −8.7%; p=0.012) (FIG. 18A). Representative MRI-PDFF images are shown in FIG. 18B, with all individual treatment images and responses presented in FIG. 6A and FIG. 6B. Many patients treated with pegozafermin attained important clinical thresholds, including ≥30% reduction, ≥50% reduction or normalization of liver fat (defined as <5%), with response rates of 88%, 41% and 24%, respectively, compared with 0% in placebo across all measurements (FIG. 18C). Patients receiving the 27 mg weekly dose also saw improvement in the inflammatory markers: alanine aminotransferase, aspartate aminotransferase and high-sensitivity C-reactive protein (see table below).

TABLE 8

|  | Placebo (n = 17) | PGZ Pooled (n = 65) | PGZ 9 mg QW (n = 16) | PGZ 18 mg QW (n = 17) | PGZ 27 mg QW (n = 16) | PGZ 36 mg Q2W (n = 16) |
| --- | --- | --- | --- | --- | --- | --- |
| AST |  |  |  |  |  |  |
| Mean baseline, mg/dL | 23.71 | 24.80 | 26.69 | 27.65 | 24.06 | 20.63 |
| Mean week 8, mg/dL | 23.65 | 19.65 | 20.06 | 19.25 | 20.53 | 18.81 |
| % Mean change from baseline | 1.45 | −11.10 | −12.62 | −11.16 | −15.94 | −4.99 |
| ALT |  |  |  |  |  |  |
| Mean baseline, mg/dL | 28.35 | 33.66 | 36.25 | 36.94 | 32.06 | 29.19 |
| Mean week 8, mg/dL | 28.71 | 28.98 | 29.81 | 32.81 | 24.60 | 28.44 |
| % Mean change from baseline | 2.56 | −4.78 | −4.66 | −1.86 | −17.62 | 4.22 |
| hsCRP |  |  |  |  |  |  |
| Median baseline, mg/dL | 4.30 | 2.40 | 3.15 | 1.40 | 2.50 | 2.80 |
| Median week 8, mg/dL | 3.60 | 2.10 | 3.05 | 1.70 | 1.70 | 1.90 |
| % Median change from baseline | −1.10 | −21.43 | 0.00 | 15.62 | −37.04 | −28.21 |

ALT, alanine aminotransferase;
AST, aspartate aminotransferase,
hsCRP, high-sensitivity C-reactive protein;
PGZ, pegozafermin;
QW, once-weekly;
Q2W, once every 2 weeks Safety Treatment emergent adverse events (TEAEs) were reported in 41/67 (61.2%) of patients treated with pegozafermin versus 9/18 (50%) on placebo (See Table below).

TABLE 9

| Safety. | | | | | | |
| --- | --- | --- | --- | --- | --- | --- |
|  | Placebo (n = 18) | PGZ Pooled (n = 67) | PGZ 9 mg QW (n = 12) | PGZ 18 mg QW (n = 21) | PGZ 27 mg QW (n = 18) | PGZ 36 mg Q2W (n = 16) |
| Treatment-emergent adverse events (TEAEs) | 9 (50.0) | 41 (61.2) | 7 (58.3) | 13 (61.9) | 14 (77.8) | 7 (43.8) |
| Grade 1 (Mild) | 5 (27.8) | 22 (32.8) | 6 (50.0) | 7 (33.3) | 6 (33.3) | 3 (18.8) |
| Grade 2 (Moderate) | 4 (22.2) | 19 (28.4) | 1 (8.3) | 6 (28.6) | 8 (44.4) | 4 (25.0) |
| Grade >3 (Severe) | 0 | 0 | 0 | 0 | 0 | 0 |
| Serious TEAEs | 0 | 1 (1.5) | 0 | 0 | 1 (5.6) | 0 |
| Hypertension | 0 | 1 (1.5) | 0 | 0 | 1 (5.6) | 0 |
| TEAEs related to treatment | 2 (11.1) | 23 (34.3) | 5 (41.7) | 6 (28.6) | 7 (38.9) | 5 (31.3) |
| Serious TEAEs related to treatment | 0 | 0 | 0 | 0 | 0 | 0 |
| TEAEs leading to treatment discontinuation | 0 | 4 (6.0).3 | 0 | 0 | 4 (22.2) | 0 |
| Hypertension | 0 | 1 (1.5) | 0 | 0 | 1 (5.6) | 0 |
| Abdominal pain | 0 | 2 (3.0) | 0 | 0 | 2 (11.1) | 0 |
| Nausea | 0 | 2 (3.0) | 0 | 0 | 2 (11.1) | 0 |

TABLE 9-continued

Safety.

|  | Placebo (n = 18) | PGZ Pooled (n = 67) | PGZ 9 mg QW (n = 12) | PGZ 18 mg QW (n = 21) | PGZ 27 mg QW (n = 18) | PGZ 36 mg Q2W (n = 16) |
|---|---|---|---|---|---|---|
| Vomiting | 0 | 1 (1.5) | 0 | 0 | 1 (5.6) | 0 |
| TEAEs reported by ≥5% in pooled PGZ groups |  |  |  |  |  |  |
| Nausea | 0 | 9 (13.4) | 1 (8.3) | 1 (4.8) | 5 (27.8) | 2 (12.5) |
| Diarrhea | 1 (5.6) | 7 (10.4) | 2 (16.7) | 1 (4.8) | 4 (22.2) | 0 |
| Injection site reaction | 0 | 6 (9.0) | 1 (8.3) | 2 (9.5) | 1 (5.6) | 2 (12.5) |
| COVID-19 | 3 (16.7) | 4 (6.0) | 0 | 3 (14.3) | 0 | 1 (6.3) |
| Injection site erythema | 0 | 4 (6.0) | 0 | 1 (4.8) | 2 (11.1) | 1 (6.3) |
| Injection site pruritus | 0 | 4 (6.0) | 1 (8.3) | 2 (9.5) | 1 (5.6) | 0 |
| Abdominal pain | 0 | 3 (4.5) | 0 | 0 | 2 (11.1) | 1 (6.3) |

COVID-19, Coronavirus Disease-19;
PGZ, pegozafermin;
TEAE, treatment-emergent adverse event. Safety Analysis Set is defined as all subjects who received at least 1 dose of investigational product. Safety Analysis Set is summarized based on planned treatment. 4 subjects randomized to receive 9 mg QW received 18 mg QW throughout the treatment; these 4 subjects were categorized in planned treatment group of 9 mg QW. Three subjects randomized to receive 27 mg QW received 36 mg QW throughout the treatment; these 3 subjects were categorized in the planned treatment group of 27 mg QW.

The most common TEAEs were related to gastrointestinal disturbances and injection site reactions, all of which were mild to moderate, with the majority transient in duration. In the pooled pegozafermin group, nausea, diarrhea and injection site reactions occurred at rates of 13.4%, 10.4%, and 9%, respectively, compared with 0%, 5.6%, and 0% for placebo. The percent of TEAEs was higher for nausea (27.8%) and diarrhea (22.2%) in the 27 mg weekly dose. No Grade 3 or higher TEAEs were reported. There was no difference in clinically significant shifts for blood pressure between placebo and pegozafermin treatment groups at week 8. Mean change in systolic pressure for placebo and pegozafermin was −4.1 mmHg and 0.7 mmHg at week 4 and 0.3 mmHg and 1.7 mmHg at week 8, respectively. However, one serious TEAE of hypertension was reported in the 27 mg QW arm in a patient with newly diagnosed hypertension prior to enrollment, which was deemed unrelated to treatment and led to study discontinuation. There were three additional treatment emergent discontinuations in the 27 mg arm: two patients with TEAEs considered related by the investigator (one with nausea and vomiting and one with abdominal cramps) and one patient with nausea and abdominal pain assessed as unrelated to pegozafermin. No deaths, systemic hypersensitivity reactions, or adverse events of liver transaminase elevation were reported.

Discussion

This placebo-controlled, randomized study demonstrated that treatment with the FGF21 analog pegozafermin resulted in significant reductions in TGs in patients with SHTG. Significant reductions were also observed in atherogenic lipoproteins, including non-HDL-C and ApoB, as well as ApoC3, an important regulator of lipoprotein lipase, suggesting pegozafermin reduces production and improves clearance of TG-rich lipoproteins. Whereas levels of LDL-C remained relatively stable, there was a numerical increase in HDL cholesterol across all doses, most notably at the 27-mg dose; the 27-mg dose was also the most efficacious for reducing TGs and lipoproteins. Every-other-week dosing had less impact across the various outcome parameters, likely due to the pharmacokinetics of the drug and volatility of TG levels.

Eligibility criteria allowed for enrolment of subjects on stabilized regimens of approved lipid-modifying therapies (LMT), such as statins, prescription fish oil and/or fibrates. Approximately 55% of subjects enrolled on background LMT, with a majority on a statin (45% [25% high-intensity statin]), followed by prescription fish oil (14%) and fibrates (7%). Initially, fibrates had been excluded due to potential crosstalk between FGF21 and peroxisome proliferator-activated receptor alpha (PPARα) pathways[30], but the study was ultimately amended to include a fibrate cohort, with the additional criteria that those subjects must have had at least 6% liver fat at baseline. Enrolment into this arm proved difficult (n=6) and, therefore, subjects on fibrates were likely underrepresented in the final study population relative to clinical practice. Nonetheless, with the exception of this potential caveat regarding fibrates, overall utilization of LMTs in the study population appeared to generally reflect real-world treatment patterns in patients with SHTG. Christian et al. reported that baseline medication use (up to 6 months preceding the index date) was approximately 31% for statins and 14% for triglyceride-lowering medications[31]. In the same study, follow-up medication use after the index date slightly increased to 38% and 35%, for statins and TG-lowering medications, respectively, leaving a substantial number of patients still left untreated. Similarly, a study by Toth et al. reported that 30-50% of TG-treatment-naïve patients had not initiated any pharmacotherapy within 4 months of their index date (of those who were prescribed medication, approximately 50% received a statin, 30% received fibrates and 8% received omega-3 fatty acids)[32]. More recently, data from the Rochester Epidemiology Project showed that only 46% of patients with primary isolated hypertriglyceridemia (TG≥500 mg/dL) were on LMTs within 18 months after detection of elevated TG levels[33].

In the current study, it should be noted that the effect of pegozafermin remained consistent regardless of the presence or absence of background LMT, suggesting that pegozafermin can significantly improve many important lipid parameters when used as an adjunct to diet and exercise or as add-on therapy in patients who are unable to achieve TG<500 mg/dL. Furthermore, the effect of pegozafermin was comparable irrespective of LMT drug classification. This is an important finding, as data in patients with residual dyslipidemia on LMT in the United States showed only 36.5% of such patients were at goal or near normal levels for TG, LDL-C and HDL-C[34].

While the primary target for CV risk reduction remains LDL-C, identifying new therapies that can address residual CV risk after LDL treatment is of significant interest. Most clinical trials utilizing therapies that lower triglycerides (i.e., fibrates, niacin and omega-3 fatty acids, with the exception of icosapent ethyl) have not demonstrated an add-on reduction in CV events in patients on statin therapy[4]. For instance, while the REDUCE-IT trial (icosapent ethyl [IPE] 4 g/day) did find a 25% reduction (p<0.001) in a composite of CV events in high-risk patients, only part of the benefit was predicted by TG lowering, suggesting the outcomes were attributable to broader pleiotropic effects of IPE. The PROMINENT trial found no benefit on CV outcomes, despite TG reductions with pemafibrate[35]. The aforementioned trials were conducted in patients with TG<500 mg/dL, so extrapolation to an SHTG population requires caution. PROMINENT reported that pemafibrate demonstrated a modest decrease in TG (−26.2%) and VLDL-C (−25.8%), but led to placebo-corrected increases in LDL-C, ApoB, and non-HDL-C (10 mg/dL, 5 mg/dL and 3 mg/dL, respectively) with no differences in CV outcomes[35]. Similar to pemafibrate, an increase in LDL-C was also observed in the recently published paper on evinacumab (an angiopoietin-like 3 inhibitor [ANGPTL3]) in patients with SHTG across 3 cohorts with and without lipoprotein lipase pathway mutations, though it should be noted both non-HDL-C and ApoB were decreased in this study[36]. It is not unexpected that LDL-C may increase, sometimes dramatically, in patients being treated for SHTG, particularly with agents as fenofibrate or EPA/DHA. This is known as the 'beta-shift' phenomenon, where LDL-C levels can rise due to increased lipolysis of VLDL via lipoprotein lipase[37]. In the current study, there was a relatively small increase in LDL-C that did not differ from placebo, however one might speculate that the 45% of patients receiving background statin therapy could have impacted the observed LDL-C response. Indeed, a post-hoc analysis of patients on background lipid-modifying therapy (which included but was not limited to statin therapy) demonstrated a placebo-corrected LS mean difference in LDL-C of −9.0%, compared to a LS mean difference of 1.7% for pooled pegozafermin groups[38]. Patients enrolled in this study had a mean baseline LDL-C of <90 mg/dL, which is relatively well-controlled for this population, so any impact related to the minimal change in LDL-C is likely to be offset by the significant decreases in both non-HDL-C, ApoB and meaningful reductions in triglyceride rich lipoprotein cholesterol [TRL-C] when considering the overall atherogenic burden.

Newer RNA-based therapies (antisense oligonucleotide [ASO] and RNA interference [RNAi]) also are being developed to significantly lower TG in both familial chylomicronemia syndrome (FCS) and severe hypertriglyceridemia. Early data suggest that traditional ASO approaches may be associated with safety concerns. For example, while volanesorsen (ASO APOC3 inhibitor) is approved in the EU for the treatment of FCS[39], it has not gained FDA approval because of concerns regarding bleeding and thrombocytopenia. Additionally, Pfizer and Ionis discontinued their vupanorsen clinical program (ASO targeting ANGPTL3) because of modest effects on non-HDL-C and TG reduction and association with dose-dependent increases in liver fat and liver enzymes[40]. Development of second-generation ASOs, such as olezarsen [APOC3 inhibitor], has been a major advancement, which is reflected in its FDA fast track designation for patients with FCS. siRNA agents also appear promising, although some safety signals appear to be associated with these agents, as well. Data from the SHASTA-2 trial evaluating ARO-APOC3 for SHTG suggest this agent may be associated with increases in LDL-C, although data from the ARCHES-2 trial for mixed dyslipidemia evaluating ARO-ANGPTL3 demonstrated a reduction in LDL-C[41,42]. Whether the differential effects on LDL-C are related to the disparate baseline triglyceride levels in the two populations or dependent on the difference in gene targets remains unclear. Interestingly, both trials reported increased HbA1c in the treatment arm, particularly in patients with baseline diabetes.

In the 8-week study reported here, pegozafermin significantly reduced TG, non-HDL-C, ApoB and liver fat, increased HDL-C with minimal change in LDL-C, and improved liver transaminases, all while maintaining a favorable safety and tolerability profile. Taken together, these data suggest that pegozafermin provides an overall metabolic benefit with, as yet, no identified safety signals.

While patients with SHTG have elevated risk for CV events, the primary clinical risk in patients with TG≥500 mg/dL is acute pancreatitis, owing to saturation of, or impairment in, lipoprotein lipase-mediated lipolysis. The consequence is accumulation of TG-rich particles that are hydrolyzed by pancreatic lipase, release of free fatty acids, and subsequent proinflammatory signaling in adjacent pancreatic tissues[43]. Preclinical data suggest that FGF21 may have a role in modulating the inflammation and damage induced by experimental pancreatitis[44]. Furthermore, FGF21 has been postulated to promote β-cell survival and to protect isolated rat islets and insulin-producing INS cells from glucolipotoxicity and cytokine-induced apoptosis[44].

Valdivielso et al. demonstrated that elevated levels of chylomicrons are necessary to trigger acute pancreatitis in the setting of high serum triglycerides[45]. Subjects in the current study had markedly elevated ApoB48, a specific marker of chylomicron particles, at baseline (median range 2.60-4.90 mg/dL) compared with healthy subjects (median 0.51 mg/dL), hyperlipidemic subjects (median 0.7 mg/dL) and subjects with obesity (median 0.82 mg/dL), putting them at an increased risk for developing acute pancreatitis[46]. Pegozafermin reduced ApoB48 robustly (73% reduction for the 27-mg weekly dose), suggesting an ability to improve clearance of chylomicrons and chylomicron remnants. Taskinen et al. recently demonstrated that patients with loss-of-function mutations in APOC3, which increases lipoprotein lipase activity, had lower plasma concentrations of VLDL, IDL and ApoB48 particles[47]. CM-ApoB48 and VLDL ApoB100 production rates were not affected, indicating that enhanced remnant removal may be the predominant mechanism for the observed reduction.

Pegozafermin demonstrated a robust 50% reduction of ApoC3 at the 27-mg dose, suggesting that increased lipoprotein lipase activity may contribute to the observed ApoB48 reduction. Indeed, post hoc analyses assessing the correlation between percent change in TG and ApoC3 in the pooled pegozafermin group at week 8 demonstrated a reasonable correlation between the two [Pearson r (linear correlation)=0.87; Spearman r=0.80, with p-value <0.001], which indicates that greater reductions in TG were accompanied by greater reductions in ApoC3

Current guidelines from the National Cholesterol Education Program Adult Treatment Panel III recommend reducing TGs to <500 mg/dL to prevent acute pancreatitis, with a secondary focus on decreasing CV risk. Data from a large retrospective claims study have demonstrated a lower incidence of clinical events for patients with SHTG who had follow-up TG levels <400 mg/dL, with significant incidence rate ratios in patients with follow-up TGs<300 mg/dL for pancreatitis, overall CV events, acute myocardial infarction (AMI), heart failure (HF), revascularization and acute coronary syndrome. However, the greatest clinical benefit (overall more robust incidence rate ratios and additional significance in ischemic stroke) was seen when follow-up levels were driven below 200 mg/dL[31]. In the current study, 80% of patients receiving pegozafermin (pooled data) were able to drive their TG below 500 mg/dL, with 44% and 31% of subjects receiving the 27-mg weekly dose achieving TG levels <200 mg/dL and <150 mg/dL, respectively, suggesting that pegozafermin may favorably impact the risk of acute pancreatitis and CV events.

SHTG patients often have metabolic comorbidities associated with dyslipidemia and insulin resistance, such as obesity, metabolic syndrome, T2DM and non-alcoholic fatty liver disease, further increasing the risk of cardiovascular morbidity and mortality. Dramatic increases in obesity and T2DM over the past decades have exacerbated the development of NAFLD, making it a rising health concern in the US and globally. NAFLD is currently the most common form of chronic liver disease in the U.S and is often considered the hepatic manifestation of the metabolic syndrome, a patient population that frequently suffers from atherogenic dyslipidemia. An important finding of the present study was the prevalence of liver fat in this SHTG population: 100% of patients who underwent MRI-PDFF screening had baseline hepatic steatosis, as defined by >5% liver fat (range 6.2-39.2%). Interestingly baseline MRI-PDFF values did not correlate with baseline TG values, although every patient tested who had a baseline fasting TG level >500 mg/dL had greater than 5% hepatic steatosis.

Pegozafermin therapy demonstrated significant reductions in fat accumulation in the liver, hitting key reduction targets of ≥30% and ≥50% in 88% and 41% of subjects, respectively. These are important thresholds as it has been established in the literature that a ≥30% relative reduction in MRI-PDFF is associated with histologic response (categorized as a responder) and that a ≥50% relative reduction in MRI-PDFF evokes a significantly higher histologic response (defined as super responder)[48]. In addition to the strong association of hepatic steatosis and histology, the presence of fatty liver has also been associated with more severe acute pancreatitis which can lead to a higher incidence of local complications, persistent organ failure and mortality regardless of underlying etiology[49,50]. More recently Wu et al reported that hyperlipidemia pancreatitis had the highest incidence of NAFLD (65%) and that the severity of AP, incidence of systemic inflammatory response syndrome and organ failure was higher in patients with NAFLD versus a non-NAFLD group[51].

Pegozafermin treatment was able to normalize liver fat to ≤5% in 24% of subjects in just 8 weeks. To our knowledge, these are the first data to report a significant reduction in quantified liver fat with a treatment targeting TG-rich lipoproteins in SHTG and suggest a potential benefit for lowering the risk of severe acute pancreatitis. The mechanism by which pegozafermin lowers liver fat remains to be fully characterized. Based on preclinical data in hepatocytes, FGF21 is thought to affect hepatic steatosis by modulating AMPK phosphorylation to regulate lipid accumulation, reducing sterol regulatory element-binding transcription factor 1 (SREBF1) to inhibit lipid synthesis, increasing PPARα mRNA and PPARα translocation into the nucleus to impact fatty acid oxidation and promoting lipid transport and secretion of VLDL[21]. Additionally, FGF21 appears to increase hepatic expression of LDLR, which functions not only to clear VLDL and LDL from the circulatory system, but also to promote the post-translational degradation of ApoB to subsequently reduce secretion of VLDL particles[21]. In adipose tissue, FGF21 accelerates TRL turnover as a result of activating BAT and browning of WAT[22,52]. Additionally, FGF21 has been shown to suppress adipose tissue lipolysis, increase adiponectin levels and decrease insulin resistance which also may impact hepatic steatosis[18,53]. Overall, the safety and tolerability profiles of pegozafermin were consistent with previous data, with mild to moderate gastrointestinal disturbance being the most common TEAE[23,24]. There were no serious TEAEs related to the study drug. One limitation of this study is the lack of power to assess clinical events, such as pancreatitis, liver failure or cardiovascular endpoints. Another is that the majority of subjects were Caucasian men, which may limit the generalizability of the data. While we acknowledge that fibrate use was likely underrepresented in the study, our overall utilization patterns are very similar to other reported real-world data in SHTG patients. Further safety and tolerability data from a longer period of drug exposure at the target dose are necessary.

In summary, the FGF21 analog pegozafermin significantly reduced atherogenic lipoproteins, ApoC3 and liver fat in patients with SHTG and has the potential to positively impact other aspects of metabolic dysregulation. Indeed, these "metabolic patients" are likely to benefit the most from a therapy that can function as a metabolic regulator across multiple comorbidities. If these findings are confirmed in an appropriately powered phase 3 trial, pegozafermin may be useful to treat SHTG and simultaneously address several other cardiometabolic risk factors.

REFERENCES

ADDIN EN.REFLIST 1. Wang, G. J., Gao, C. F., Wei, D., Wang, C. & Ding, S. Q. Acute pancreatitis: etiology and common pathogenesis. *World J Gastroenterol* 15, 1427-1430 (2009).
2. Anderson, F., Thomson, S. R., Clarke, D. L. & Buccimazza, I. Dyslipidaemic pancreatitis clinical assessment and analysis of disease severity and outcomes. *Pancreatology* 9, 252-257 (2009).
3. Yuan, G., Al-Shali, K. Z. & Hegele, R. A. Hypertriglyceridemia: its etiology, effects and treatment. *CMAJ* 176, 1113-1120 (2007).
4. Ganda, O. P., Bhatt, D. L., Mason, R. P., Miller, M. & Boden, W. E. Unmet need for adjunctive dyslipidemia therapy in hypertriglyceridemia management. *J Am Coll Cardiol* 72, 330-343 (2018).
5. Toth, P. P., et al. High triglycerides are associated with increased cardiovascular events, medical costs, and resource use: a real-world administrative claims analysis of statin-treated patients with high residual cardiovascular risk. *J Am Heart Assoc* 7, e008740 (2018).
6. Klempfner, R., et al. Elevated triglyceride level is independently associated with increased all-cause mortality in patients with established coronary heart disease: twenty-two-year follow-up of the Bezafibrate Infarction Prevention Study and Registry. *Circ Cardiovasc Qual Outcomes* 9, 100-108 (2016).
7. Nichols, G. A., Philip, S., Reynolds, K., Granowitz, C. B. & Fazio, S. Increased cardiovascular risk in hypertriglyceridemic patients with statin-controlled LDL cholesterol. *J Clin Endocrinol Metab* 103, 3019-3027 (2018).
8. Libby, P. Triglycerides on the rise: should we swap seats on the seesaw? *Eur Heart J* 36, 774-776 (2015).

9. Bhatt, D. L., et al. Cardiovascular risk reduction with icosapent ethyl for hypertriglyceridemia. *N Engl J Med* 380, 11-22 (2019).
10. Nichols, G. A., Philip, S., Reynolds, K., Granowitz, C. B. & Fazio, S. Increased residual cardiovascular risk in patients with diabetes and high versus normal triglycerides despite statin-controlled LDL cholesterol. *Diabetes Obes Metab* 21, 366-371 (2019).
11. Virani, S. S., et al. 2021 ACC expert consensus decision pathway on the management of ASCVD risk reduction in patients with persistent hypertriglyceridemia: a report of the American College of Cardiology Solution Set Oversight Committee. *J Am Coll Cardiol* 78, 960-993 (2021).
12. American College of Cardiology. Hypertriglyceridemia management according to the 2018 AHA/ACC guideline. https://www.acc.org/latest-in-cardiology/articles/2019/01/11/07/39/hypertriglyceridemia-management-according-to-the-2018-aha-acc-guideline. Accessed, March 2023.
13. Rosenson, R. S. & Eckel, R. H. Hypertriglyceridemia in adults: management. https://www.uptodate.com/contents/hypertriglyceridemia-in-adults-management. Accessed, March 2023.
14. Xing, J., et al. Triglycerides mediate body mass index and nonalcoholic fatty liver disease: a population-based study. *Obes Facts* 14, 190-196 (2021).
15. Rashid, N., Sharma, P. P., Scott, R. D., Lin, K. J. & Toth, P. P. Severe hypertriglyceridemia and factors associated with acute pancreatitis in an integrated health care system. *J Clin Lipidol* 10, 880-890 (2016).
16. Pejic, R. N. & Lee, D. T. Hypertriglyceridemia. J Am Board Fam Med 19, 310-316 (2006).
17. Lin, X., Liu, Y. B. & Hu, H. Metabolic role of fibroblast growth factor 21 in liver, adipose and nervous system tissues. *Biomed Rep* 6, 495-502 (2017).
18. Tillman, E. J. & Rolph, T. FGF21: an emerging therapeutic target for non-alcoholic steatohepatitis and related metabolic diseases. *Front Endocrinol (Lausanne)* 11, 601290 (2020).
19. Kliewer, S. A. & Mangelsdorf, D. J. A dozen years of discovery: insights into the physiology and pharmacology of FGF21. *Cell Metab* 29, 246-253 (2019). Stojsavljevic-Shapeski, S., Duvnjak, M., Virovic-Jukic, L., Hrabar, D. & Smircic Duvnjak, L. New drugs on the block-emerging treatments for nonalcoholic steatohepatitis. *J Clin Transl Hepatol* 9, 51-59 (2021).
21. Kong, Y., et al. FGF21 reduces lipid accumulation in bovine hepatocytes by enhancing lipid oxidation and reducing lipogenesis via AMPK signaling. *Animals (Basel)* 12, 939-958 (2022).
22. Liu, C., et al. Pharmacological treatment with FGF21 strongly improves plasma cholesterol metabolism to reduce atherosclerosis. *Cardiovasc Res* 118, 489-502 (2022).
23. Frias, J. P., et al. B1089-100 demonstrated robust reductions in liver fat and liver fat volume (LFV) by MRI-PDFF, favorable tolerability and potential for weekly (QW) or every 2 weeks (Q2W) dosing in a phase 1b/2a placebo-controlled, double-blind, multiple ascending dose study in NASH. *J Endocr Soc* 5, A5-A6 (2021).
24. Alkhouri, N., et al. Pegozafermin led to significant metabolic benefits, in addition to robust beneficial effects on the liver, in an open-label cohort of a phase 1b/2a study in subjects with non-alcoholic steatohepatitis (NASH). *J Hepatol* 77, 5732 (2022).
25. Gaich, G., et al. The effects of LY2405319, an FGF21 analog, in obese human subjects with type 2 diabetes. *Cell Metab* 18, 333-340 (2013).
26. Talukdar, S., et al. A long-acting FGF21 molecule, PF-05231023, decreases body weight and improves lipid profile in non-human primates and type 2 diabetic subjects. *Cell Metab* 23, 427-440 (2016).
27. Charles, E. D., et al. Pegbelfermin (BMS-986036), pEGylated FGF21, in patients with obesity and type 2 diabetes: results from a randomized phase 2 study. *Obesity (Silver Spring)* 27, 41-49 (2019).
28. Kaufman, A., Abuqayyas, L., Denney, W. S., Tillman, E. J. & Rolph, T. AKR-001, an Fc-FGF21 analog, showed sustained pharmacodynamic effects on insulin sensitivity and lipid metabolism in type 2 diabetes patients. *Cell Rep Med* 1, 100057 (2020).
29. Harrison, S. A., et al. Efruxifermin in non-alcoholic steatohepatitis: a randomized, double-blind, placebo-controlled, phase 2a trial. *Nat Med* 27, 1262-1271 (2021). Lin, W., Zhang, T., Zhou, Y., Zheng, J. & Lin, Z. Advances in biological functions and clinical studies of FGF21. *Diabetes Metab Syndr Obes* 14, 3281-3290 (2021).
31. Christian, J. B., et al. Determining triglyceride reductions needed for clinical impact in severe hypertriglyceridemia. *Am J Med* 127, 36-44 e31 (2014).
32. Toth, P. P., Grabner, M., Ramey, N. & Higuchi, K. Clinical and economic outcomes in a real-world population of patients with elevated triglyceride levels. *Atherosclerosis* 237, 790-797 (2014).
33. Saadatagah, S., et al. Coronary heart disease risk ssociated with primary isolated hypertriglyceridemia; a population-based study. *J Am Heart Assoc* 10, e019343 (2021).
34. Wong, N. D., et al. Residual dyslipidemia among United States adults treated with lipid modifying therapy (data from National Health and Nutrition Examination Survey 2009-2010). *Am J Cardiol* 112, 373-379 (2013).
35. Das Pradhan, A., et al. Triglyceride lowering with pemafibrate to reduce cardiovascular risk. *N Engl J Med* 387, 1923-1934 (2022).
36. Rosenson, R. S., et al. Evinacumab in severe hypertriglyceridemia with or without lipoprotein lipase pathway mutations: a phase 2 randomized trial. *Nat Med* 29, 729-737 (2023).
37. Fazio, S. Fibrates—the other life-saving drugs. *US Cardiol* 1, 1-6 (2004).
38. Bhatt, D. L., et al. Pegozafermin provides beneficial lipid effects in subjects with severe hypertriglyceridemia regardless of background lipid therapy status: an analysis of the phase 2 ENTRIGUE study. *J Am Coll Cardiol* 81, 1765-1765 (2023).
39. European Medicines Agency. Waylivra Summary of Product Characteristics. https://www.ema.europa.eu/en/documents/product-information/waylivra-epar-product-information_en.pdf. Accessed, March 2023.
40. Pfizer Inc. and Ionis Pharmaceuticals Inc. Pfizer and Ionis announce discontinuation of vupanorsen clinical development program. https://www.pfizer.com/news/press-release/press-release-detail/pfizer-and-ionis-announce-discontinuation-vupanorsen. Accessed, March 2023.
41. Watts, G. F., et al. ARO-ANG3, an investigational RNAi therapeutic, decreases serum angiopoietin-like protein 3, triglycerides, and cholesterol in patients with mixed dyslipidemia (Abstract 19416). *Circulation* 146, e569-e611 (2022).

42. Gaudet, D., et al. ARO-APOC3, an investigational RNAi therapeutic, decreases serum apolipoprotein C3, triglyceride, and non-HDL-C concentrations while increasing HDL-C in patients with severe hypertriglyceridemia (Abstract 19451). *Circulation* 146, e569-e611 (2022).
43. Guo, Y. Y., Li, H. X., Zhang, Y. & He, W. H. Hypertriglyceridemia-induced acute pancreatitis: progress on disease mechanisms and treatment modalities. *Discov Med* 27, 101-109 (2019).
44. Fisher, F. M. & Maratos-Flier, E. Understanding the physiology of FGF21. *Annu Rev Physiol* 78, 223-241 (2016).
45. Valdivielso, P., Ramirez-Bueno, A. & Ewald, N. Current knowledge of hypertriglyceridemic pancreatitis. *Eur J Intern Med* 25, 689-694 (2014).
46. Otokozawa, S., et al. Fasting and postprandial apolipoprotein B-48 levels in healthy, obese, and hyperlipidemic subjects. *Metabolism* 58, 1536-1542 (2009).
47. Taskinen, M. R., et al. Postprandial metabolism of apolipoproteins B48, B100, C-III, and E in humans with APOC3 loss-of-function mutations. *JCI Insight* 7, e160607 (2022).
48. Loomba, R. MRI-proton density fat fraction treatment response criteria in nonalcoholic steatohepatitis. *Hepatology* 73, 881-883 (2021).
49. Xu, C., et al. Influence of fatty liver on the severity and clinical outcome in acute pancreatitis. *PloS one* 10, e0142278 (2015).
50. Yoon, S. B., et al. Impact of fatty liver on acute pancreatitis severity. *Gastroenterol Res Pract* 2017, 4532320 (2017).
51. Wu, D., et al. Nonalcoholic fatty liver disease aggravated the severity of acute pancreatitis in patients. *Biomed Res Int* 2019, 9583790 (2019).
52. Cuevas-Ramos, D., Mehta, R. & Aguilar-Salinas, C. A. Fibroblast growth factor 21 and browning of white adipose tissue. *Front Physiol* 10, 37 (2019).
53. Hui, X., Feng, T., Liu, Q., Gao, Y. & Xu, A. The FGF21-adiponectin axis in controlling energy and vascular homeostasis. *J Mol Cell Biol* 8, 110-119 (2016).

```
                               SEQUENCE LISTING

Sequence total quantity: 28
SEQ ID NO: 1           moltype = AA  length = 182
FEATURE                Location/Qualifiers
source                 1..182
                       mol_type = protein
                       organism = Homo sapiens
SEQUENCE: 1
MHPIPDSSPL LQFGGQVRQR YLYTDDAQQT EAHLEIREDG TVGGAADQSP ESLLQLKALK   60
PGVIQILGVK TSRFLCQRPD GALYGSLHFD PEACSFRELL LEDGYNVYQS EAHGLPLHLP   120
GNKSPHRDPA PRGPARFLPL PGLPPALPEP PGILAPQPPD VGSSDPLSMV GPSQGRSPSY   180
AS                                                                 182

SEQ ID NO: 2           moltype = AA  length = 182
FEATURE                Location/Qualifiers
REGION                 1..182
                       note = mutant
source                 1..182
                       mol_type = protein
                       organism = synthetic construct
SEQUENCE: 2
MHPIPDSSPL LQFGGQVRQR YLYTDDAQQT EAHLEIREDG TVGGAADQSP ESLLQLKALK   60
PGVIQILGVK TSRFLCQRPD GALYGSLHFD PEACSFRELL LEDGYNVYQS EAHGLPLHLP   120
GNKSPHRDPA PRGPARFLPL PGLPPALPEP PGILAPQPPD VGSSDPLSMV GPTQGASPSY   180
AS                                                                 182

SEQ ID NO: 3           moltype = AA  length = 182
FEATURE                Location/Qualifiers
REGION                 1..182
                       note = mutant
source                 1..182
                       mol_type = protein
                       organism = synthetic construct
SEQUENCE: 3
MHPIPDSSPL LQFGGQVRQR YLYTDDAQQT EAHLEIREDG TVGGAADQSP ESLLQLKALK   60
PGVIQILGVK TSRFLCQRPD GALYGSLHFD PEACSFRELL LEDGYNVYQS EAHGLPLHLP   120
GNKSPHRDPA PRGPARFLPL PGLPPALPEP PGILAPQPPD VGSSDPLSMV GPTQGAMPSY   180
AS                                                                 182

SEQ ID NO: 4           moltype = AA  length = 182
FEATURE                Location/Qualifiers
REGION                 1..182
                       note = mutant
source                 1..182
                       mol_type = protein
                       organism = synthetic construct
SEQUENCE: 4
MHPIPDSSPL LQFGGQVRQR YLYTDDAQQT EAHLEIREDG TVGGAADQSP ESLLQLKALK   60
PGVIQILGVK TSRFLCQRPD GALYGSLHFD PEACSFRELL LEDGYNVYQS EAHGLPLHLP   120
GNKSPHRDPA PRGPARFLPL PGLPPALPEP PGILAPTPPD VGSSDPLSMV GPSQGRSPSY   180
AS                                                                 182
```

```
SEQ ID NO: 5              moltype = AA  length = 182
FEATURE                   Location/Qualifiers
REGION                    1..182
                          note = mutant
source                    1..182
                          mol_type = protein
                          organism = synthetic construct
SEQUENCE: 5
MHPIPTSSPL LQFGGQVRQR YLYTDDAQQT EAHLEIREDG TVGGAADQSP ESLLQLKALK    60
PGVIQILGVK TSRFLCQRPD GALYGSLHFD PEACSFRELL LEDGYNVYQS EAHGLPLHLP   120
GNKSPHRDPA PRGPARFLPL PGLPPALPEP PGILAPQPPD VGSSDPLSMV GPSQGRSPSY   180
AS                                                                 182

SEQ ID NO: 6              moltype = AA  length = 182
FEATURE                   Location/Qualifiers
REGION                    1..182
                          note = mutant
source                    1..182
                          mol_type = protein
                          organism = synthetic construct
SEQUENCE: 6
MHPTPDSSPL LQFGGQVRQR YLYTDDAQQT EAHLEIREDG TVGGAADQSP ESLLQLKALK    60
PGVIQILGVK TSRFLCQRPD GALYGSLHFD PEACSFRELL LEDGYNVYQS EAHGLPLHLP   120
GNKSPHRDPA PRGPARFLPL PGLPPALPEP PGILAPQPPD VGSSDPLSMV GPSQGRSPSY   180
AS                                                                 182

SEQ ID NO: 7              moltype = AA  length = 182
FEATURE                   Location/Qualifiers
REGION                    1..182
                          note = mutant
source                    1..182
                          mol_type = protein
                          organism = synthetic construct
SEQUENCE: 7
MHPIPDSSPT LQFGGQVRQR YLYTDDAQQT EAHLEIREDG TVGGAADQSP ESLLQLKALK    60
PGVIQILGVK TSRFLCQRPD GALYGSLHFD PEACSFRELL LEDGYNVYQS EAHGLPLHLP   120
GNKSPHRDPA PRGPARFLPL PGLPPALPEP PGILAPQPPD VGSSDPLSMV GPSQGRSPSY   180
AS                                                                 182

SEQ ID NO: 8              moltype = AA  length = 182
FEATURE                   Location/Qualifiers
REGION                    1..182
                          note = mutant
source                    1..182
                          mol_type = protein
                          organism = synthetic construct
SEQUENCE: 8
MHPIPDSSPL LQFGGQVRQR YLYTDDAQQT EAHLEIREDG TVGGAADQSP TSLLQLKALK    60
PGVIQILGVK TSRFLCQRPD GALYGSLHFD PEACSFRELL LEDGYNVYQS EAHGLPLHLP   120
GNKSPHRDPA PRGPARFLPL PGLPPALPEP PGILAPQPPD VGSSDPLSMV GPSQGRSPSY   180
AS                                                                 182

SEQ ID NO: 9              moltype = AA  length = 182
FEATURE                   Location/Qualifiers
REGION                    1..182
                          note = mutant
source                    1..182
                          mol_type = protein
                          organism = synthetic construct
SEQUENCE: 9
MHPIPDSSPL LQFGGQVRQR YLYTDDAQQT EAHLEIREDG TVGGAADQSP ESLLQLKALK    60
PTVIQILGVK TSRFLCQRPD GALYGSLHFD PEACSFRELL LEDGYNVYQS EAHGLPLHLP   120
GNKSPHRDPA PRGPARFLPL PGLPPALPEP PGILAPQPPD VGSSDPLSMV GPSQGRSPSY   180
AS                                                                 182

SEQ ID NO: 10             moltype = AA  length = 182
FEATURE                   Location/Qualifiers
REGION                    1..182
                          note = mutant
source                    1..182
                          mol_type = protein
                          organism = synthetic construct
SEQUENCE: 10
MHPIPDSSPL LQFGGQVRQR YLYTDDAQQT EAHLEIREDG TVGGAADQSP ESLLQLKALK    60
PGVIQILGVK TSRFLCQRPT GALYGSLHFD PEACSFRELL LEDGYNVYQS EAHGLPLHLP   120
GNKSPHRDPA PRGPARFLPL PGLPPALPEP PGILAPQPPD VGSSDPLSMV GPSQGRSPSY   180
AS                                                                 182

SEQ ID NO: 11             moltype = AA  length = 182
```

| FEATURE | Location/Qualifiers |
|---|---|
| REGION | 1..182 |
| | note = mutant |
| source | 1..182 |
| | mol_type = protein |
| | organism = synthetic construct |

SEQUENCE: 11
```
MHPIPDSSPL LQFGGQVRQR YLYTDDAQQT EAHLEIREDG TVGGAADQSP ESLLQLKALK   60
PGVIQILGVK TSRFLCQRPD GALYGSLHFD PTACSFRELL LEDGYNVYQS EAHGLPLHLP  120
GNKSPHRDPA PRGPARFLPL PGLPPALPEP PGILAPQPPD VGSSDPLSMV GPSQGRSPSY  180
AS                                                                182
```

| SEQ ID NO: 12 | moltype = AA   length = 182 |
|---|---|
| FEATURE | Location/Qualifiers |
| REGION | 1..182 |
| | note = mutant |
| source | 1..182 |
| | mol_type = protein |
| | organism = synthetic construct |

SEQUENCE: 12
```
MHPIPDSSPL LQFGGQVRQR YLYTDDAQQT EAHLEIREDG TVGGAADQSP ESLLQLKALK   60
PGVIQILGVK TSRFLCQRPD GALYGSLHFD PEACSFRELL LEDGYNVYQS EAHGLPTHLP  120
GNKSPHRDPA PRGPARFLPL PGLPPALPEP PGILAPQPPD VGSSDPLSMV GPSQGRSPSY  180
AS                                                                182
```

| SEQ ID NO: 13 | moltype = AA   length = 182 |
|---|---|
| FEATURE | Location/Qualifiers |
| REGION | 1..182 |
| | note = mutant |
| source | 1..182 |
| | mol_type = protein |
| | organism = synthetic construct |

SEQUENCE: 13
```
MHPIPDSSPL LQFGGQVRQR YLYTDDAQQT EAHLEIREDG TVGGAADQSP ESLLQLKALK   60
PGVIQILGVK TSRFLCQRPD GALYGSLHFD PEACSFRELL LEDGYNVYQS EAHGLPLHLP  120
TNKSPHRDPA PRGPARFLPL PGLPPALPEP PGILAPQPPD VGSSDPLSMV GPSQGRSPSY  180
AS                                                                182
```

| SEQ ID NO: 14 | moltype = AA   length = 182 |
|---|---|
| FEATURE | Location/Qualifiers |
| REGION | 1..182 |
| | note = mutant |
| source | 1..182 |
| | mol_type = protein |
| | organism = synthetic construct |

SEQUENCE: 14
```
MHPIPDSSPL LQFGGQVRQR YLYTDDAQQT EAHLEIREDG TVGGAADQSP ESLLQLKALK   60
PGVIQILGVK TSRFLCQRPD GALYGSLHFD PEACSFRELL LEDGYNVYQS EAHGLPLHLP  120
GNKSPTRDPA PRGPARFLPL PGLPPALPEP PGILAPQPPD VGSSDPLSMV GPSQGRSPSY  180
AS                                                                182
```

| SEQ ID NO: 15 | moltype = AA   length = 182 |
|---|---|
| FEATURE | Location/Qualifiers |
| REGION | 1..182 |
| | note = mutant |
| source | 1..182 |
| | mol_type = protein |
| | organism = synthetic construct |

SEQUENCE: 15
```
MHPIPDSSPL LQFGGQVRQR YLYTDDAQQT EAHLEIREDG TVGGAADQSP ESLLQLKALK   60
PGVIQILGVK TSRFLCQRPD GALYGSLHFD PEACSFRELL LEDGYNVYQS EAHGLPLHLP  120
GNKSPHRDPT PRGPARFLPL PGLPPALPEP PGILAPQPPD VGSSDPLSMV GPSQGRSPSY  180
AS                                                                182
```

| SEQ ID NO: 16 | moltype = AA   length = 182 |
|---|---|
| FEATURE | Location/Qualifiers |
| REGION | 1..182 |
| | note = mutant |
| source | 1..182 |
| | mol_type = protein |
| | organism = synthetic construct |

SEQUENCE: 16
```
MHPIPDSSPL LQFGGQVRQR YLYTDDAQQT EAHLEIREDG TVGGAADQSP ESLLQLKALK   60
PGVIQILGVK TSRFLCQRPD GALYGSLHFD PEACSFRELL LEDGYNVYQS EAHGLPLHLP  120
GNKSPHRDPA PTGPARFLPL PGLPPALPEP PGILAPQPPD VGSSDPLSMV GPSQGRSPSY  180
AS                                                                182
```

| SEQ ID NO: 17 | moltype = AA   length = 182 |
|---|---|
| FEATURE | Location/Qualifiers |

```
REGION                  1..182
                        note = mutant
source                  1..182
                        mol_type = protein
                        organism = synthetic construct
SEQUENCE: 17
MHPIPDSSPL LQFGGQVRQR YLYTDDAQQT EAHLEIREDG TVGGAADQSP ESLLQLKALK    60
PGVIQILGVK TSRFLCQRPD GALYGSLHFD PEACSFRELL LEDGYNVYQS EAHGLPLHLP   120
GNKSPHRDPA PRGPTRFLPL PGLPPALPEP PGILAPQPPD VGSSDPLSMV GPSQGRSPSY   180
AS                                                                 182

SEQ ID NO: 18           moltype = AA  length = 182
FEATURE                 Location/Qualifiers
REGION                  1..182
                        note = mutant
source                  1..182
                        mol_type = protein
                        organism = synthetic construct
SEQUENCE: 18
MHPIPDSSPL LQFGGQVRQR YLYTDDAQQT EAHLEIREDG TVGGAADQSP ESLLQLKALK    60
PGVIQILGVK TSRFLCQRPD GALYGSLHFD PEACSFRELL LEDGYNVYQS EAHGLPLHLP   120
GNKSPHRDPA PRGPARFLPT PGLPPALPEP PGILAPQPPD VGSSDPLSMV GPSQGRSPSY   180
AS                                                                 182

SEQ ID NO: 19           moltype = AA  length = 182
FEATURE                 Location/Qualifiers
REGION                  1..182
                        note = mutant
source                  1..182
                        mol_type = protein
                        organism = synthetic construct
SEQUENCE: 19
MHPIPDSSPL LQFGGQVRQR YLYTDDAQQT EAHLEIREDG TVGGAADQSP ESLLQLKALK    60
PGVIQILGVK TSRFLCQRPD GALYGSLHFD PEACSFRELL LEDGYNVYQS EAHGLPLHLP   120
GNKSPHRDPA PRGPARFLPL PTLPPALPEP PGILAPQPPD VGSSDPLSMV GPSQGRSPSY   180
AS                                                                 182

SEQ ID NO: 20           moltype = AA  length = 183
FEATURE                 Location/Qualifiers
REGION                  1..183
                        note = mutant
source                  1..183
                        mol_type = protein
                        organism = synthetic construct
SEQUENCE: 20
MHPIPDSSPL LQFGGQVRQR YLYTDDAQQT EAHLEIREDG TVGGAADQSP ESLLQLKALK    60
PGVIQILGVK TSRFLCQRPD GALYGSLHFD PEACSFRELL LEDGYNVYQS EAHGLPLHLP   120
GNKSPHRDPA PRGPARFLPL PGLPTPALPE PPGILAPQPP DVGSSDPLSM VGPSQGRSPS   180
YAS                                                                183

SEQ ID NO: 21           moltype = AA  length = 182
FEATURE                 Location/Qualifiers
REGION                  1..182
                        note = mutant
source                  1..182
                        mol_type = protein
                        organism = synthetic construct
SEQUENCE: 21
MHPIPDSSPL LQFGGQVRQR YLYTDDAQQT EAHLEIREDG TVGGAADQSP ESLLQLKALK    60
PGVIQILGVK TSRFLCQRPD GALYGSLHFD PEACSFRELL LEDGYNVYQS EAHGLPLHLP   120
GNKSPHRDPA PRGPARFLPL PGLPPTLPEP PGILAPQPPD VGSSDPLSMV GPSQGRSPSY   180
AS                                                                 182

SEQ ID NO: 22           moltype = AA  length = 182
FEATURE                 Location/Qualifiers
REGION                  1..182
                        note = mutant
source                  1..182
                        mol_type = protein
                        organism = synthetic construct
SEQUENCE: 22
MHPIPDSSPL LQFGGQVRQR YLYTDDAQQT EAHLEIREDG TVGGAADQSP ESLLQLKALK    60
PGVIQILGVK TSRFLCQRPD GALYGSLHFD PEACSFRELL LEDGYNVYQS EAHGLPLHLP   120
GNKSPHRDPA PRGPARFLPL PGLPPALPTP PGILAPQPPD VGSSDPLSMV GPSQGRSPSY   180
AS                                                                 182

SEQ ID NO: 23           moltype = AA  length = 183
FEATURE                 Location/Qualifiers
REGION                  1..183
```

```
                         note = mutant
source                   1..183
                         mol_type = protein
                         organism = synthetic construct
SEQUENCE: 23
MHPIPDSSPL LQFGGQVRQR YLYTDDAQQT EAHLEIREDG TVGGAADQSP ESLLQLKALK    60
PGVIQILGVK TSRFLCQRPD GALYGSLHFD PEACSFRELL LEDGYNVYQS EAHGLPLHLP   120
GNKSPHRDPA PRGPARFLPL PGLPPALPEP TPGILAPQPP DVGSSDPLSM VGPSQGRSPS   180
YAS                                                                 183

SEQ ID NO: 24            moltype = AA  length = 182
FEATURE                  Location/Qualifiers
REGION                   1..182
                         note = mutant
source                   1..182
                         mol_type = protein
                         organism = synthetic construct
SEQUENCE: 24
MHPIPDSSPL LQFGGQVRQR YLYTDDAQQT EAHLEIREDG TVGGAADQSP ESLLQLKALK    60
PGVIQILGVK TSRFLCQRPD GALYGSLHFD PEACSFRELL LEDGYNVYQS EAHGLPLHLP   120
GNKSPHRDPA PRGPARFLPL PGLPPALPEP PTILAPQPPD VGSSDPLSMV GPSQGRSPSY   180
AS                                                                  182

SEQ ID NO: 25            moltype = AA  length = 183
FEATURE                  Location/Qualifiers
REGION                   1..183
                         note = mutant
source                   1..183
                         mol_type = protein
                         organism = synthetic construct
SEQUENCE: 25
MHPIPDSSPL LQFGGQVRQR YLYTDDAQQT EAHLEIREDG TVGGAADQSP ESLLQLKALK    60
PGVIQILGVK TSRFLCQRPD GALYGSLHFD PEACSFRELL LEDGYNVYQS EAHGLPLHLP   120
GNKSPHRDPA PRGPARFLPL PGLPPALPEP PGILAPQPTP DVGSSDPLSM VGPSQGRSPS   180
YAS                                                                 183

SEQ ID NO: 26            moltype = AA  length = 182
FEATURE                  Location/Qualifiers
REGION                   1..182
                         note = mutant
source                   1..182
                         mol_type = protein
                         organism = synthetic construct
SEQUENCE: 26
MHPIPDSSPL LQFGGQVRQR YLYTDDAQQT EAHLEIREDG TVGGAADQSP ESLLQLKALK    60
PGVIQILGVK TSRFLCQRPD GALYGSLHFD PEACSFRELL LEDGYNVYQS EAHGLPLHLP   120
GNKSPHRDPA PRGPARFLPL PGLPPALPEP PGILAPQPPT VGSSDPLSMV GPSQGRSPSY   180
AS                                                                  182

SEQ ID NO: 27            moltype = AA  length = 182
FEATURE                  Location/Qualifiers
REGION                   1..182
                         note = mutant
source                   1..182
                         mol_type = protein
                         organism = synthetic construct
SEQUENCE: 27
MHPIPDSSPL LQFGGQVRQR YLYTDDAQQT EAHLEIREDG TVGGAADQSP ESLLQLKALK    60
PGVIQILGVK TSRFLCQRPD GALYGSLHFD PEACSFRELL LEDGYNVYQS EAHGLPLHLP   120
GNKSPHRDPA PRGPARFLPL PGLPPALPEP PGILAPQPPD VGSSDPTSMV GPSQGRSPSY   180
AS                                                                  182

SEQ ID NO: 28            moltype = AA  length = 182
FEATURE                  Location/Qualifiers
REGION                   1..182
                         note = mutant
source                   1..182
                         mol_type = protein
                         organism = synthetic construct
SEQUENCE: 28
MHPIPDSSPL LQFGGQVRQR YLYTDDAQQT EAHLEIREDG TVGGAADQSP ESLLQLKALK    60
PGVIQILGVK TSRFLCQRPD GALYGSLHFD PEACSFRELL LEDGYNVYQS EAHGLPLHLP   120
GNKSPHRDPA PRGPARFLPL PGLPPALPEP PGILAPQPPD VGSSDPLSMV GPSQGRSPTY   180
AS                                                                  182
```

The invention claimed is:

1. A method of treating severe hypertriglyceridemia (SHTG) in a subject in need thereof, comprising:
administering once a week to the subject in need thereof a pharmaceutical composition comprising from 9 mg to 30 mg of a mutant Fibroblast Growth Factor-21 (FGF-21) peptide conjugate and a pharmaceutically acceptable carrier,
wherein the subject in need thereof has SHTG,
wherein the subject in need thereof has fasting triglycerides (TG)≥500 mg/dL and ≤2000 mg/dL,
wherein the mutant FGF-21 peptide conjugate comprises:
i) a mutant FGF-21 peptide comprising the amino acid sequence of SEQ ID NO: 2,
ii) a glycosyl moiety, and
iii) a 20 kDa polyethylene glycol (PEG), wherein the mutant FGF-21 peptide is attached to the glycosyl moiety by a covalent bond between a threonine at amino acid position 173 of SEQ ID NO: 2 and a first site of the glycosyl moiety and wherein the glycosyl moiety is attached to the 20 kDa PEG by a covalent bond between a second site of the glycosyl moiety and the 20 kDa PEG,
wherein administration of the pharmaceutical composition results in a reduction of triglyceride levels by at least 20% from baseline, and in fasting triglyceride levels <500 mg/dL.

2. The method of claim 1, wherein the administration results in a reduction of non-HDL cholesterol levels by at least 10% from baseline, reduction of apoB levels by at least 10% from baseline, reduction of apoC3 levels by at least 10% from baseline, or a combination thereof.

3. The method of claim 1, wherein the administration results in an increase of HDL cholesterol levels by at least 10% from baseline, an increase of adiponectin levels by at least 10% from baseline or a combination thereof.

4. The method of claim 1, comprising administering the pharmaceutical composition to the subject in need thereof for 8 weeks or more.

5. The method of claim 1, wherein the pharmaceutical composition comprises 9 mg of the mutant FGF-21 peptide conjugate.

6. The method of claim 1, wherein the pharmaceutical composition comprises from 15 mg to 18 mg of the mutant FGF-21 peptide conjugate.

7. The method of claim 1, wherein the pharmaceutical composition comprises from 27 mg to 30 mg of the mutant FGF-21 peptide conjugate.

8. The method of claim 7, wherein the administration results in reduction of alanine transaminase (ALT) marker by at least 10%, reduction of aspartate aminotransferase (AST) marker by at least 10%, median reduction of High-sensitivity C-reactive protein (hsCRP) marker by at least 10% or a combination thereof.

9. The method of claim 7, wherein the administration results in reduction of fasting plasma glucose by at least 10%, reduction of HBA1c by at least 0.2% or a combination thereof.

10. The method of claim 1, wherein the subject in need thereof is on background lipid modifying therapy (LMT), wherein the LMT comprises statins, prescription fish oil, fibrates or combinations thereof, and wherein the administration results in a reduction of levels of non-HDL cholesterol by at least 10% from baseline.

11. The method of claim 1, wherein the subject in need thereof is on background LMT, wherein the LMT comprises statins, prescription fish oil, fibrates or combinations thereof, and wherein the administration results in a reduction of levels of apoB cholesterol by at least 10% from baseline.

12. The method of claim 1, wherein administration of the pharmaceutical composition results in a median reduction of triglyceride levels by at least 40% from baseline.

13. The method of claim 1, comprising administering the pharmaceutical composition sub-subcutaneously.

14. A method of treating severe hypertriglyceridemia (SHTG) in a subject in need thereof, comprising:
administering once every two weeks to the subject in need thereof a pharmaceutical composition comprising from 31 mg to 44 mg of a mutant Fibroblast Growth Factor-21 (FGF-21) Peptide conjugate and a pharmaceutically acceptable carrier,
wherein the subject in need thereof has SHTG,
wherein the subject in need thereof has fasting triglycerides (TG)≥500 mg/dL and ≤2000 mg/dL,
wherein the mutant FGF-21 peptide conjugate comprises:
i) a mutant FGF-21 peptide comprising the amino acid sequence of SEQ ID NO: 2,
ii) a glycosyl moiety, and
iii) a 20 kDa polyethylene glycol (PEG), wherein the mutant FGF-21 peptide is attached to the glycosyl moiety by a covalent bond between a threonine at amino acid position 173 of SEQ ID NO: 2 and a first site of the glycosyl moiety and wherein the glycosyl moiety is attached to the 20 kDa PEG by a covalent bond between a second site of the glycosyl moiety and the 20 kDa PEG,
wherein administration of the pharmaceutical composition results in a reduction of triglyceride levels by at least 20% from baseline, and in fasting triglyceride levels <500 mg/dL.

15. The method of claim 14, wherein the administration results in a reduction of non-HDL cholesterol levels by at least 10% from baseline, reduction of apoB levels by at least 10% from baseline, reduction of apoC3 levels by at least 10% from baseline, or a combination thereof.

16. The method of claim 14, wherein the administration results in an increase of HDL cholesterol levels by at least 10% from baseline, an increase of adiponectin levels by at least 10% from baseline or a combination thereof.

17. The method of claim 14, comprising administering the pharmaceutical composition to the subject in need thereof for 8 weeks or more.

18. The method of claim 14, wherein the pharmaceutical composition comprises from 36 mg to 44 mg of the mutant FGF-21 peptide conjugate.

19. The method of claim 18, wherein the administration results in median reduction of hsCRP marker by at least 10%.

20. The method of claim 14, wherein the subject is on background LMT, wherein the LMT comprises statins, prescription fish oil, fibrates or combinations thereof, and wherein the administration results in a reduction of levels of non-HDL cholesterol by at least 10% from baseline.

21. The method of claim 14, wherein the subject is on background LMT, wherein the LMT comprises statins, prescription fish oil, fibrates or combinations thereof, and wherein the administration results in a reduction of levels of apoB cholesterol by at least 10% from baseline.

22. The method of claim 14, wherein administration of the pharmaceutical composition results in a median reduction of triglyceride levels by at least 40% from baseline.

23. The method of claim 14, comprising administering sub-subcutaneously the pharmaceutical composition.

24. A method of treating severe hypertriglyceridemia (SHTG) in a subject in need thereof, comprising:
administering once a week to the subject in need thereof a pharmaceutical composition comprising from 27 mg to 30 mg of a mutant Fibroblast Growth Factor-21 (FGF-21) peptide conjugate and a pharmaceutically acceptable carrier,
wherein the subject in need thereof has SHTG,
wherein the subject in need thereof has fasting triglycerides (TG)≥500 mg/dL and ≤2000 mg/dL,
wherein the mutant FGF-21 peptide conjugate comprises:
i) a mutant FGF-21 peptide comprising the amino acid sequence of SEQ ID NO: 2,
ii) a glycosyl moiety, and
iii) a 20 kDa polyethylene glycol (PEG), wherein the mutant FGF-21 peptide is attached to the glycosyl moiety by a covalent bond between a threonine at amino acid position 173 of SEQ ID NO: 2 and a first site of the glycosyl moiety and wherein the glycosyl moiety is attached to the 20 kDa PEG by a covalent bond between a second site of the glycosyl moiety and the 20 kDa PEG,
wherein administration of the pharmaceutical composition results in a reduction of triglyceride levels by at least 20% from baseline, in fasting triglyceride levels <500 mg/dL, and
wherein administration of the pharmaceutical composition results in one or more of the following:
reduction of alanine transaminase (ALT) marker by at least 10% from baseline,
reduction of aspartate aminotransferase (AST) marker by at least 10% from baseline,
median reduction of High-sensitivity C-reactive protein (hsCRP) marker by at least 10% from baseline,
reduction of fasting plasma glucose by at least 10% from baseline,
reduction of HBA1c by at least 0.3% from baseline,
reduction of non-HDL cholesterol levels by at least 10% from baseline,
reduction of apoB levels by at least 10% from baseline,
reduction of apoC3 levels by at least 10% from baseline,
increase of HDL cholesterol levels by at least 10% from baseline,
increase of adiponectin levels by at least 10% from baseline, and
reduction greater than 30% in liver fat from baseline.

25. The method of claim 24, comprising administering the pharmaceutical composition sub-subcutaneously for 8 weeks or more.

26. A method of treating severe hypertriglyceridemia (SHTG) in a subject in need thereof, comprising:
administering once every two weeks to the subject in need thereof a pharmaceutical composition comprising from 36 mg to 44 mg of a mutant Fibroblast Growth Factor-21 (FGF-21) peptide conjugate and a pharmaceutically acceptable carrier,
wherein the subject in need thereof has SHTG,
wherein the subject in need thereof has fasting triglycerides (TG)≥500 mg/dL and ≤2000 mg/dL,
wherein the mutant FGF-21 peptide conjugate comprises:
i) a mutant FGF-21 peptide comprising the amino acid sequence of SEQ ID NO: 2,
ii) a glycosyl moiety, and
iii) a 20 kDa polyethylene glycol (PEG), wherein the mutant FGF-21 peptide is attached to the glycosyl moiety by a covalent bond between a threonine at amino acid position 173 of SEQ ID NO: 2 and a first site of the glycosyl moiety and wherein the glycosyl moiety is attached to the 20 kDa PEG by a covalent bond between a second site of the glycosyl moiety and the 20 kDa PEG,
wherein administration of the pharmaceutical composition results in a reduction of triglyceride levels by at least 20% from baseline, in fasting triglyceride levels <500 mg/dL, and
wherein administration of the pharmaceutical composition results in one or more of the following:
median reduction of High-sensitivity C-reactive protein (hsCRP) marker by at least 10% from baseline,
reduction of non-HDL cholesterol levels by at least 10% from baseline,
reduction of apoB levels by at least 10% from baseline,
reduction of apoC3 levels by at least 10% from baseline,
increase of HDL cholesterol levels by at least 10% from baseline,
increase of adiponectin levels by at least 10% from baseline, and
reduction greater than 30% in liver fat from baseline.

27. The method of claim 26, comprising administering the pharmaceutical composition sub-subcutaneously for 8 weeks or more.

* * * * *